US011720839B2

(12) United States Patent
Scholar

(10) Patent No.: US 11,720,839 B2
(45) Date of Patent: Aug. 8, 2023

(54) PROJECT PLANNING SYSTEM

(71) Applicant: GreenGo Systems, Inc., Newport Beach, CA (US)

(72) Inventor: David A. Scholar, Newport Beach, CA (US)

(73) Assignee: GreenGo Systems, Inc., Newport Beach, CA (US)

( * ) Notice: Subject to any disclaimer, the term of this patent is extended or adjusted under 35 U.S.C. 154(b) by 85 days.

(21) Appl. No.: 17/510,112

(22) Filed: Oct. 25, 2021

(65) Prior Publication Data

US 2022/0156659 A1    May 19, 2022

Related U.S. Application Data

(63) Continuation of application No. 14/985,280, filed on Dec. 30, 2015, now Pat. No. 11,157,848, which is a continuation of application No. 12/690,026, filed on Jan. 19, 2010, now abandoned.

(60) Provisional application No. 61/177,961, filed on May 13, 2009, provisional application No. 61/145,503, filed on Jan. 16, 2009.

(51) Int. Cl.
| | |
|---|---|
| *G06Q 10/0631* | (2023.01) |
| *G06Q 10/101* | (2023.01) |
| *G06Q 10/10* | (2023.01) |
| *G06Q 50/08* | (2012.01) |
| *G06Q 50/18* | (2012.01) |
| *G06Q 10/06* | (2023.01) |
| *G06Q 30/0601* | (2023.01) |
| *G06Q 50/00* | (2012.01) |
| *G16H 10/20* | (2018.01) |
| *G16H 15/00* | (2018.01) |

(52) U.S. Cl.
CPC ....... *G06Q 10/06313* (2013.01); *G06Q 10/06* (2013.01); *G06Q 10/06315* (2013.01); *G06Q 10/101* (2013.01); *G06Q 10/103* (2013.01); *G06Q 30/0611* (2013.01); *G06Q 50/01* (2013.01); *G06Q 50/08* (2013.01); *G06Q 50/188* (2013.01); *G16H 10/20* (2018.01); *G16H 15/00* (2018.01)

(58) Field of Classification Search
CPC ................... G06Q 10/06313; G06Q 10/06315
USPC ...................................................... 705/7.23
See application file for complete search history.

(56) References Cited

U.S. PATENT DOCUMENTS

| | | |
|---|---|---|
| 5,761,674 A | 6/1998 | Ito |
| 6,381,610 B1 | 4/2002 | Gundewar et al. |

(Continued)

FOREIGN PATENT DOCUMENTS

| | | |
|---|---|---|
| DE | 10241427 A1 | 3/2004 |
| WO | WO 2006/086332 | 8/2006 |
| WO | WO 2013/013277 A1 | 1/2013 |

OTHER PUBLICATIONS

International Search Report and Written Opinion dated Aug. 31, 2010 from corresponding International Application No. PCT/US2010/021432, filed Jan. 19, 2010.

(Continued)

*Primary Examiner* — Jerry O'Connor
*Assistant Examiner* — James Webb
(74) *Attorney, Agent, or Firm* — KOS IP Law LLP

(57) ABSTRACT

An interactive and collaborative, planning, designing and facilitating tool that connects users with organized information and relevant data, providers and facilitators to resolve technical issues in conceptualizing, designing and implementing a custom project.

20 Claims, 37 Drawing Sheets

(56) References Cited

U.S. PATENT DOCUMENTS

| | | |
|---|---|---|
| 6,820,023 B1 | 11/2004 | Klassen et al. |
| 6,836,752 B2 | 12/2004 | Atasoy |
| 6,968,343 B2 | 11/2005 | Charisius et al. |
| 7,062,532 B1 | 6/2006 | Sweat et al. |
| 7,822,621 B1 | 10/2010 | Chappel |
| 2001/0032062 A1 | 10/2001 | Plaskoff et al. |
| 2001/0051913 A1 | 12/2001 | Vashistha et al. |
| 2003/0106039 A1 | 6/2003 | Rosnow et al. |
| 2004/0107010 A1 | 6/2004 | King |
| 2004/0167797 A1 | 8/2004 | Goncalves |
| 2006/0010081 A1 | 1/2006 | Williams |
| 2007/0022404 A1 | 1/2007 | Zhang et al. |
| 2007/0061181 A1 | 3/2007 | Bowden, Jr. et al. |
| 2007/0061774 A1 | 3/2007 | Chan et al. |
| 2008/0127041 A1 | 5/2008 | Gura |
| 2008/0243565 A1 | 10/2008 | Gregory |
| 2009/0006147 A1 | 1/2009 | Padmanabhan |

OTHER PUBLICATIONS

International Preliminary Report on Patentability completed Aug. 30, 2010 and dated Jul. 28, 2011 from corresponding International Application No. PCT/US2010/021432, filed Jan. 19, 2010 (8 pages).
Examiner's Report on corresponding foreign application (EP Application No. 10732232.3) from the European Patent Office dated Dec. 7, 2015.
Non-Final Office Action on corresponding (U.S. Appl. No. 12/690,026) dated Apr. 9, 2012.
Non-Final Office Action on corresponding (U.S. Appl. No. 12/690,026) dated Dec. 2, 2014.
Non-Final Office Action on co-pending (U.S. Appl. No. 14/985,280) dated Oct. 17, 2017.
Non-Final Office Action on co-pending (U.S. Appl. No. 14/985,280) dated Nov. 19, 2020.
Notice of Allowance on co-pending (U.S. Appl. No. 14/985,280) dated Jun. 24, 2021.
Fdot, Construction Contract List, Jun. 4, 2021, https://scoc.fdot.gov/#/active/8, p. 1.

BUILDING TYPE
Residential - Single Family ▽

NUMBER OF STORIES
[x] 1  [ ] 2  [ ] 3  [ ] 4+

PROJECT TYPE
New Construction ▽

SITE CONDITIONS
Flat ▽

What is important to you?
1=Not Important, 5=Very Important 1  2  [3]  4  5   Low Initial Cost
1  2  3  4  [5]   Long Term Savings
1  2  3  4  [5]   Health of Family
1  2  3  [4]  5   Style / Appearance
1  2  [3]  4  5   Environmental Impact

Find Your Style

EXTERIOR BUILDING STYLE
View All Styles ▶

Mission ▽

Add Another Style (photo)

Features:
- Smooth stucco
- Roof Parapets
- Large square pillars
- Twisted columns
- Arched entry porch Mission View Gallery ▶

INTERIOR BUILDING STYLE
View All Styles ▶

Mission ▽
Contemporary ▽

Add Another Style (photo)

Features:
- Often has single roof pitch or flat roof type
- Generally has a stucco, shell, stone or multi-type exterior Contemporary View Gallery ▶

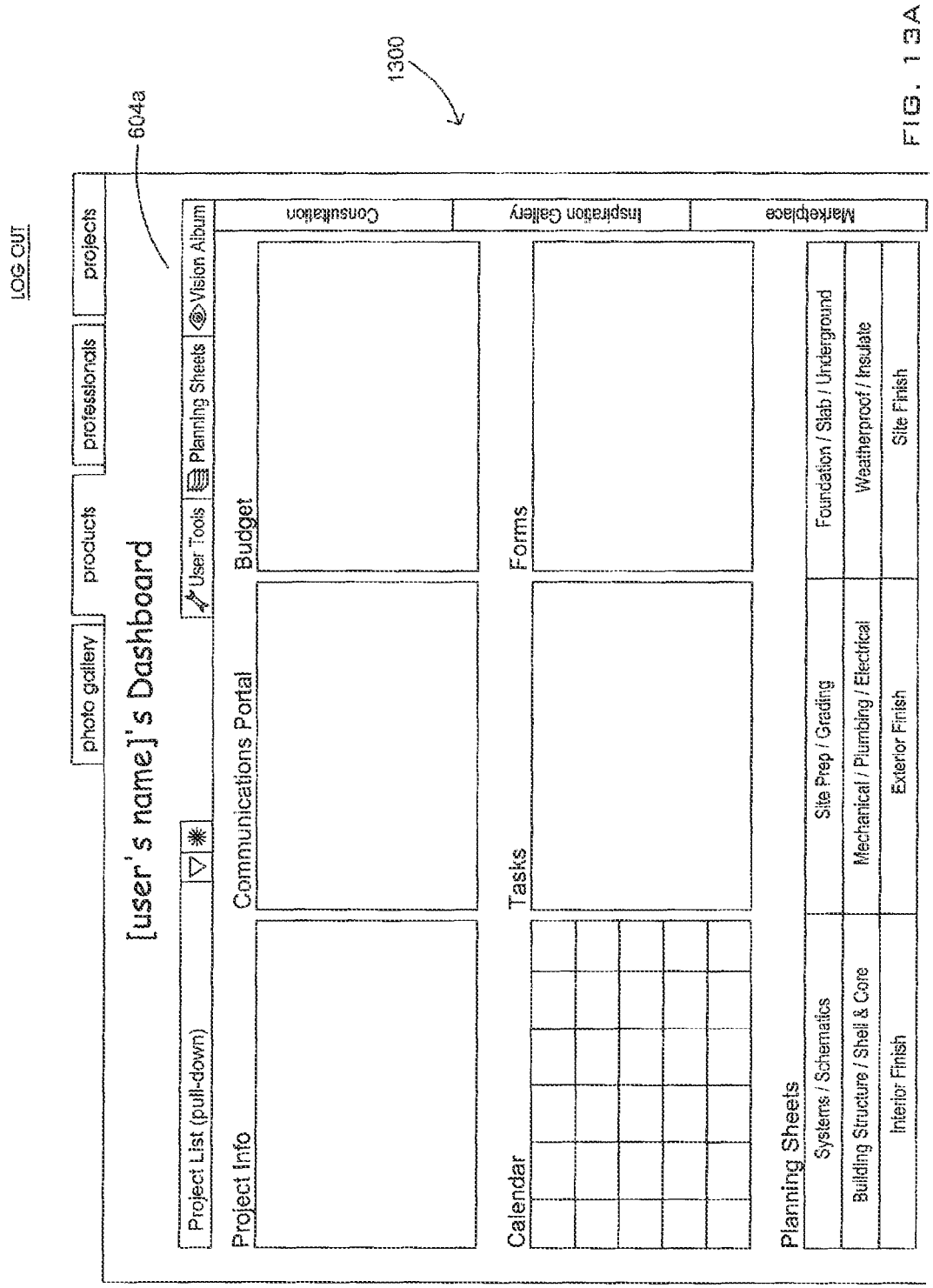

(CONT'D)(1)

(CONT'D)(2)

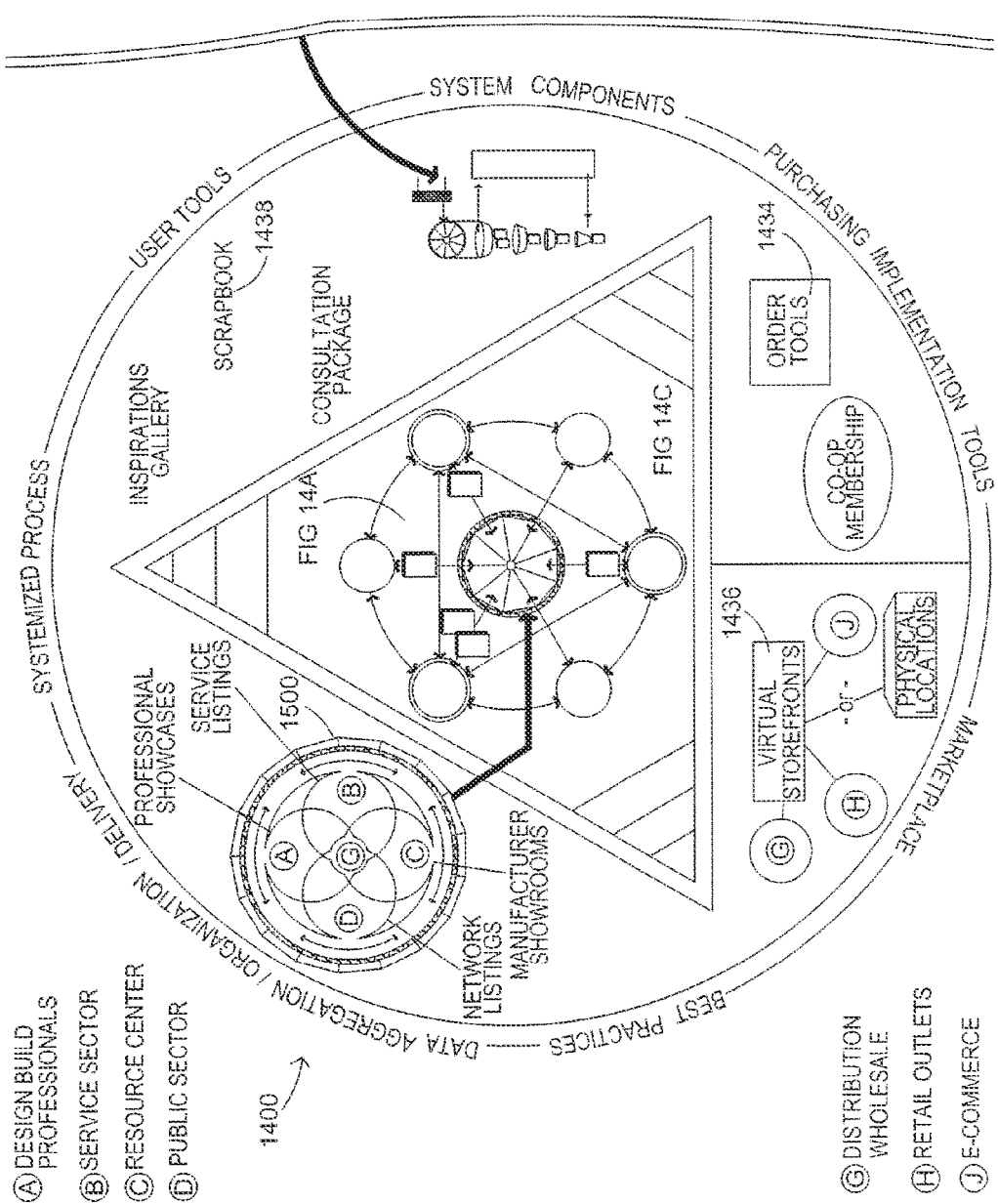

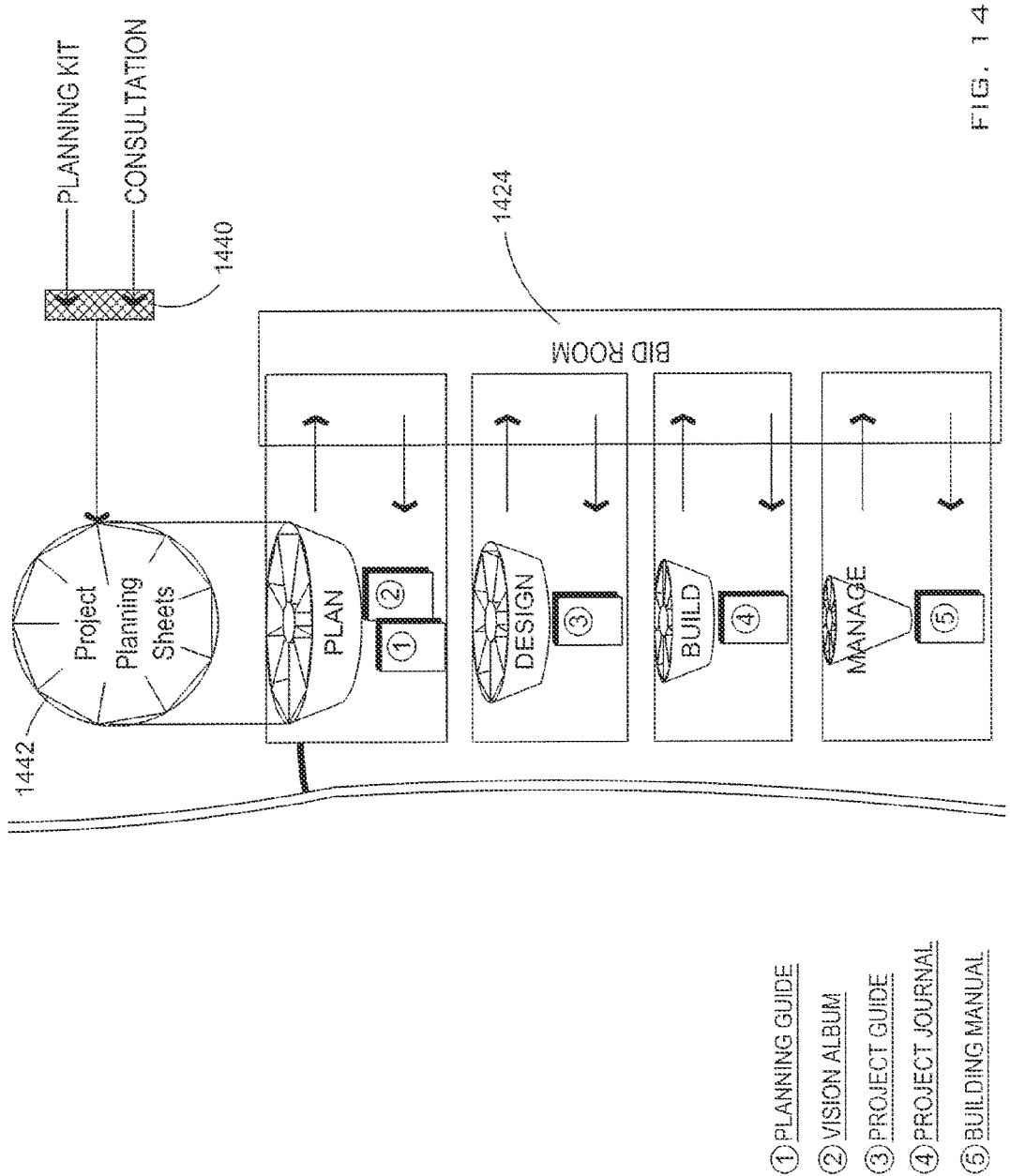

FIG. 15B

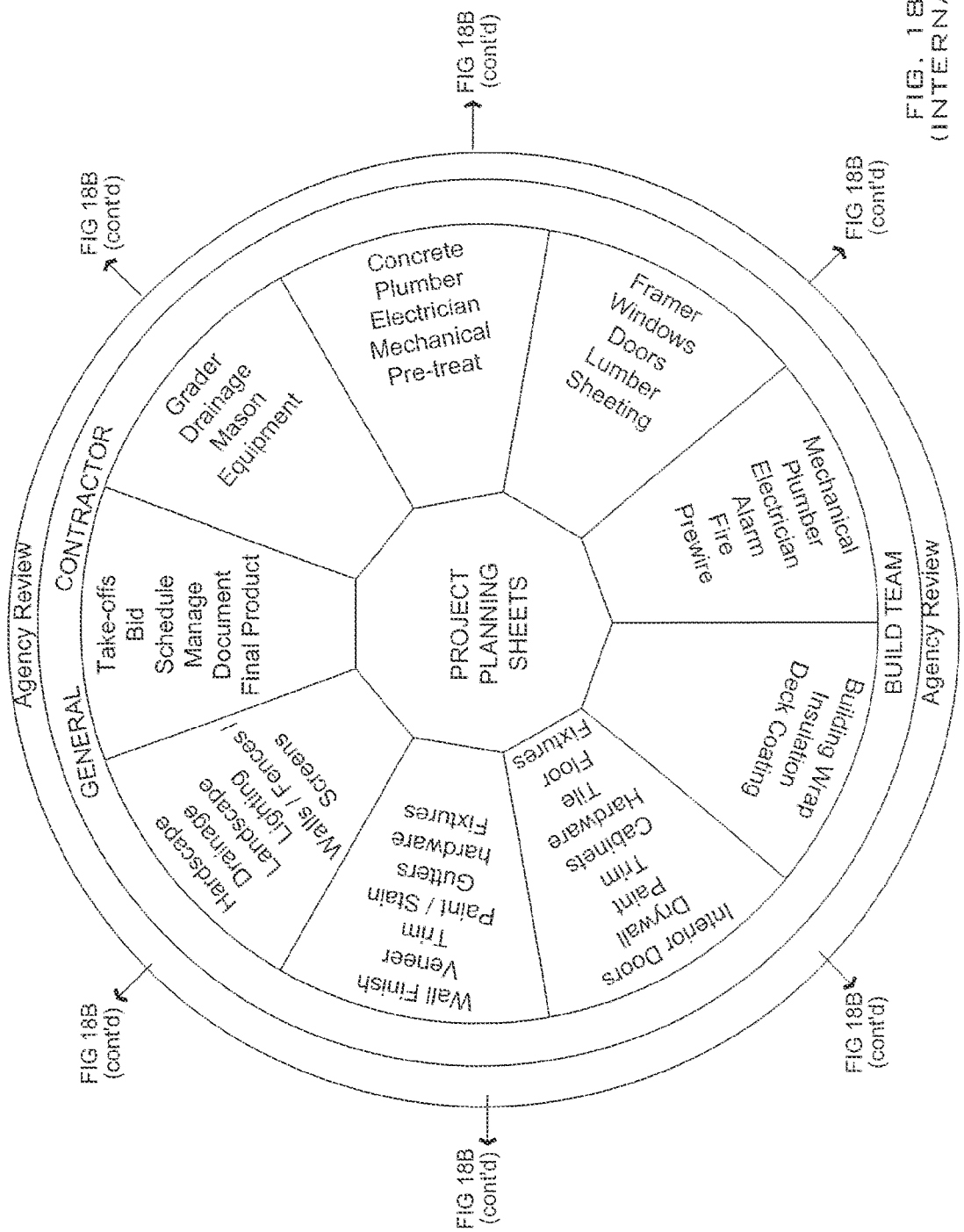
FIG. 18B (INTERNAL)

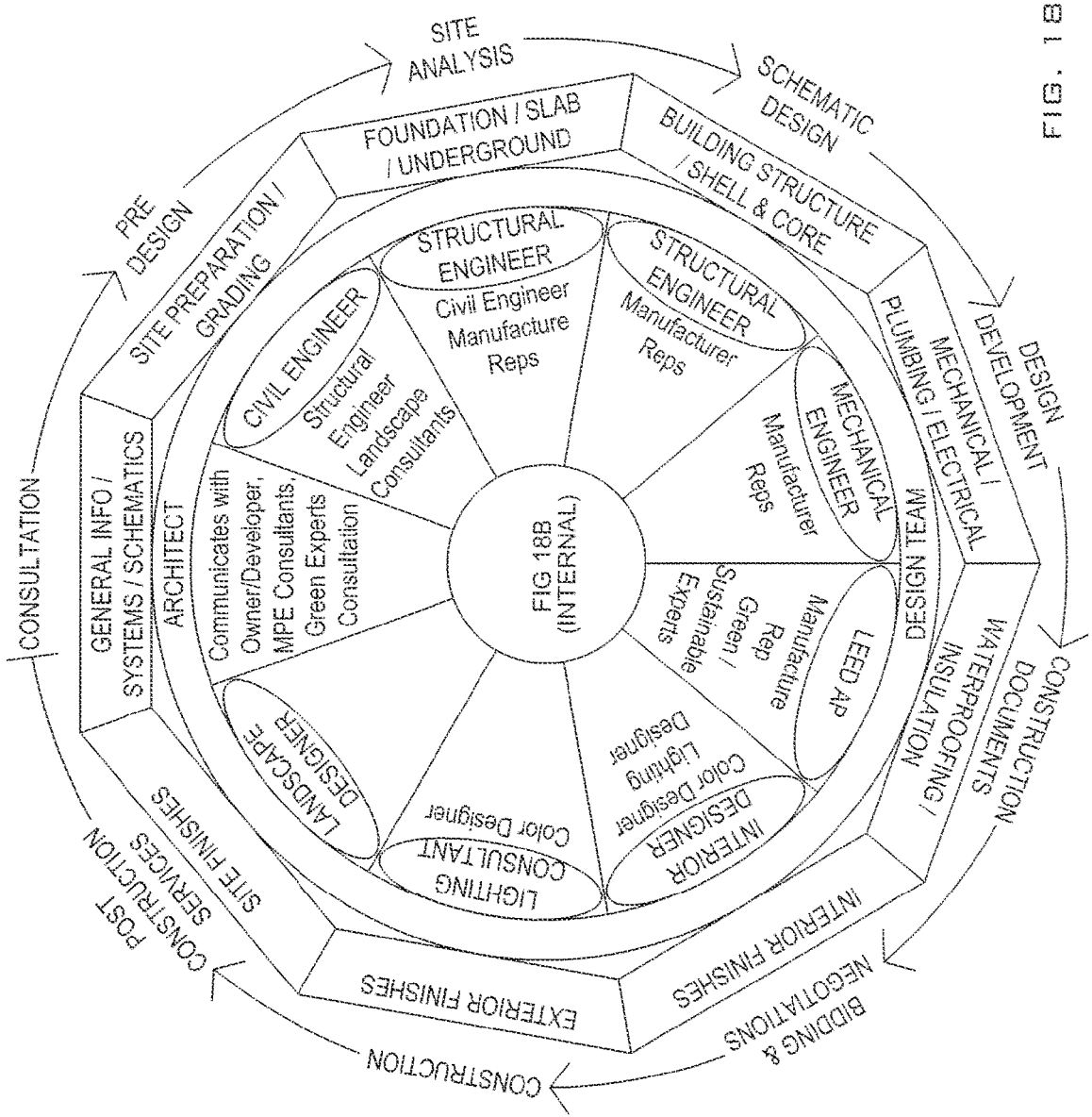

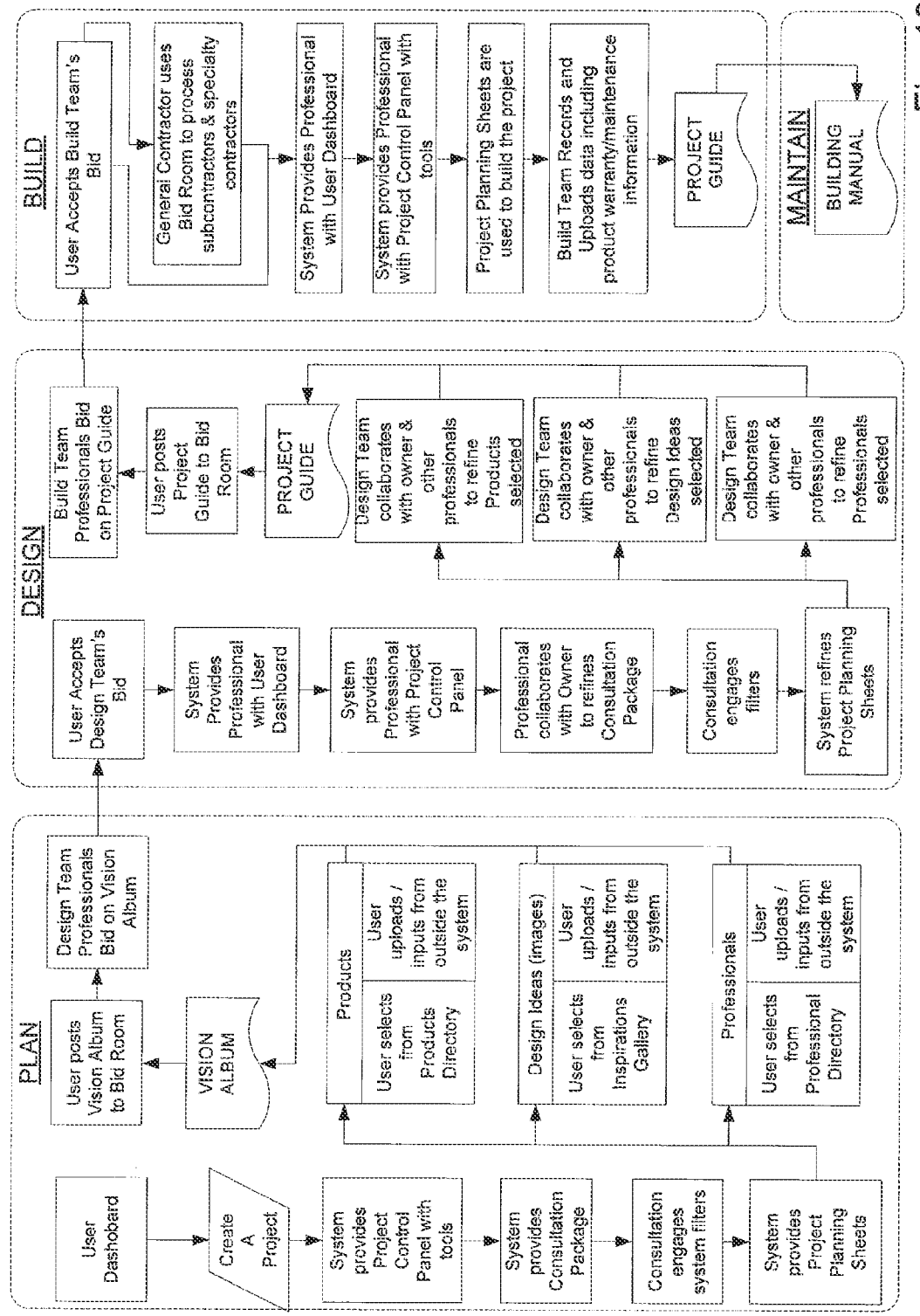

PROJECT PLANNING SYSTEM

This application is a continuation of co-pending U.S. application Ser. No. 14/985,280, filed Dec. 30, 205, which is a continuation of U.S. application Ser. No. 12/690,026, filed Jan. 19, 2010; which is a non-provisional application that claims priority to the U.S. provisional application Ser. No. 61/145,503, filed Jan. 16, 2009, and to the U.S. provisional application Ser. No. 61/177,961, filed May 13, 2009, the contents of all of which are expressly incorporated herein by reference for all purposes.

BACKGROUND

Field of Art

The present invention is directed to a project planning system, and particularly to a system for creating, designing and implementing a custom project and solving technical difficulties that are involved therewith, and more particularly to a system for teaching and managing building construction, customization, documentation, collaboration, and communication as well as project planning for other everyday jobs, functions, and activities.

Related Art

Most consumers begin a project without a plan. However, the more informed a person or a group is when conceptualizing an idea, the better are the chances of completing a successful project related to that idea. Generally, the problem with most project planning is that there is either too much or not enough information available; there are many decisions to be made, and many opinions and options to be researched. Generally, the standard practice is to venture to a research library, a book store or the World Wide Web (www) and search for information. Typically, the participants are overwhelmed with randomly presented data. One potential solution is to hire an expert to help limit the selections. Experts also have many different opinions and answers on how to do the same task. The consumer generally goes forward with a weak map of the process. This may lead to cost overruns, time delays, unnecessary and unfortunate surprises and the like.

When developing a project in the construction industry, for example, to provide options to a customer or developer of any building project, an architect, a consultant or a general contractor might provide lists of product specifications, numerous OEMs, trade contractors, and suppliers that the customer may use to choose from a very large number of options. The selection process and management requirements of the owner, design team and general contractor increase due to the large number of options made available, the large number of selections that need to be tracked, and the large amount of required documentation that accompanies the project. Generally, property owners and developers have too few tools available to them to help with getting their construction projects completed. The process is fragmented, and sources including the www and trade publications are often incomplete, misleading, not well organized and unreliable. Thus, a potentially complex question or problem for getting a project appropriately planned or implemented may never receive a technical answer or solution that it requires.

Generally, when developing a project plan including various service related industries, customers or consumers of most services are provided with lists of products, options, available information, tips, resources, vendors and the like that the customer or consumer might use to make selections regarding the particular service. The selection process and complexity associated with managing the selection process increase due to the large number of options that may be made available to the consumer. Typically, a large number of selections may need to be tracked in order to preserve the consumer's general desires. Even though consumers may be inundated with large amounts of information, options and the like, the consumer still may not receive sufficient information or other data that is actually related to his or her specific desires, wants and needs. In some instances, the consumer may not even be aware that certain options even exist.

SUMMARY

Embodiments of the present disclosure have several features, no single one of which is solely responsible for their desirable attributes. Without limiting the scope of the present embodiments as expressed by the claims that follow, their more prominent features will now be discussed.

The project planning system provides a step-by-step project development process and resolves technical difficulties required to successfully plan and implement the project. The planning begins with development of a Vision Album, Planning Guide, or report created by the system for a user interested in creating a custom project. The Vision Album may include all of the parameters, guidelines, product and service selections that the user has selected and that represent the user's desires and wants for the project. As further discussed below, the project can be any number of types and in any number of fields. For example, the project can be a building project, a travel project, a career planning project, a camping trip project, a retirement planning project, a research project, and projects related to formulating a political agenda/item, a military campaign, a security implementation plan, a film or TV show, an advertising campaign, a marketing campaign, a business development plan, a Medicare program, a long term health care plan, or considering options for immediate medical care/attention. The project may also be related to education and or career planning including reviewing options, understanding aptitude and or user interests relating to selecting a specific career and the like. The project may include an approach taken by any group, agency or organization to promote and build a workable system. For example, the Homeland Security department, where many agencies benefit by having access to aggregated and organized real time data that is generally blocked at the borders of the different agencies. The agencies would have access to data that allows them to work towards the same goals while knowing what the other agencies are doing. In military campaigns individual goals focus on one outcome or another, where solutions could be made part of the main objective where all parties are represented, and information is readily available, including historical information, best practices and considerations made during the planning phase but before execution of the plan.

A Project Guide is developed by the system to include the interactive collaboration between a user and a project developer and a design team and includes specifications for the project to be developed or constructed. A Project Journal is compiled by the system to include information from a facilitator or build team relating to the build team's actions taken to implement the custom project in accordance with the requirements as set forth in the Planning Guide/Vision Album and as refined in the Project Guide. Depending on the projects to be planned, the build team may be referred to as a counselor, a facilitator, a trainer, coach and the like. A Project Portfolio/Building Manual is a compilation of the information related to the custom project and obtained through inputs from the user, the design team members, and the build team members. The Project Portfolio, also referred to as the Building Manual, may also include but is not limited to, a collection of tools and databases, which may include selectable photos and graphic images, materials, products, systems, communications and permit data as well as installer maintenance recommendations and requirements/schedules and warranty information. The Project Portfolio may also include information useful to a user even after a project has been completed. Professional service providers may be included, who may be selected to perform the required work, along with samples, ideas, suggestions, and the like, that facilitate thorough and exhaustive reviews of each and every aspect/phase of the conception, design and implementation of the custom project.

Input and queries are not limited to only the user, the design team or the build team, the planning system supports communication and collaboration between all project participants and or industry stakeholders invited to the collaboration at any phase in the development of the project. Thus, collaboration may include social/business networking, such as by and between friends and family members regarding a project, communication between Industry Professionals, Manufacturers and Suppliers. A system sector section described below supports industry collaboration by way of Blogs, Forums, Committees and the like. The project collaboration supports complete communication and collaboration between all project participants including any person or group who are invited to participate in the project. The planning system may assign the user(s) with a project email address so all communications between participants go in and out of the system so that the communications on a project may be saved.

In one aspect, a computer program product is provided for managing projects. The computer program product may include a computer useable medium having computer readable instructions embodied therein for generating a project planning document. The computer readable instructions when executed on a computer cause the computer to: generate a first report that includes parameters, guidelines, product selections and service selections relating to a project selected by a first user; generate a second report that includes modifications to at least one of the parameters, guidelines, product selections, and service selections relating to the project based on input by a second user; and generate a third report that journals actions to be taken in implementing the project using the parameters, guidelines, product selection and service selection set forth in the first report and as modified in the second report.

In another aspect, a computer implemented system is provided including a network interface circuitry configured to receive data and transmit data over a network; and at least one data processor coupled to the network interface circuitry and configured by executable instructions to generate a project planning document. The executable instructions including executable instructions for: receiving an input including user selections relating to a project type, the input provided by a first user; generating a first guide including a first set of data compiled based on designated preferences defined in the user selections; generating a second guide including a second set of data including at least a portion of the first set of data modified by a second user; and generating a third guide recording the actions taken in implementing a project plan based on at least portions of the first and second sets of data. The computer-implemented system may further include program instructions for: assembling the first, second and third guides into a final guide.

In yet another aspect, a computer-implemented method is provided for generating a planning document including receiving an input from a first user that includes user selections relating to a project type; generating planning sheets related to the project type and populating segments of the planning sheets with a first set of data categorized based on the user selections; granting access to the planning sheets to a second user and allowing the second user to modify at least a portion of the first set of data to create a second set of data in the segments of the planning sheets; and granting access to the planning sheets to a third user and allowing the third user to journal the actions to be taken in implementing a project based on at least portions of the first and second sets of data in the planning sheets.

In yet another aspect, a computer-implemented method is provided for generating a project planning document including presenting queries prompting responses relating to a project type, the responses provided by a first user in generating a first set of data; filtering the first set of data and populating segments of a planning sheet with the filtered first set of data based on project preferences defined in the responses to the queries, the filtered first set of data included in a planning guide; modifying the first set of data in the planning guide in response to interactive and collaborative queries made between the first user and a second user to create a project guide having a second set of data; and recording progress of an implementation by a third user of the project guide to create a project journal, said project journal comprising actions to be taken in implementing a project based on at least portions of the first and second sets of data in the planning sheets.

In yet another aspect, a computer implemented method is provided for generating a project planning document including: presenting queries relating to a project type to prompt first inputs from a first user; filtering the first inputs to populate segments of an initial planning sheet representing an initial planning path with the filtered first inputs, the filtering based on user selections from the first user provided in response to the initial queries to create an initial project plan; presenting a plurality of additional queries based on the filtered first inputs to prompt a plurality of secondary inputs; filtering the plurality of secondary inputs to populate segments of an alternative planning sheet representing an alternative planning path with filtered secondary inputs, the filtering based on user selections from the first user provided in response to the plurality of additional queries, wherein an alternative project plan is produced from the alternative planning path, which is different from the initial project plan, and creating a first guide that includes the alternative project plan; modifying the alternative project plan in response to interactive and collaborative queries made between the first user and a second user to produce a modified alternative project plan, and creating a second guide that includes the modified alternative project plan; recording actions taken and the progress being made in implementing the modified alternative project plan in a third guide; and generating a project planning document including at least the information included in the first guide, the second guide and the third guide.

In yet another aspect, a computer program product is provided for managing projects. The computer program product including a computer useable medium having a computer readable program. The computer readable program when executed on a computer causes the computer to: receive an input including user selections relating to a project type provided by a first user; generate planning sheets related to the project type and populating segments of the planning sheets with a first set of data categorized based on the user selections; grant access to the planning sheets to a second user and allowing the second user to modify at least a portion of the first set of data to create a second set of data in the segments of the planning sheets; and record actions taken by a third user in implementing a project based on at least portions of the first and second sets of data in the planning sheets.

In yet another aspect, a computer-implemented system is provided including network interface circuitry configured to receive data and transmit data over a network; and at least one data processor coupled to the network interface circuitry and configured by executable instructions to generate a project planning document based on received data. The executable instructions including executable instructions for: presenting queries prompting responses relating to a project of a project type, the responses provided by a first user; populating segments of a planning sheet with the data filtered based on project preferences defined in the responses to the queries, the filtered data included in a planning guide; modifying the filtered data in the planning guide in response to interactive and collaborative queries and responses made between the first user and a second user, the modified filtered data included in a project guide; and recording the progress of an implementation by a third user of the filtered data and modified filtered data to create a project journal.

This brief summary has been provided so that the nature of the embodiments may be understood quickly. A more complete understanding may be obtained by reference to the following detailed description of the embodiments along with the attached drawings.

BRIEF DESCRIPTION OF THE DRAWINGS

Embodiments of the present disclosure will now be discussed in detail with an emphasis on advantageous features thereof. These embodiments depict the novel and non-obvious aspects of the disclosure shown in the accompanying drawings, which are for illustrative purposes only. These drawings include the following figures, in which like numerals indicate like parts:

FIGS. 12A and 12B are screenshots illustrating features of the design center according to an embodiment;

FIGS. 13A and 13B are screenshots illustrating features of a graphical user interface for the planning system according to an embodiment;

FIG. 14B is a diagram illustrating the building system of FIG. 14A as a component of the overall planning system and FIG. 14C is a cost, time, and quality filter usable with the system;

FIG. 15B is a screenshot illustrating features of a graphical user interface for the professionals profile/showcase listings according to an embodiment;

FIGS. 18A and 18B are diagrams illustrating a view of plan, management, information, organization and communication segments involved in using the planning system in accordance with an embodiment; and FIG. 19 is a flow diagram illustrating an exemplary implementation of the planning system in accordance with an embodiment of the disclosure.

DETAILED DESCRIPTION

Figure 1:
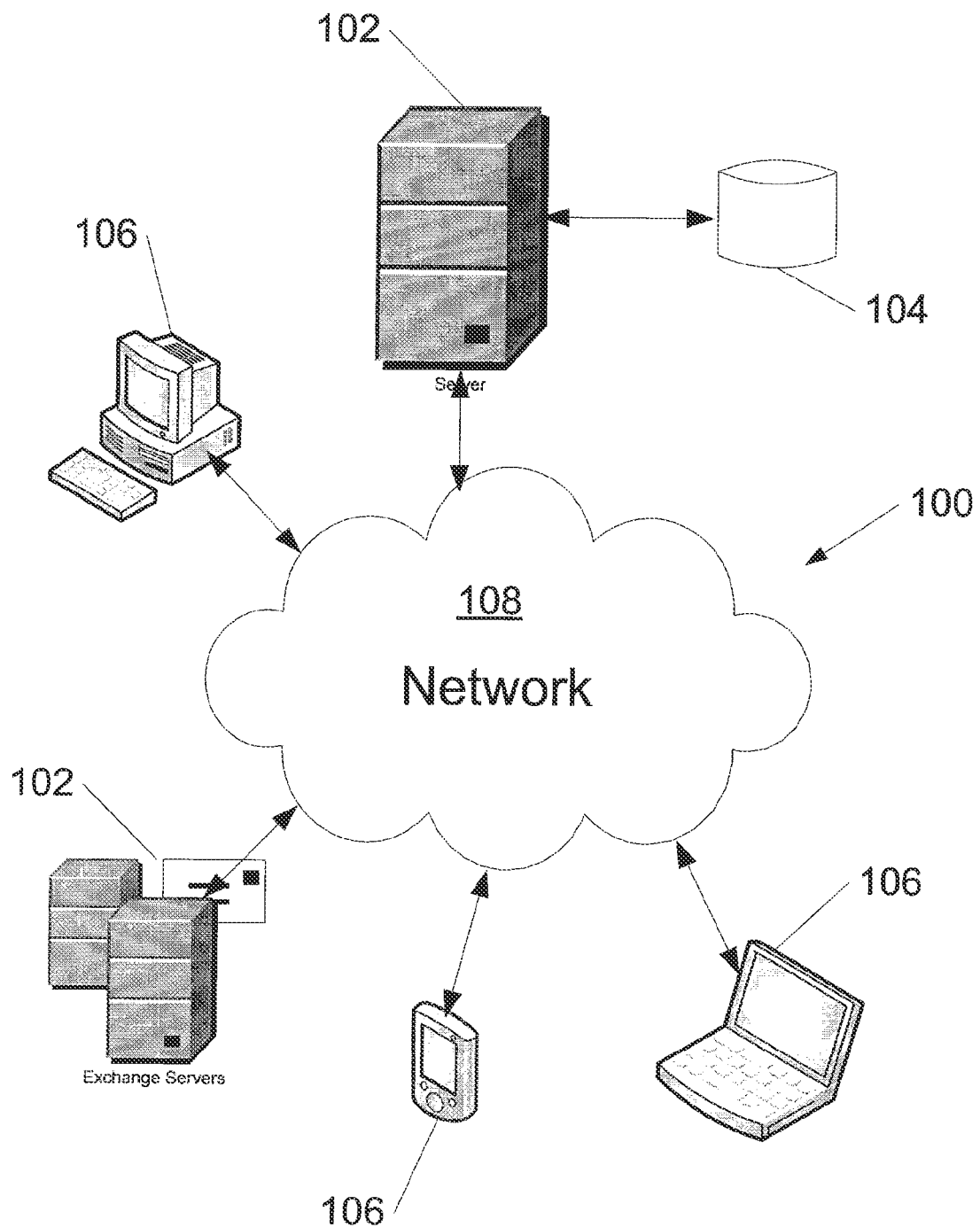
FIG. 1 is a schematic diagram of an exemplary computing system for implementing the embodiments of the present disclosure.

The detailed description set forth below in connection with the appended drawings is intended as a description of exemplary embodiments of a planning system. The planning system of the present disclosure may be used as a mechanism to create a planning document related to various project-planning uses. The technical problem relates to the present inability in the art to be able to create a planning document that does not require the user to search volume upon volume of data in various sources in an attempt to capture pertinent information related to the project. The technical problem is solved as described below, by providing a planning system that includes technical features that allow a user's wants, needs and desires to be quickly and efficiently coordinated in an interactive and collaborative effort with others to create the planning document that has the benefit of input from experts, pundits, and other users. Due to the collaborative and interactive nature of the planning system, the creation of the planning document is done faster, more efficient, and resolves more technical problems and issues than originally realized. The planning document provides a single document that moves forward in the planning system while being accessed and refined with potential input from participants and stakeholders related to the project with information that is aggregated and organized in the planning document.

In one embodiment, the planning system is described as a building system that outputs a series of guides or reports that include various forms of data related to the conception, design and construction phases for creating a building structure (the building system). In other embodiments, the planning system is described in more general terms, using other examples, as a project planning system that outputs a series of guides or reports which include various forms of data related to the conception, design and implementation phases for creating a custom project involving numerous other industries (the project system). The descriptions set forth the technical features involved in, and the steps for using the planning system in connection with the illustrated embodiments. It is to be understood that the same or equivalent functions and structures may be accomplished by different embodiments, which are intended to be encompassed within the spirit and scope of the present disclosure, especially those incorporating a combination of technical features shown in the different embodiments included herein.

Many of the functions and technical features described in this specification have been labeled as modules, steps, processes or a similar designation, in order to emphasize their implementation independence. Modules may be implemented in software for execution by various types of processors. An identified module of executable code may include one or more physical or logical blocks of computer instructions, which may be organized as an object, procedure, or function. The executables of an identified module need not be physically located together, but may include instructions stored in different locations which, when joined logically together, comprise the module and achieve the stated purpose for the module. A module of executable codes may be a single instruction, or many instructions, and may even be distributed over several different code segments, among different programs, and across several memory devices. Similarly, operational data may be identified and illustrated herein within one or more modules, and may be embodied in any suitable form and organized within any suitable type of data structure. The operational data may be collected as a single data set, or may be distributed over different locations including over different storage devices, and may exist, at least partially, merely as electronic signals on a system or network.

FIG. 1 is a schematic block diagram illustrating one embodiment of a computing system 100 for executing the adaptive technical features of the present disclosure described below in detail. In one exemplary embodiment, the computing system 100 may include a server 102 or network of exchange servers 102 in communication with a database 104, and one or more server clients, workstations, mobile devices, laptops 106 connected to the server 102 through a data network 108. The data network 106 includes a Local Area Network (LAN), or alternatively, may include a wireless LAN, a Wide Area Network (WAN), the internet, and the like. In one embodiment, the server 102 may include a software application that remains on the server 102 where the clients use a web browser to interact with the software application.

The server 102 may provide application services, web services, mail services, data storage services, and communication services, used to support operations of the adaptive embodiments. The server 102 may host an apparatus, software application, or the like to perform the operations of the disclosed embodiments. In one embodiment, a single server 102 may provide some or all of theses services, or a plurality of servers 102 may be used to provide these services. The database 104 stores data for use by the server 102. The database 104 may be remote to the server 102, or may reside on the server 102. The database 104 may include a storage controller, data storage devices such as magnetic, solid state, or optical storage disks, data input/output (I/O) controls, and the like as are well known in the art.

In one embodiment, the planning system may be provided in the form of a computer program product for managing projects and resolving technical issues related to the projects. The computer program product may include a computer useable medium having a computer readable program, where the computer readable program when executed on a computer causes the computer to perform various steps. In another embodiment, network interface circuitry is provided and configured to receive data and transmit data over a network. At least one data processor is coupled to the network interface circuitry and configured by program instructions to generate a project planning document based on received data into the planning system. The data processor may also command transmissions of at least a part of the project planning document over the network.

Figure 15A:
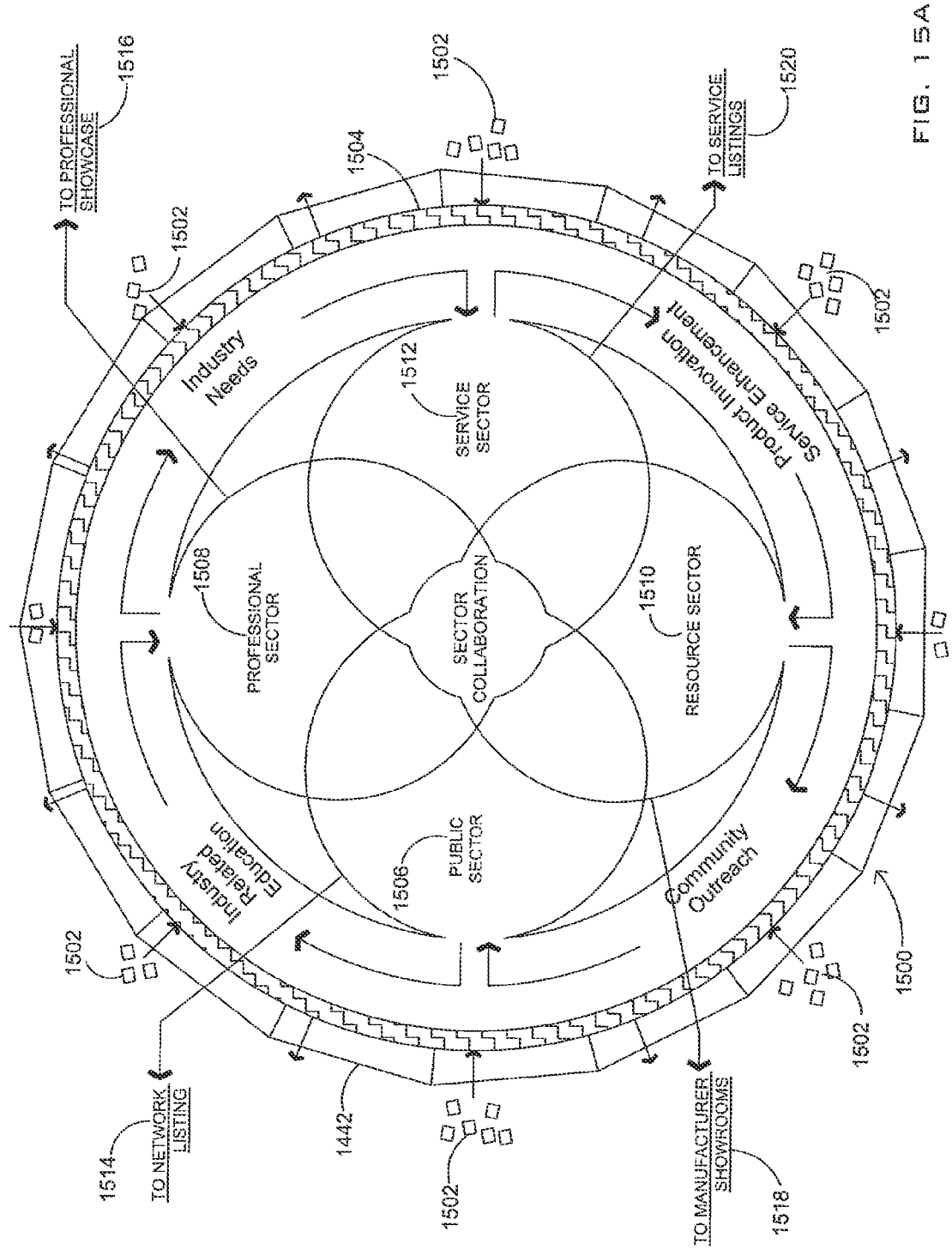
FIG. 15A is a is a graphical illustration representing the interaction between the planning system and information providers according to an embodiment.
Figure 15B:
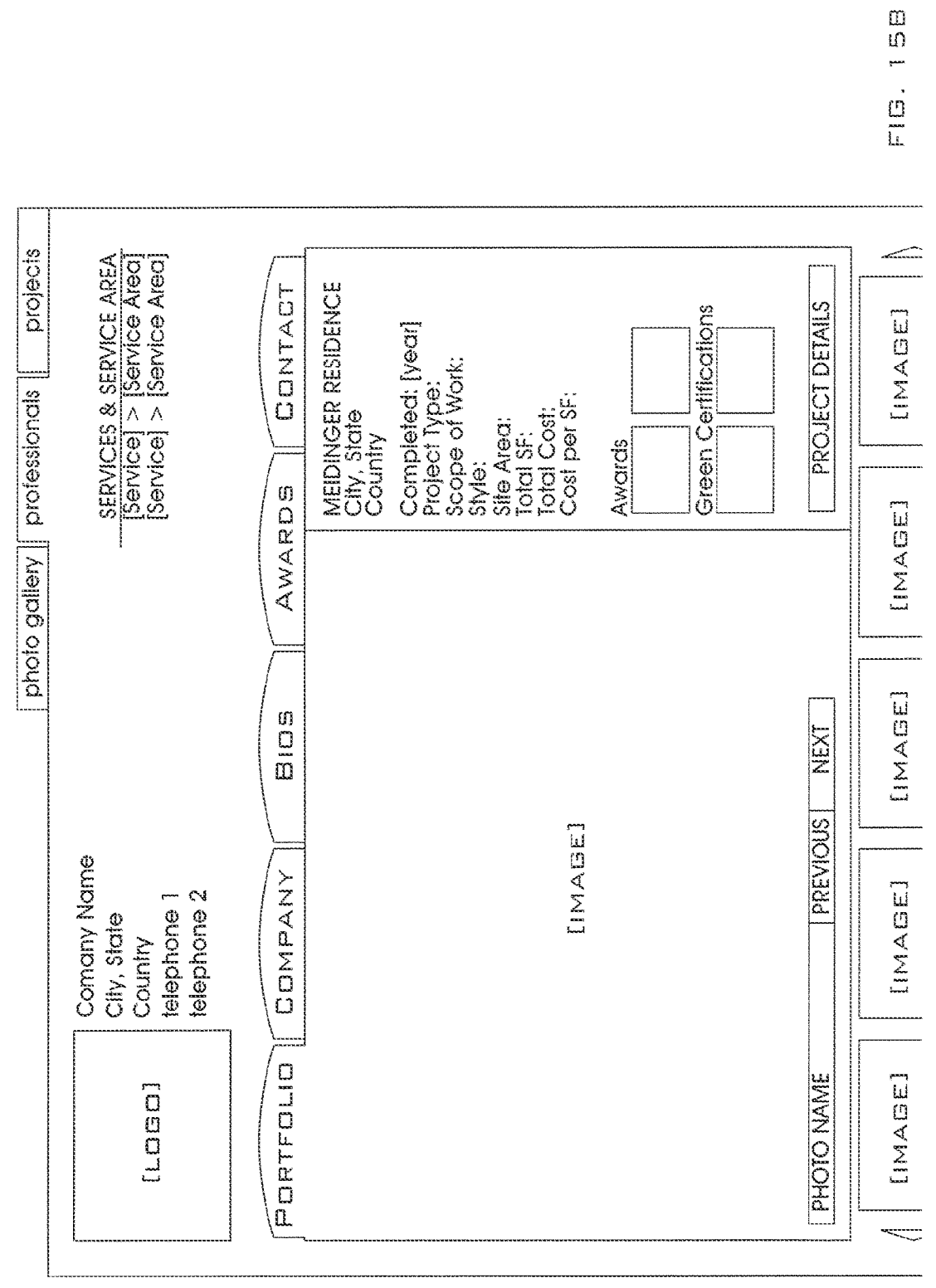

In one embodiment, the planning system is initially populated with data and information that enters the planning system either by request or by grant of permission. As illustrated in FIG. 15A, the data and information is placed in an appropriate sector collaboration module 1500 to be made available to users of the planning system to aid in the conception and design of the projects. Generally, in one embodiment, the data and information 1502 is delivered to the system in a preformatted template, for example as shown in FIG. 15B, that provides a means to the information provider to organize all of the information that it has available or desires to share with the users of the planning system who desire to access and use the information.

As shown in FIG. 15A, information sources may be any source that can contribute and benefit any project, such as by providing input that solves a problem or suggests a different alternative that results in a time savings, a cost savings, a better quality project, and the like. Generally, the data and information 1502 may fall into certain sectors, which include, but are not limited to, for example the Public Sector 1506, the Professional Sector 1508, the Resource Sector 1510 and the Service Sector 1512. As shown in the sector collaboration diagram 1500 of FIG. 15A, the data and information 1502 enters the planning system through a data filter 1504. The data filter 1504 organizes, aggregates, codes and delivers the data and information 1502 for proper placement under the appropriate sector locations on the system. The proper placement of the data and information facilitates later use of the data and information in a project. Other sectors may also come into the sector collaboration component of the system.

The data and information 1502 may be coded to facilitate the searching process. The information and data may be made accessible through a link, such as, but not limited to, a designated network listing 1514, a professional showcase 1516, a manufacturer showcase 1518, and a service listing 1520 that reside on the planning system. In one embodiment, the information provided by the outside information providers is transferred via the data filter 1504 to the appropriate action modules residing on the planning system. As described below, the data and information is placed in, for example, an Inspiration Gallery, a Design Center or other action modules, which maintain searchable photos, images, drawings, renderings schematics, and the like, and which maintain the information regarding the professionals who provide the services and products being profiled.

In one embodiment, the Public Sector 1506 may include, but is not limited to, for example groups whose services are related to the interaction between a consumer and public entities. These groups may include: a) Trade Groups, which may provide a link between the manufacturers, the industry professionals and the consumers; b) Non Profits, which may provide links to information and education and industry best practices; c) Government Agencies, which may provide links to building codes, restrictions and agency review processing requirements; d) Utility Companies, which may provide tips on how to save energy savings; e) Continuing Education Sources, which may link to schedules of events that are geared toward serving industry professionals; f) Unions; and g) Universities. Because of the interaction between the public sector participants, the planning system promotes bipartisan participation that results in better project outcomes.

Industry professionals may come on to the planning system and provide information which showcases their respective services, including company information, personal biographies, photos from their project portfolios, awards, accreditations and the like. In the context of planning a construction related project, the Professional Sector 1508 may include, for example, Land Planners, Architects, Engineers, Designers, Landscape Architects and Designers, Lighting designers, Green and Sustainability Experts, Construction Managers, General Contractors, Sub Contractors, Specialty Contractors, Property Managers and Maintenance Crews. The Industry Professionals may be identified and categorized by past work/projects, profession/trade, location, specialty, license, bond, accreditations and the like on the planning system and may be listed in a directory type format for ease of use.

In the Resource Sector 1510, manufacturers and the like, may include details about their capabilities, prices, availability for projects and the attributes of their products. The Service Sector 1512 may include information related to financing, lending, insurance and the like, and include Bankers and Financial Institutions, Insurance Brokers and Carriers, Real Estate Service Providers, Appraisers, Pest Control providers, Specialty Service providers, Marketing Services, Property Managers, Maintenance Service providers and the like.

In one embodiment, the groups represented in the sector collaboration diagram 1500 may form a network that can interact, collaborate and discuss topics of interest to the groups. For example, the sector groups may discuss industry needs or share ideas related to innovations advancing their respective industries. The sector groups may conduct forums and may form committees created to incubate ideas that are beneficial to the entire network of sector groups. The interaction between the sector groups may take place on blogs or via a similar communication means. Collaboration between the different groups advances the art by bringing the overall knowledge of the different groups to a higher shared level. Thus, the groups may be able to solve problems or issues for a particular project in a different way that otherwise would not be available without the facilitation provided by the present methods, systems, and apparatuses. In most industries and in most cases each occurrence of a project begins from scratch. The lessons learned and the experiences from past projects are not necessarily passed to the next person or group who embark on the same or similar project type. By using the planning system, the lessons and the experiences may be shared, saved, organized and made retrievable when needed by anyone who comes into the process or has the need to proceed in any complex process/project. Once solutions are tested and perfected they may become industry standards. In most cases, the level of understanding, knowledge and excellence made towards achieving a certain task is elevated resulting in better project outcomes.

Upon entering the planning system, the user is able to search and view any desired information in the system related to the information that has been provided by the information providers.

Generally, a user of the planning system begins by providing information into a system interface, which may be referred to as a Planning Kit or a Consultation package. The Planning Kit may request, query or prompt the user for information regarding project type and other demographic information, which then leads to additional requests or prompts that are appropriate to the specific project identified by the user. In one embodiment, the Cost, Time, Quality may be specified by a user. The user may specify any one of the criteria and view products, systems or data related to the one or more criteria (Cost, Time, Quality). The user may also relate any two or three of the criteria in degree of importance to a project to help them refine the project as it relates to these factors (see FIG. 14C). The information provided by the user is used to create Planning Sheets. Each project has a set of Planning Sheets created which identify a complete list of tasks and requirements necessary to complete a designated project type. In the Planning Sheets, the tasks, components and requirements are broken down into segments of various categories and subcategories. While being created for a specific project, the Planning Sheets are populated with the data and information provided by the information providers that are relevant to or skilled in a particular project type. The Planning Sheets also store and record the user selections of information from the action modules described below. The Planning Sheets provide a means by which the user and other collaborators may continuously populate or edit the Planning Sheets to provide additional details and refinements related to the project, as the project progresses from conception to implementation. Thus, the Planning Sheets represent the framework of the project, which extends through each phase or the life of the project. In addition, the Planning Sheets provide access to the information by all users, which promotes collaboration between project participants and others, who may access, revise, modify and input additional data during all phases of a project as described below.

After the user has interfaced with the Planning Kit and the Planning Sheets are created, the user may access action modules, such as the Inspirations Gallery, the Project Profiles, and other Professional Showcases, where the user may find information, products and professional services that facilitate the project and define the anticipated work. As mentioned above, the Planning Sheets are populated with the data provided by the user and others. Each user has access to a System Dashboard and Project Control Panel. The System Dashboard provides access to system tools. The Project Control Panel provides access to project specific data. In one embodiment, this interactive effort when finalized produces the Vision Album, also referred to as the Planning Guide or Planning Report, which is a high level review of the project that identifies the project parameters and guidelines, service selections and product selections as recorded and stored in the Planning Sheets.

The user may then interact and collaborate with an individual or team dedicated to helping create or design the project. The design team is granted access to the project via the Vision Album to allow for an interactive collaboration that allows the user and the design team to create a Project Guide, which may also be referred to as the Project Report. The Project Guide includes the selections made and set forth in the Planning Guide as well as the revisions, changes, modifications, and deletions, made in communication, interaction and collaboration with the design team to refine the selections on an iterative basis and make the selections final. Once the interactive collaboration with the design team generates final selections, the design team provides the plans, specifications and other details that allow one to actually implement or build the project based on the final selections. The final selections, specifications, plans and the like are incorporated into the Project Guide upon approval from the user.

After selections are made, access to the project may be granted to a build team that implements or constructs the project. The build team remains in contact with both the user and design team via the planning sheets throughout the implementation process, as changes and modifications may still be made by the build team during the building phase. In one embodiment, the build team has access to customized work orders that are formatted for each trade and or installation. Each required product for a specific installation may be listed on the work orders. This helps project participants from wasting time picking up or ordering materials, that are sometimes forgotten. Each product on the work orders may be linked to a calculator built into the form. The user may enter the size/area or other pertinent information and the calculator automatically calculates the quantity/size of each item. For example, a user desires to order drywall for an installation. The user may access the work order and use the calculator to help the user identify the number and size of drywall sheets required. The work order may also list nails, screws, glue, tape, mud, sand paper and the tools that are generally required for this type of installation. Once the user enters the wall square footage, the system calculates the number of sheets, it also identifies the quantity of nails, screws, tape, mud and the like needed for the installation. The work orders may be customized by any user to serve its specific needs. All actions taken by the build team are documented, journaled or recorded in the planning sheets to ultimately be assembled in a guide or report referred to as the Project Journal.

The final output of the planning system includes a completed Project Manual or Portfolio that incorporates an assembled compilation of all the information found in each of the guides/reports prepared through use of the planning system. In addition to the information compiled in the project journal, as products and systems are purchased and installed back up data including warranty information and maintenance recommendations and requirements are uploaded into the project data files. All of this information becomes part of the journal records. In some embodiments, a maintenance program becomes part of the Project Manual that is passed along with the completed project. The Project Portfolio/Building Manual as well as each of the other intermediate guides, may be presented on disc, printed in a bound book or presented in a three ring binder form.

Figure 2:
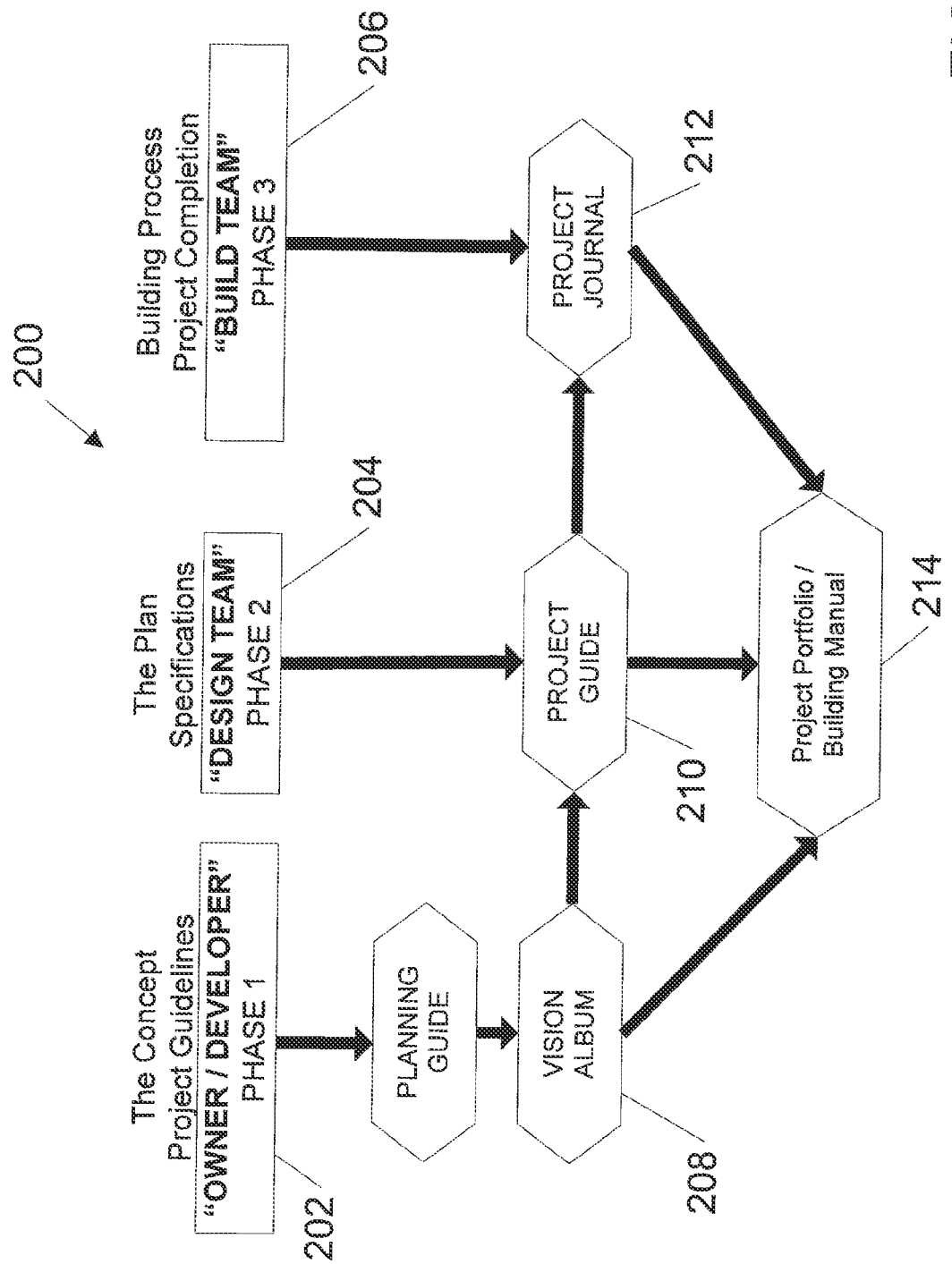
FIG. 2 is a diagram illustrating a building system including a process that allows a User to create a custom building project portfolio in accordance with an embodiment.

FIG. 2 is a diagram illustrating an embodiment for using the planning system as a building system 200 including a process that allows a user to create a custom building project plan from a vague idea or concept in accordance with an embodiment of the present disclosure. The technical features described allow users the ability to design, plan, manage and implement, for example, a building construction project. The process takes input from the user and organizes it into the building system 200 for various other users or user groups to review and refine.

In one embodiment, the building system 200 provides a generally comprehensive site for aspects of the process, such as for: (1) planning (2) design, (3) building, (4) product needs and the like to build a building or renovated structure. The building system 200 may be a web-based, interactive, and collaborative, planning, designing and facilitating tool that connects an owner/developer, architect, builder, subcontractor, suppliers, and other individuals/parties together, on-line from almost any internet connection in the world, to select, plan, and construct or renovate a building or structure. By being broad-based and not limited to a specific geographic location, different tastes, feels, and cultural inputs can be part of the process.

Generally, the building system 200 facilitates the integration of building products and systems into all types of buildings: residential, commercial, industrial, mid-rise, high-rise and the like. As shown in FIG. 2, in one embodiment, the building system 200 divides the design and construction of any building Project into at least three divisions or phases. In one embodiment, the first division or conceptual plan phase includes an Owner/developer 202 (Owner 202), the second division or plan phase includes a Design team 204, and the third division or build phase includes a Build team 206. As described below, the Owner 202, Design team 204 and the Build team 206 form Users or User Groups each of which has certain needs, skills sets and responsibilities in the design and building process as well as responsibilities and obligations to the other User Groups.

The Owner 202 represents the User Group that typically initiates the want or need for the project. The Owner 202 sets parameters and guidelines, such as, but not limited to, budget, building type, project type, occupancy, timeline, and the like, as well as products and services, to describe the overall Vision of the project. The Owner 202 is responsible for communicating or reporting the parameters and guidelines to the Design team 204.

The Design team 204 may include one or many professionals including, but not limited to, Architects, Builders, Contractors, Developers and Engineers, Designers, Draftsman and other professionals, who may be hired by the Owner 202 to design and create the Building Plan and all the necessary specifications needed to get the requisite building permits to construct the Project. The Design team 204 is generally responsible for ensuring that the Building Plan reflects the Vision of the Owner 202. In one embodiment, the building system 200 provides a database-driven project selection menu that allows Professionals to work as a project team no matter where the team members are geographically located. For example, for a given construction project, the Design team may consist of an Architect, a Designer, and a Contractor (collectively, ADC), who may be experts in their respective fields. The ADC may each reside in different areas around the globe. In one embodiment, the building system 200 is accessible via the www; however, alternatively the system may be deployed on local host systems. Using the www, the Design team may, for example, view, select, store, purchase, warehouse and ship products directly to a project site without ever visiting a material supply store or meeting face-to-face. The construction project under the care of the ADC team can view, save, store, modify, specify, and revise any and all aspects of the project, including making changes in building materials, piping, roofing materials, and specifying the use of environmentally friendly products, such as solar panels, recycled materials, and low flow bathroom fixtures and the like.

The Build team 206 may include one or many professionals including, but not limited to, a General Contractor, Soils Engineers, Graders, Framers, Plumbers, Electricians, and other professional tradesman and contractors that may be hired to construct the Project as designed by the Design team 204 while adhering to the rules and regulations of the officiating agencies as well as local planning & building departments or planning commissions. The Build team 206 is responsible to journal all of the actions taken and document all of the products and systems installed that require any type of maintenance or service throughout the life of the building. In this way, anyone who is given the task of maintaining the building may know the product and manufacturer details, which facilitates warranty or repair work. The Build team 206 is further responsible to record or link recommended cleaning products/procedures and frequency of recommended service or maintenance to the Journal and provide to the Owner 202 a quality completed project that reflects the Owner's vision for the project.

The building system 200 allows each User Group to generate guides or reports that are created to document the progress of a User's project from concept, through planning, to final construction in an interactive and innovative process. The guides may be used individually; however, they may be used in conjunction with each other. The guides represent the Output created by the interaction of each User Group with the building system 200, thus each User Group is responsible for creating a specific guide during the project. In one embodiment, the guides include a Vision album 208, which may also be referred to as a Planning guide 208, a Project guide 210 and a Project journal 212. Each guide may constitute a physical compilation of data that may be viewed, printed and delivered to the user or other interested party. Alternatively, the guides may be a virtual (electronic) compilation of data, hosted on the planning system platform for viewing and outputting, or that may be electronically delivered to another party for viewing and subsequent outputting as a printed document.

The Vision album 208 is initially created by the Owner 202. During the concept plan phase (first division), the Owner 202 interacts with various action modules or databases hosted on the planning system. The action modules and databases provide a formatted list of project components for the selected project type, and conceptual design elements, to input, select and clarify the conceptual design elements, including, but not limited to, all parameters, requirements, guidelines, products and services and other initial selections for the project.

The action modules, described below, work as independent modules to allow a User to be able to design, plan, track and build his or her own customized project through a project development module. When used to create a Project, the action modules help to limit the information pertinent to the choices made by the User in order to drive the selection process to creation of a final vision or concept. The Action modules may also include their own set of tools and features.

While creating the Vision album 208, the Owner 202 may access and interact with information provided by various information providers, such as those shown in the graph 1500 of FIG. 15A. As previously mentioned, the information providers may provide information that showcases or highlights their own services and products that are available to the Owner 202, which also helps create the parameters, guidelines, products and services and the other initial selections for the project.

Initially, the information provided by the Owner 202 is divided into the Planning Sheets. The Planning Sheets include information broken down or separated into segments, phases or sections, related to certain steps in the construction process. The sections may be filled, for example, using an intelligent checklist provided to the Owner 202, for example, like the representative checklist shown in FIG. 10. The checklist allows the Owner to enter the project criteria and parameters and guidelines, such as location, type of construction, number of rooms, size, options, colors and the like. The selections may be furthered organized into sets of classes and subclasses for further categorization of the information. As described below, the Planning Sheets provide a means for conveying the Building Plan information through the concept, the plan and the building phases of the construction project for access by all Users and User Groups as the need arises (See FIG. 14A). Only one set of Planning Sheets is issued/used per project. The control and responsibility for recording and documenting into the Planning Sheets is passed along as the project progresses from Plan to Design then Build to Maintain Phases. When the Owner 202 completes and closes his or her Vision Album he or she passes control to the next team who completes and records the design and specifications for the project. The planning sheets are updated as work progresses; thus, everyone is working with the most current set of project information.

The Project guide 210 is created by the Design team 204 upon review of the selections made and set forth in the Vision album 208 by the Owner 202. The Design team 204 communicates, interacts and collaborates with the Owner 202 as well as other consultants and or industry experts to refine on an iterative basis and make final the selections made using the Action modules and databases. The final selections are incorporated into the Project guide 210 upon approval from the Owner 202.

The Project journal 212 is created by the Build team 206 and is used to track the construction and log the processes and progress of the construction project as actions are taken to construct the project. The Project journal 212 may also be used to manage the delivery of labor and materials to the construction site.

The final output of the building system 200 is a completed Project portfolio 214 that is designed as a Users Guide or Building Manual for the project, designed to stay with the project, from owner to owner, or to be used by a manager of, for example, a commercial building to help manage the building after completion. The Project portfolio 214 includes the information that has been generated by the building system 200 for inclusion in each guide. For example, the Vision album 208, the Project guide 210 and the Project journal 212, as well as any other information related to or used in the construction, and that may assist with future maintenance, repairs and renovations, including, but not limited to, all actions taken, all plans, drawings, permits, specifications, engineering calculations, product warranties, service contracts and the like are included in the Project portfolio.

Figure 3:
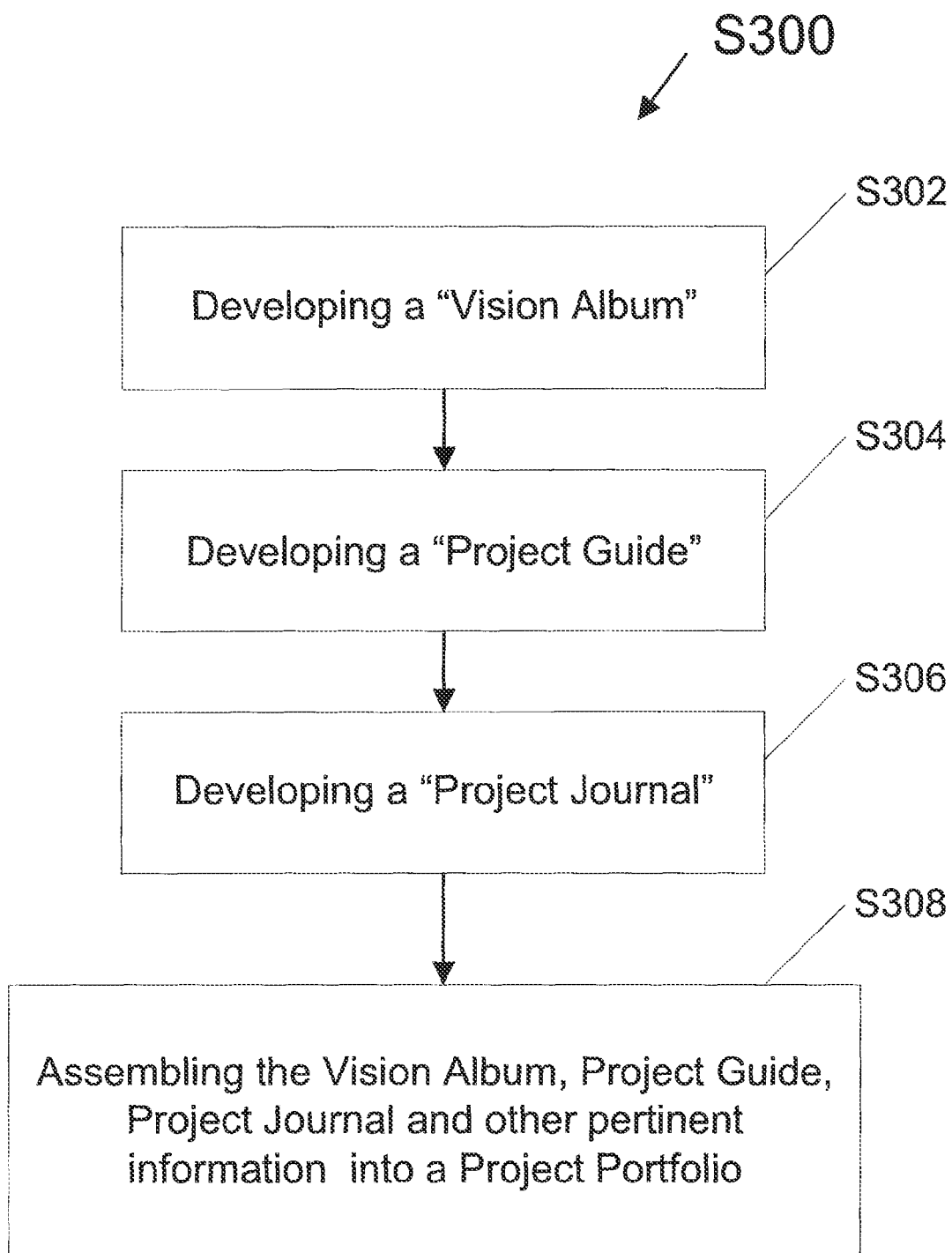
FIG. 3 is a flow diagram illustrating a design and construction process provided by the building system in accordance with an embodiment.

FIG. 3 is a flow diagram illustrating a design and construction process s300 provided by the building system 200 in accordance with an embodiment. With reference now to FIG. 2 in addition to FIG. 3, the design and construction process s300 involves developing the Vision album 208 (s302), developing the Project guide 210 (s304) and developing the Project journal 212 (s306) for a particular project initiated by the Owner 202. Each of the steps in the process (s300) is completed by one of the three User groups 202, 204 and 206, alone or in combination, before being handed off to the next User group for further refinements, modifications, additions, subtractions and implementation.

Once each of the guides has been created, all the guides and other pertinent information are assembled into the completed Project portfolio 214 (s308), which includes the complete package of design and construction documents and information.

Figure 4:
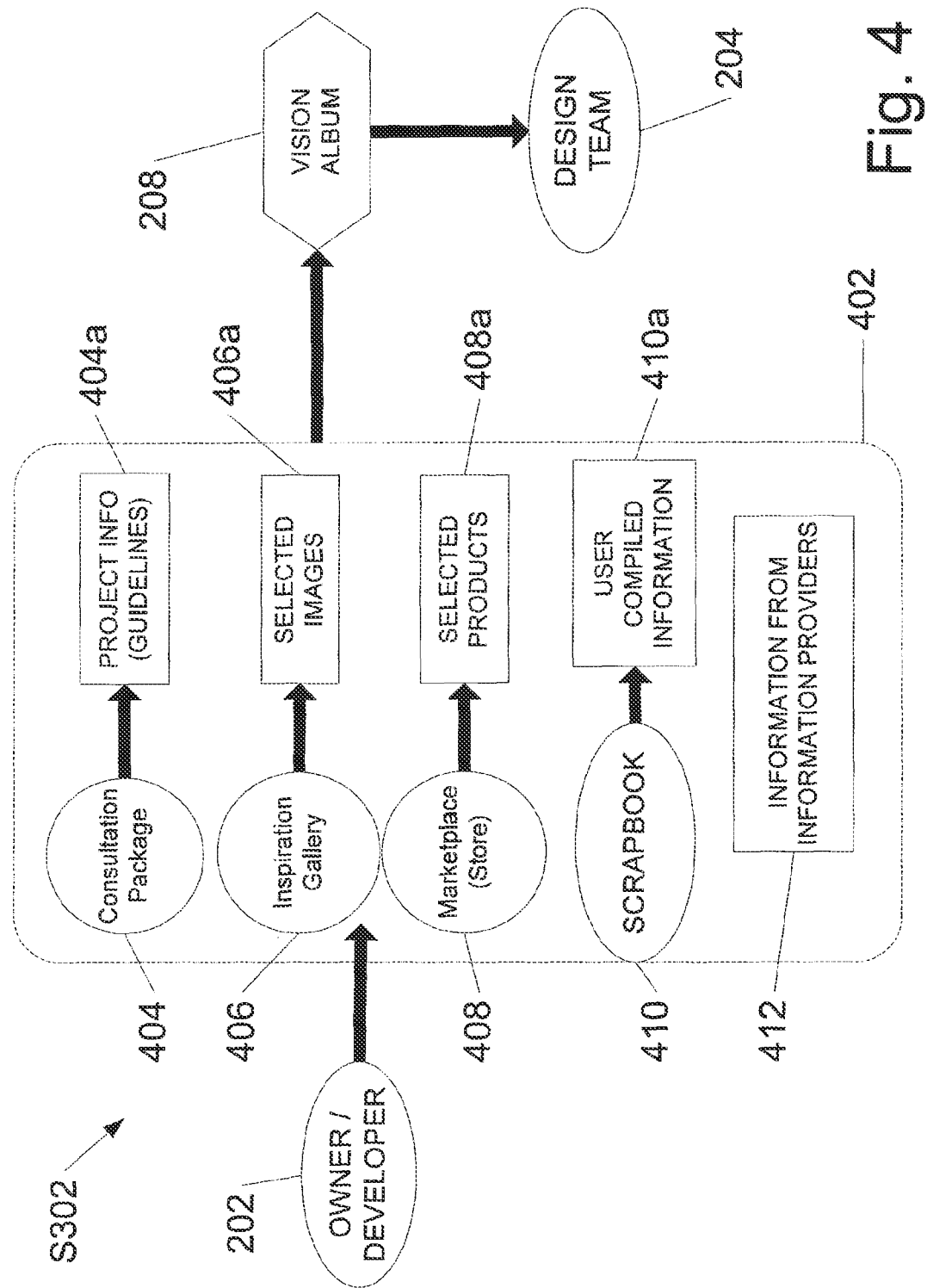
FIG. 4 is a diagram illustrating the creation of a Vision album or Planning guide in accordance with an embodiment.

FIG. 4 is a diagram illustrating the process (s302) of developing the Vision album 208 in accordance with an embodiment. As shown in FIG. 4, the conceptual plan process of the building system 200 includes the development of the Vision album 208 (s302) initiated by the Owner 202. The Owner 202 may be prompted or otherwise provides and specifies the nature and scope of the project. The Owner 202 may access the conceptual design elements module 402, which provides access to the Action modules or databases, which in one embodiment includes a Consultation package 404, an Inspiration gallery 406, a Design center 408 and a Scrapbook 410.

The Consultation package 404 allows the Owner 202 to identify and record the functionality, the look, specific desires and budget constraints up front through using a guided consultation and a visual step-by-step selection process. In one embodiment, the Owner 202 is offered a preformatted online consultation package, which is designed to produce the information that enables the Design team 204 to understand and serve the Owner 202 throughout the process. The consultation package 404 may be formatted, designed and customized for each and every industry project type. For example, the consultation package is different for each project, such as career, education or wedding planning. In the building system 200, the consultation package 404 may be customized for each type of building project, for example, residential, multifamily, commercial, office/retail, industrial, and light/heavy building projects. Once the Owner 202 completes the consultation, a project information file 404a is generated, which includes the selected guidelines.

Figure 11A:
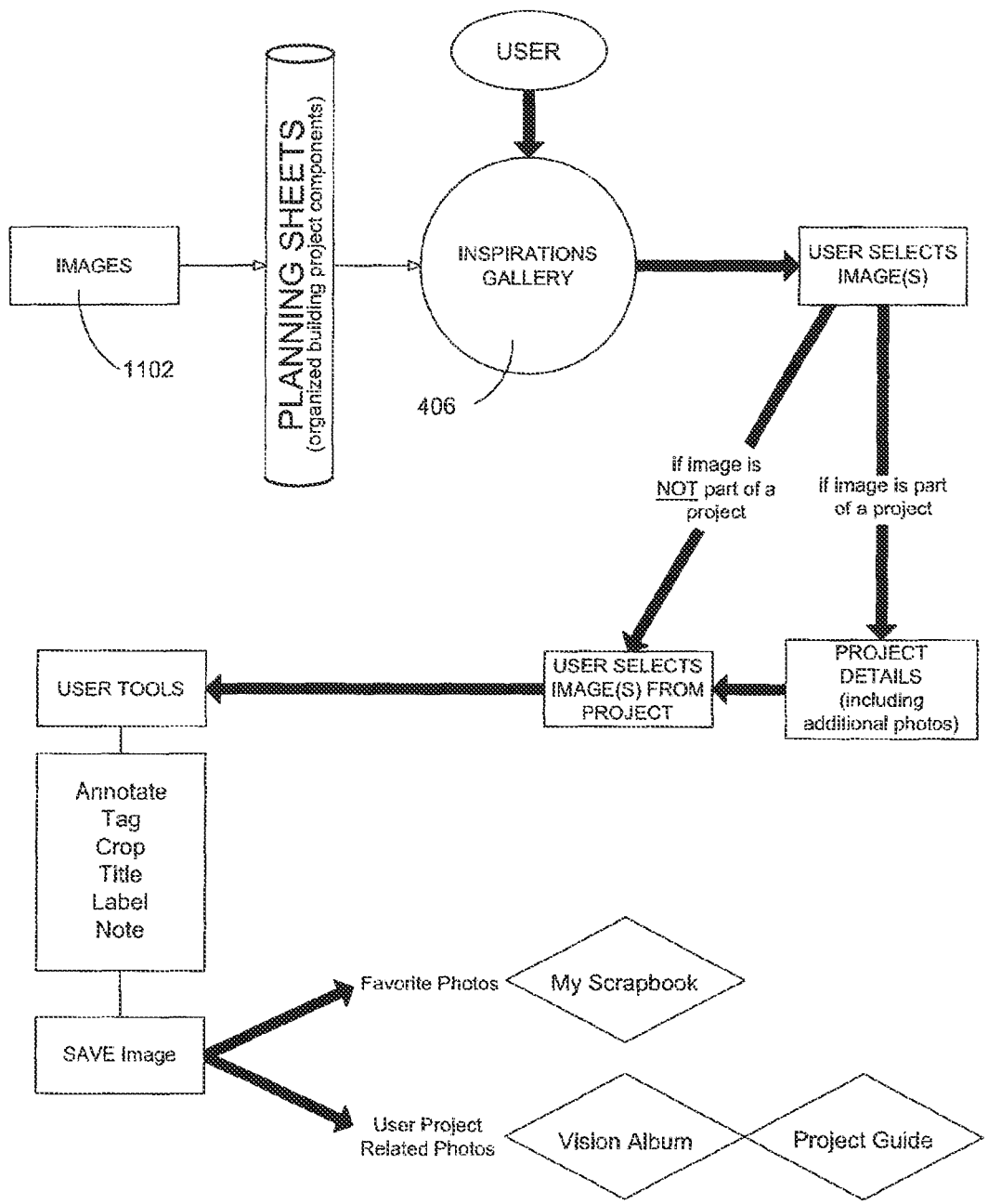
FIGS. 11A, 11B and 11C are a diagram and screenshots, respectively, illustrating features of the inspiration gallery according to an embodiment.
Figure 11B:
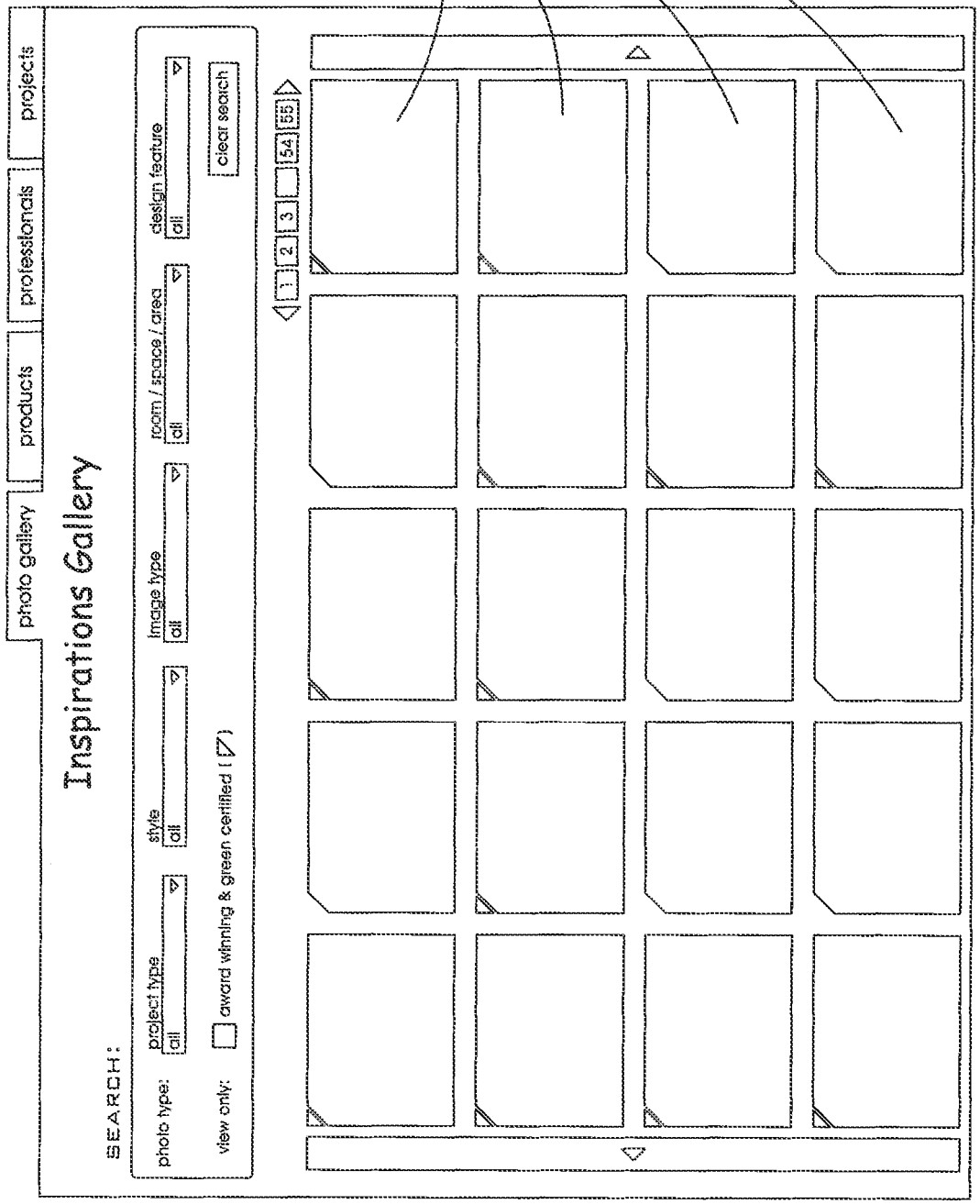
Figure 11C:
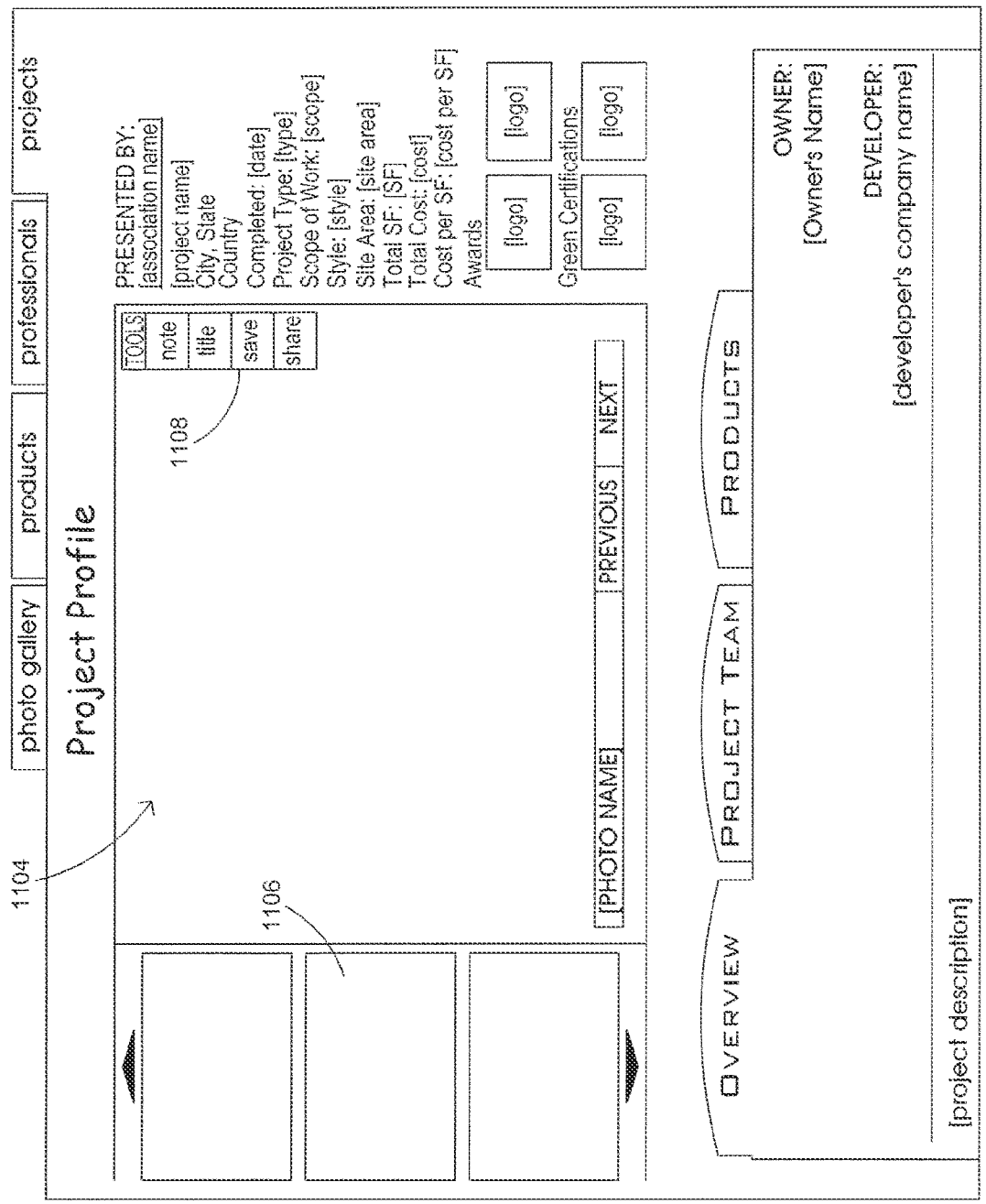

The Inspiration Gallery 406 provides the Owner 202 with the ability to view photos, images, and other samples of, for example, products, completed projects including award winning and green certified examples, floor plans and layouts and systems that are meant to inspire or generate ideas in the mind of the User. The images selected are grouped into a selected images file 406a (FIG. 4). FIG. 11A is a diagram of an embodiment of the Inspiration Gallery 406. As shown in this figure, images 1102 are coded and loaded into the Inspiration Gallery 406 via the planning sheets (described below) from the information providers, from other projects and from other industry sources. The Owner 202 may provide access to any person or group who the Owner desires to share their vision of the project during the Plan Phase. Comments received may be stored in an in-box for the Owner 202 to incorporate in some manner if desired. The Inspiration Gallery 406 may include, for example, thousands of images to millions of images available for viewing. In this embodiment, the User is able to access the Inspiration gallery 406 to view and select various images to help inspire his or her own project. The images may be displayed in a thumbnail format as shown in the screenshot depicted in FIG. 11B. The User may select an image 1102 that is already related to a project, in which case, the User may click on the image 1102 and further details 1106 regarding a specific image 1104 are made to appear as shown in FIG. 11C. The further details may include the names of products used and the names of professional service providers who provided the services. In one embodiment, a toolbar 1108 may be made available for annotating, tagging, titling, cropping, labeling and making notes to the selected images. The User may save project related images directly into the vision album. The project related images stored in the vision album are stored in the planning sheets related to the particular project. The User may save images that are unrelated to a project, but still coded from the planning sheets to a scrapbook for later use.

Referring again to FIG. 4, the Design center 408 provides a virtual marketplace from which the Owner 202 may make selections of building materials and products. The Design center 408 includes the ability to filter the choices made available to the user so that the building materials and products reflect only those items that correspond to the User's Vision as evidenced by selections found in the project information file 404a and the selected images file 406a. In one embodiment, the Owner 202 is allowed to research, compare, save and purchase products for the Project. In yet another embodiment, the Design center 408 may provide product choices that offer Green and sustainable products and systems so that the Owner 202 may optimize the Healthy, Green, Sustainable (HGS) nature of the project. The selections from the Design center 408 are placed into a selected products file 408a. In one embodiment, for each selection that an Owner 202 makes in the conceptual design element module 402, he or she is presented with additional ideas on how to implement the selection. In some embodiments, the additional ideas are provided to promote ideas that optimize the HGS nature of the project.

Figure 12A:
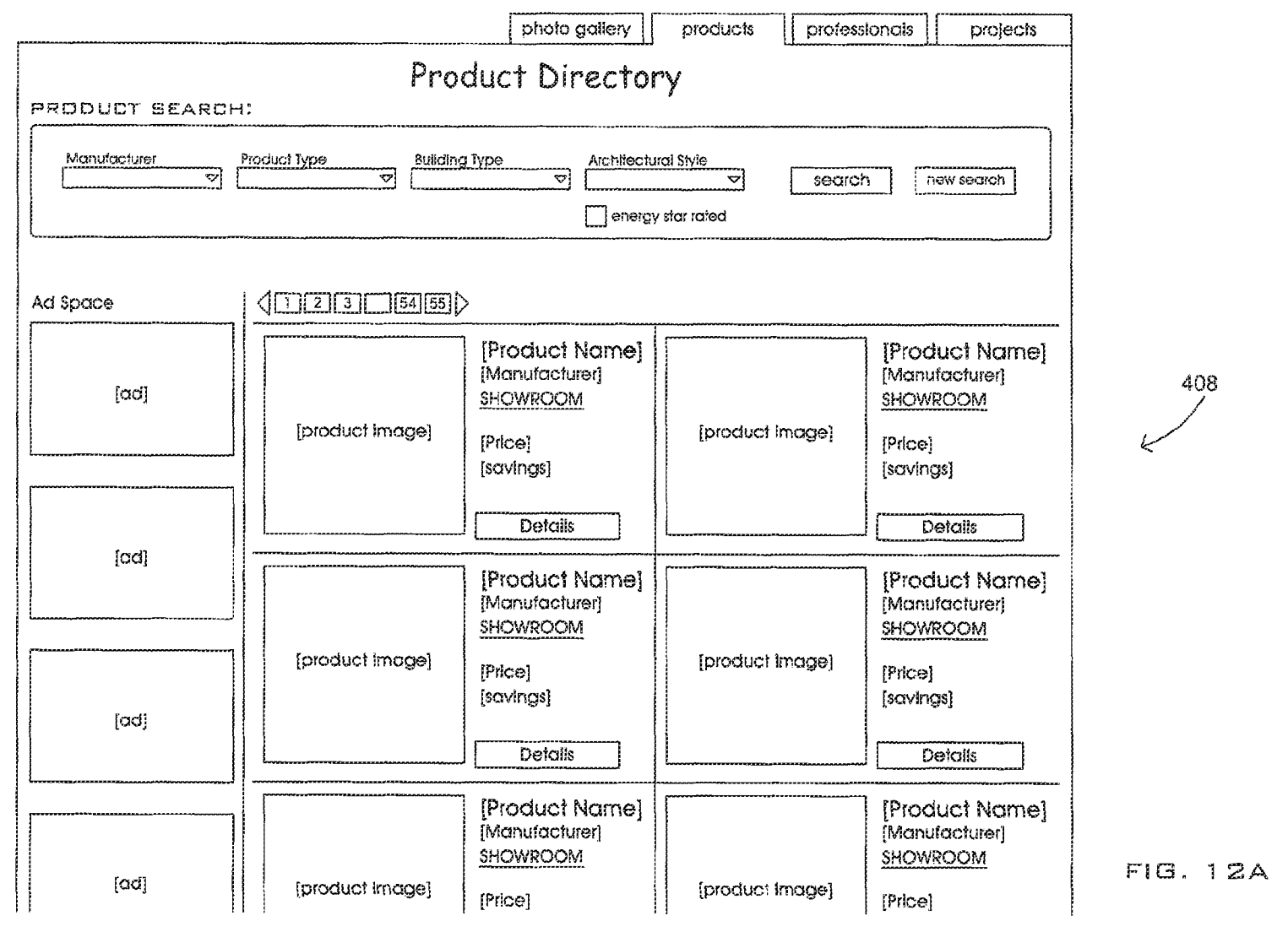
Figure 12B:
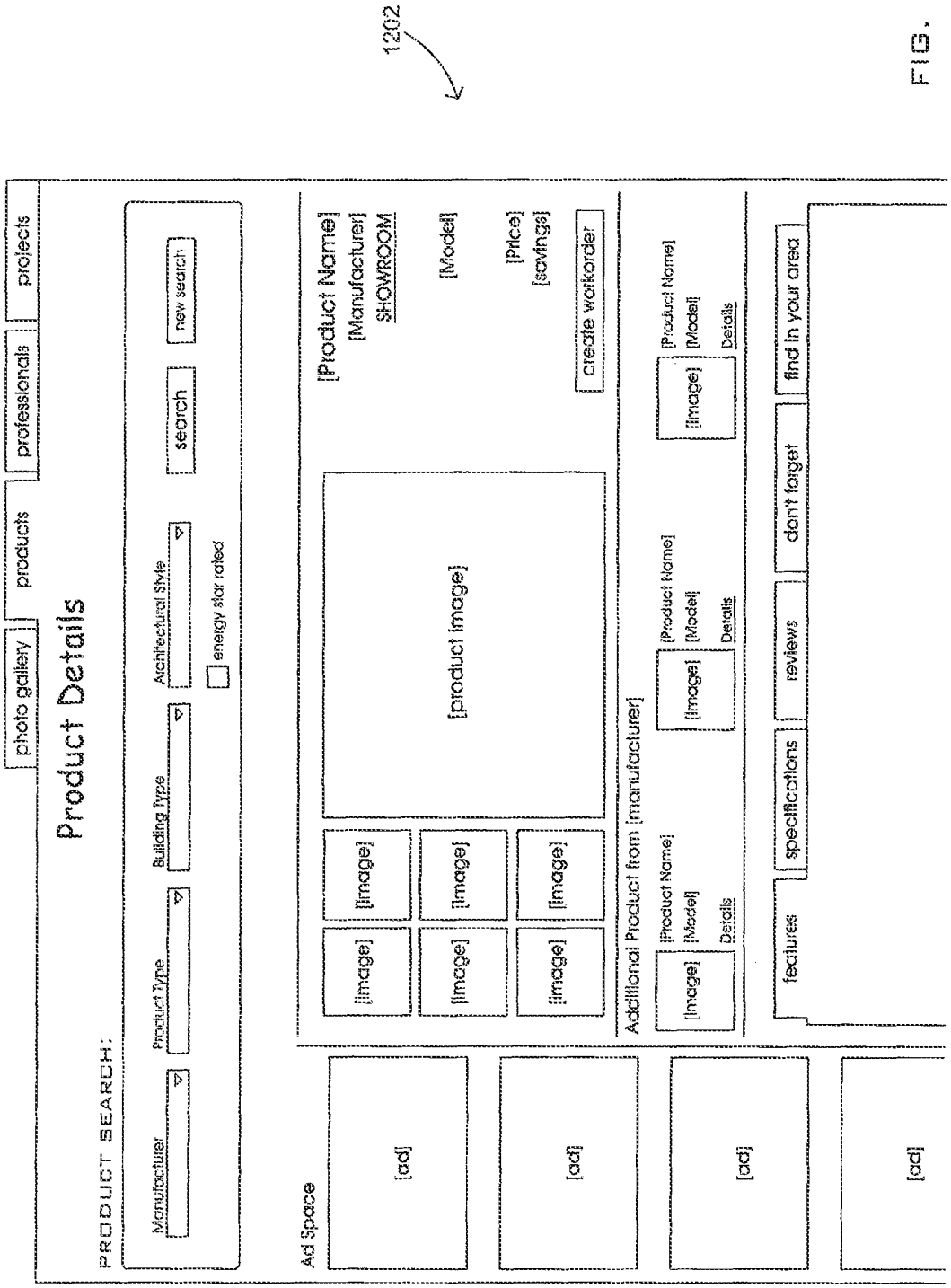

FIGS. 12A and 12B are screenshots illustrating features of the Design center 408 according to an embodiment. The Design center 408 is available to any User Group. The Users are allowed to view, select and purchase products. The Design center provides a portal for building materials, products and systems. In one embodiment, Professionals may be allowed to join a co-op type of membership where they may buy in bulk and presumably save money. In the design center, various products may be bundled and prepackaged for special offerings to users of the planning system. Preformatted work orders are also available to make the planning process for any industry installation more effective, efficient and complete.

In some embodiments, the Owner 202 may be allowed to save, organize and share his or her own images, product descriptions, professional referrals and the like in a separate images file referred to as a Scrapbook 410 created by the Owner 202. The data saved in the Scrapbook 410 may be compiled from sources outside the building system platform and may or may not be associated with a particular project. In one embodiment, the Vision Album may receive information from outside websites as directed by the user. A user using the planning system may be authorized to select images while visiting other websites. Thus, each image that the user selects may be stored in the Scrapbook 410 via a link back to the image's originating URL. The actual selections made from the Scrapbook 410 are placed into a selected images file 410a for use in developing the Vision Album 208.

In some embodiments, a Bid/Information Inquiry Room may be created so that the Owner 202 has the ability to post requests for bids to qualified professionals for acceptance or in the alternative may post requests for proposals so that qualified professionals may bid on a particular project or phase of a project. This particular feature facilitates and improves the accuracy of project forecasting and budgeting. The information drawn from the Bid Room may also be stored for use in the Vision Album.

Next, the information and data from the project information file 404*a*, the selected images file 406*a*, the selected products file 408*a*, and the user compiled information 410*a*, including any other information provided by the information providers 412, are compiled into the Vision album 208. It should be noted that the Owner 202 may start, save, and restart the development of the Vision album 208 at anytime and continue the development for as long as necessary to complete the guide or until the Owner is ready to proceed with the Project. In some instances, the Owner 202 may plan over an extended period, for example, from one month to upwards of 2-3 years or more to collect all of the data desired for the Project. Once fully developed, the Vision album 208 may be accessed by the Design team 204 or other industry consultants for incorporation of the information into the planning phase (second division) of the building system 200.

Figure 5:
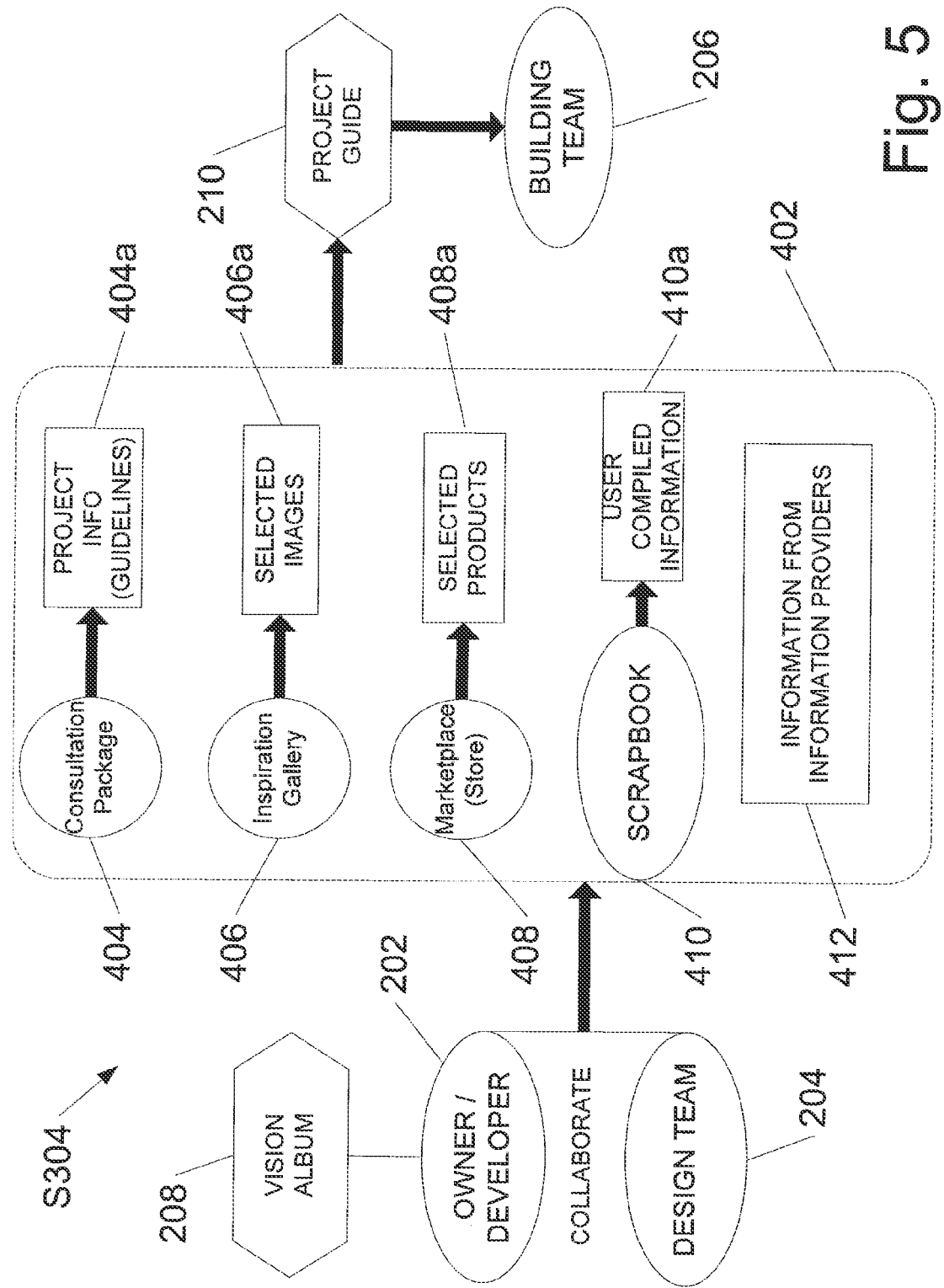
FIG. 5 is a diagram illustrating the creation of a Project guide in accordance with an embodiment.

FIG. 5 is a diagram illustrating the process (s304) of developing the Project guide 210 in accordance with an embodiment. As shown in FIG. 5, once the Vision album 208 is created, the information flow and collaboration between the Owner 202 and the Design team 204 begins to refine the Vision album 208 and develop the Project guide 210. The development of the Project guide 210 involves input from the Design team 204, which may include a host of Professionals, such as, for example, interior designers, architects, civil engineers, electricians, sound system specialists, landscape designers and the like. The Design team 204 reviews the Vision of the Project created by the Owner 202 set forth in the Vision album 208 and reforms or modifies the Vision into a workable reality with concrete line items, design criteria, specifications, plans and the like.

The Design team 204 may access the Vision album 208 to retrieve the information from the planning sheets necessary to begin formulating the Building Plan. The Design team 204 can use the information stored in the planning sheets as a guide and template to understand the needs of the Owner 202 for the Project. Any information that may be lacking may then be addressed by the Design team 204 using inquiries to the Owner 202. Similarly, the Design team 204 may access the Consultation package 404, the Inspiration gallery 406, the Design center 408 and the Scrapbook 410 to determine what the Owner 202 needs, wants and desires are for the Project. In many case, the Owner 202 or Design team 204 may determine that early involvement of the entire team to include the Build team 206 is advisable for the best project outcome. All participants are able at one time to access and comment or upload data to the project and the project planning sheets through the planning system. In one example, the Design team 204 from a first geographic location contributes to the planning sheets and the Consultation package 404 but cannot resolve or provide a final workable solution. However, a Design team, Build team or industry sector(s) member/group 1500 from a second geographic location, because of its different experience, exposure, and expertise, is able to contribute to the planning sheets and provide a final workable solution.

Advantageously, the building system 200 allows for complete collaboration between members of the User Groups. Here, the Design team 204 is able to go into the conceptual design element module 402 and process its work in one place using the Inspirations gallery 406 to determine the desired look of the project. The Design team is also able to go into the Consultation package 404 and Scrapbook 410 to find the needs, wants and desires of the Owner 202 and the Design center 408. The Design team is further able to go into the provider information 412 to search, select and store the products and systems the Owner desires to be used on the project. Any work that is not processed on the planning system may be uploaded into the project files becoming an inclusive source for all information and documentation on the project. Users are able to use forms such as payment requests, requests for payments, lien releases, proposals and contracts that are provided on a User Dashboard. These forms can be customized by the User or the User may up-load his own form. The process for bidding and billing may be a guided process, where all of the forms, including lien releases and payment requests are part of a checklist that is posted on the planning system. Once the forms are on the planning system, the forms maybe made available to any other User to avoid the use of separate forms and processes. The forms may be pre-vetted by a legal team or attorney. Having pre-vetted forms available is a valuable resource, for example, when a project has bank financing and there is a voucher system or payment control system in place.

Once conceptual design elements are refined by the Design team 204 and approved by the Owner 202, the elements are considered approved design elements. The approved design elements are then grouped into the Project guide 210 for delivery to the Build team 206. In some cases, especially when the intent is to certify a project as an HGS project, the Build team including subcontractors may be involved earlier on in the process. This earlier input may help to insure that everyone has had a chance to give their input, which may result in fewer changes during construction. The HGS projects are designed to function in a certain capacity and to have low levels of toxicity throughout the project. The Health of the occupants and the Environment are both considered when specifying products and systems. In many cases systems and components that are specified are designed to serve one another or to function together. When random changes occur during construction the building may no longer functions as originally designed. By having a communication and collaboration platform available, the Users may invite any member of any team onto the planning system at any time to comment or critique a decision. Thus, decisions may be based on complete information and understanding.

Figure 6:
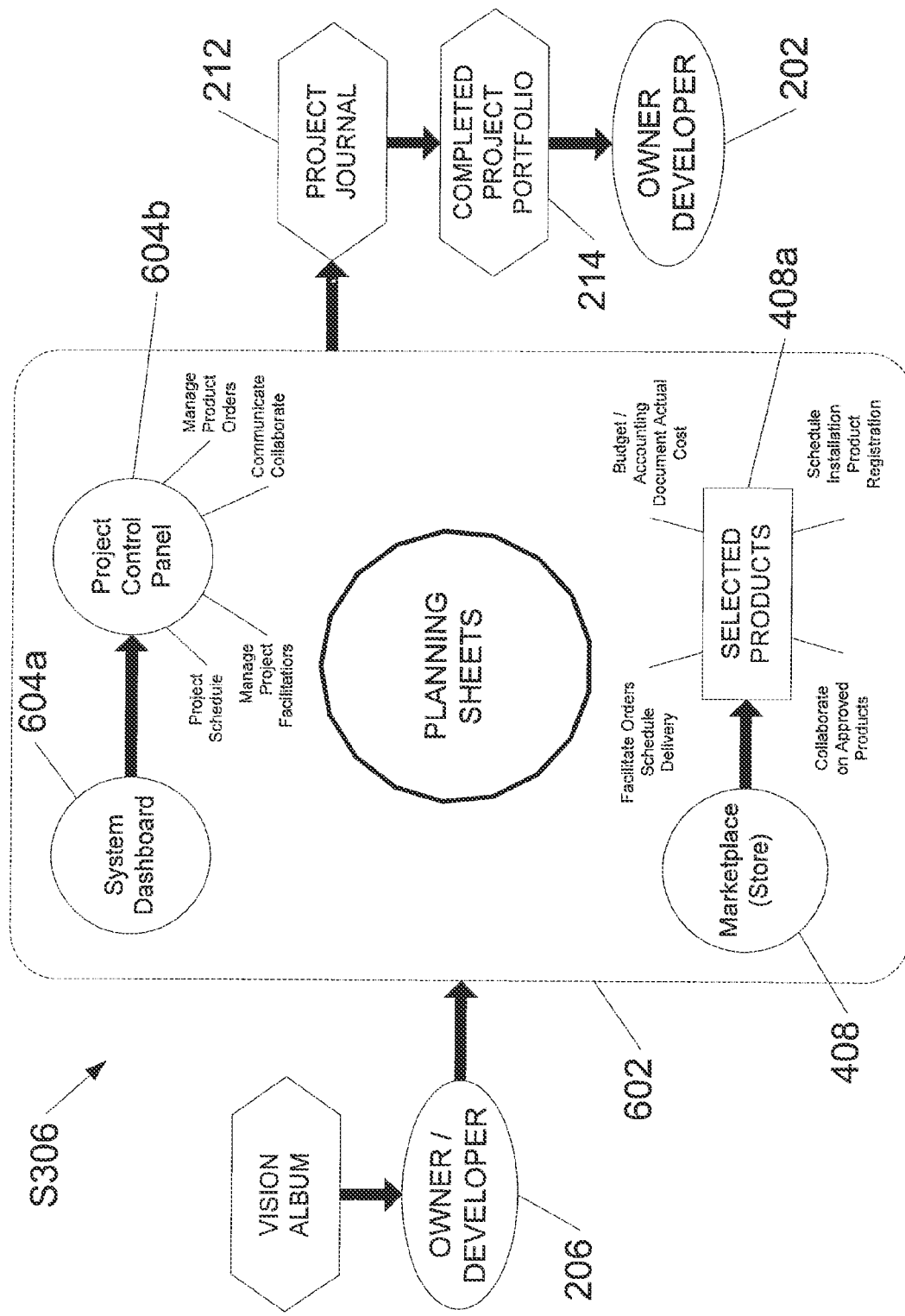
FIG. 6 is a diagram illustrating the creation of a Project journal in accordance with an embodiment.

FIG. 6 is a diagram illustrating the process (s306) of developing the Project journal 212 in accordance with an embodiment. In the building phase (third division) of the Project, the Build team 206, which may include, but not limited to, contractors, subcontractors, suppliers and the like, receives the Project guide 210 to implement the line items identified in the guide. The implementation may include a number of duties, all of which are detailed in the Project journal 212. For example, part of the collaborating and managing duties includes working with product suppliers on delivery, budget, warehousing, shipping, and scheduling.

Figure 13B:
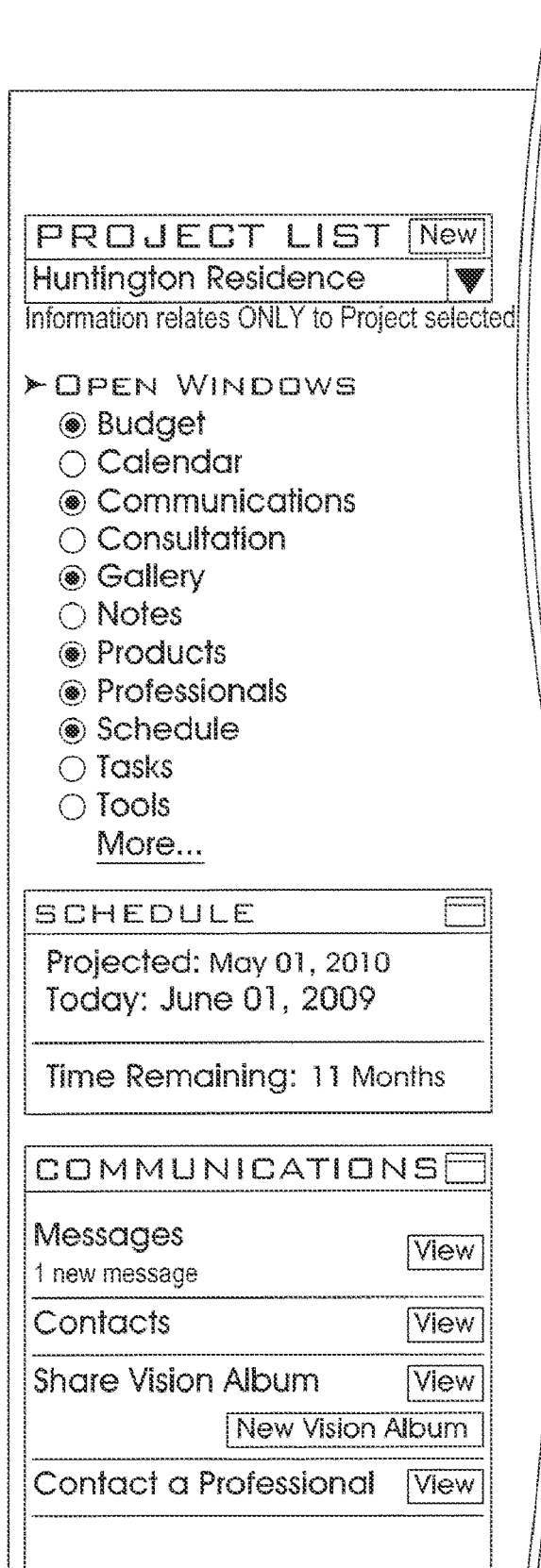
Figure 13B:
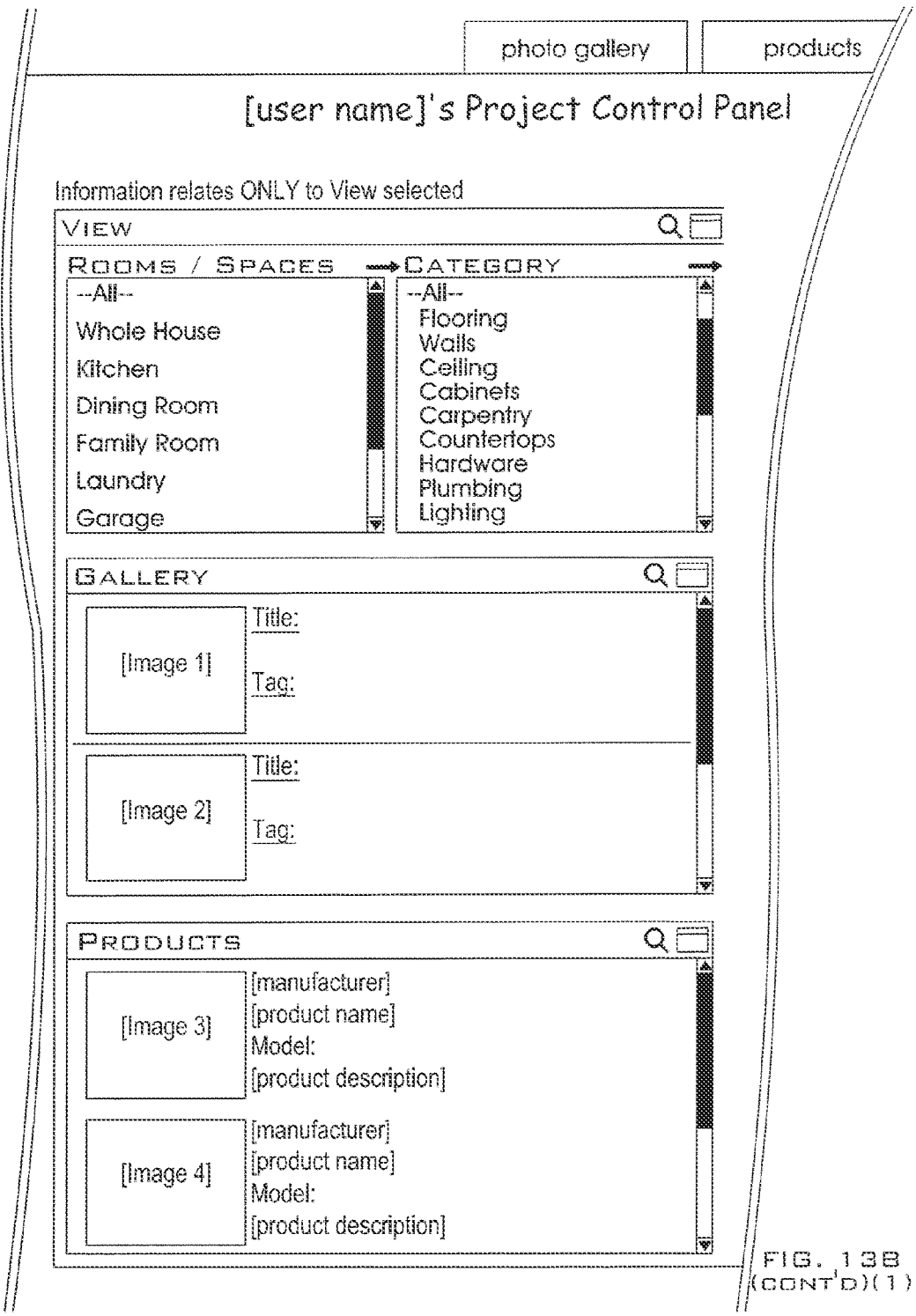
Figure 13B:
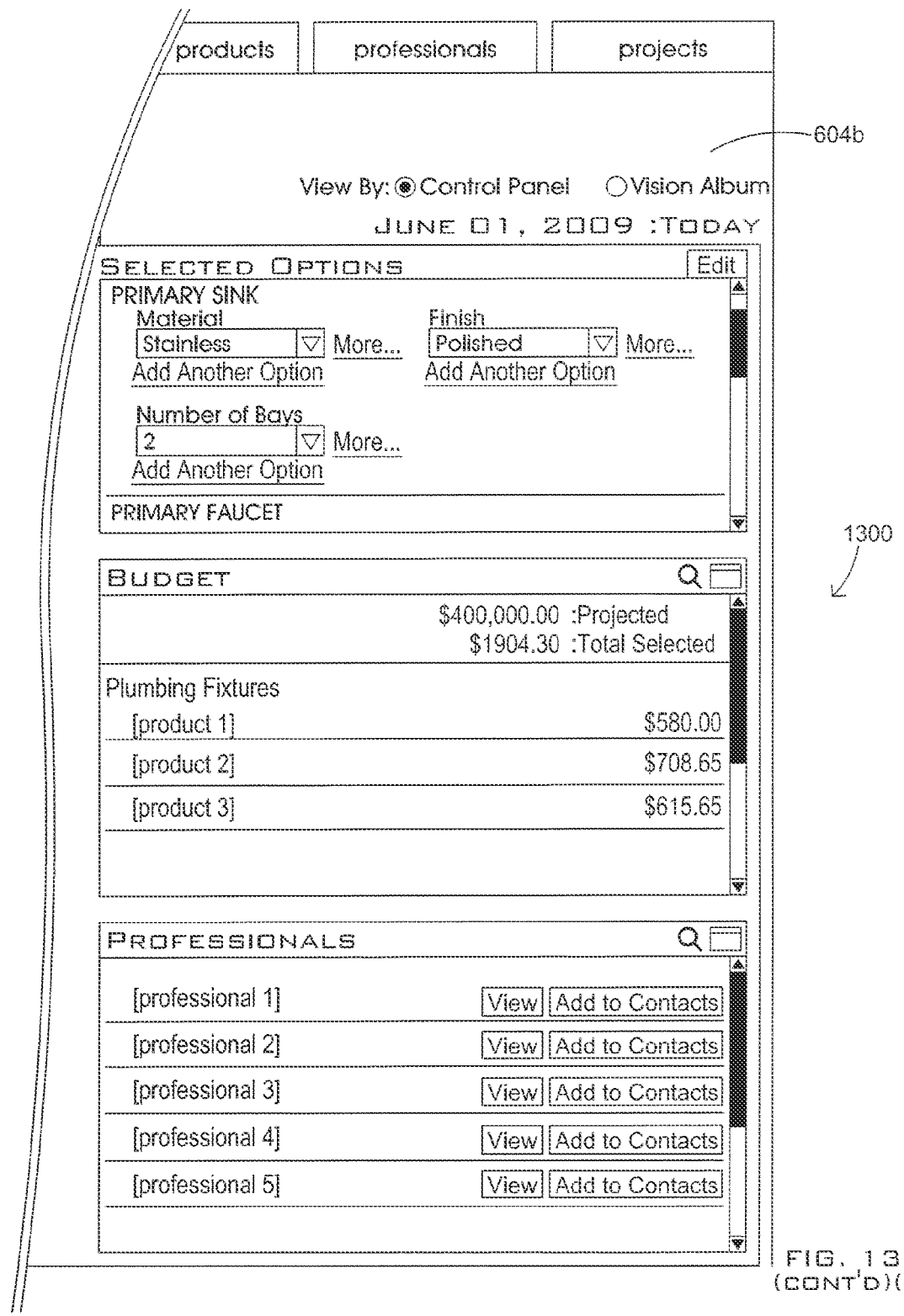

As shown in FIG. 6, after receiving the project guide 210, the Build team 206 may access a management module 602. The management module 602 may include a system dashboard module 604*a* and a project dashboard module 604*b*, which provide tools and controls that streamline the construction processes. For example, as shown in the screenshots 1300 of FIGS. 13A and 13B, in one embodiment, the system dashboard module 604*a* provides the ability to schedule, manage, collaborate, document, budget and the like, and share and communicate with other Users on the project. The project dashboard module 604*a* may also provide a management tool allowing for management of one or more projects. The project dashboard module 604b is a project specific tool where a user manages and accesses all data stored to a specific project including data and information from the Inspirations Gallery, Products Directory, Project Gallery, Professional Showcases and the like.

Referring again to FIG. 6, in one embodiment, the management module 602 provides access to, for example, the Design center 408 and the selected products file 408a. The information assembled in the selected products file 408a provides the Build team 206 a guide from which to bid on products and services, schedule deliveries, communicate and collaborate on owner/developer approved products, budget actual costs, order and track product orders, and record any modifications that are made during the process. The Build team 206 assembles, compiles and records the actions taken to implement the project, including the information and data generated in the management module 602 about the Project into the Project journal 212.

While developing the Project journal 212, the Build team 206 is involved with the actual construction of the Project. Thus, the Project journal 212 is also supplemented with information and data detailing the actual actions taken to construct the Project. Because of the detailed accounting in the Project journal 212, the Project journal helps to reduce any misunderstandings, miscommunications and misinformation that sometimes plague other construction planning schemes. The Project journal 212 may provide a valuable tool in helping to avoid or reduce the impact of any arbitration or litigation that may stem from the construction Project.

As a final step in the process (s308) of the building system 200, the aggregate of the information assembled in the Vision album 208, the Project guide 210, and the Project journal 212 are assembled into the Project portfolio 214, which now includes detailed information about every aspect of the construction Project. The completed Project portfolio 214 is provided to the Owner 202 to provide a historical guide that may be helpful with regard to future maintenance and renovation projects. For example, when a product or system breaks down and repairs are needed, the owner or maintenance person may refer to the Project portfolio 214 to determine who manufactured and installed the product or system and who to go to for warranty work and the like. In many instances, the information provided in the Project portfolio 214 makes it possible to repair instead of replace, since the product information is available to re-order or find parts. In the event that an addition, remodel or renovation is to be made to the Project, the Project portfolio 214 may provide information that may be needed to efficiently begin the new Project. For example, information regarding the locations of critical support beams, electrical outlets, sewer line, pluming pipes and the like, may reduce the need to open up walls, break up concrete or climb in attics or crawl spaces to get the same information. Engineering specifications and the like kept in the Project portfolio 214 may help to reduce the time required to obtain a permit for new construction. Choices made regarding room colors, wall textures, fabrics, carpets, fixtures and other finish products may help to facilitate these selections for a renovated space, as well as ensure consistency of quality. Thus, the technical features of the computer-implemented process for generating a planning document should be understood to include the ability to generate a first guide or report that includes parameters, guidelines, product selection and service selection relating to a project selected by a first user; generate a second report that includes modifications to at least one of the parameters, guidelines, product selection, and service selection relating to the project based on input by a second user; and generate a third report that journals actions to be taken in implementing the project using the parameters, guidelines, product selection and service selection set forth in the first report and as modified in the second report.

In one embodiment, a user may access the planning system not to plan an entire project, but instead to use the planning system to document a project. The user may enter the project criteria into the planning system that delivers a set of planning sheets to the user. The user journals all of the product and system data as it is being installed. The user may do additional research and document the products installed before the information is lost. With this information, the user may create a type of Project Portfolio, which serves as a valuable tool for the Owner and future Owners of the building. The Project portfolio will also be valuable to a building owner or an insurance company in the case of a catastrophic loss. The Owner will not have to go back and try to recreate the structure and the components from scratch. The insurance company will also be able to rely on an accurate set of data and will not be subject to paying for or replacing items that were not installed. The Project portfolio is also a valuable tool to Developers who build and turn over a project where recommended or mandatory maintenance should be done but could be overlooked. An example is a developer who builds a condominium complex, sells the units and turns the project over to a HOA. The project has decks on some of the upper levels that require maintenance and recoating every 3 to 5 years. Seven years after completing the project the builder is notified that the decks are leaking and that there is rotting structural members and damage to the lower units. The builder delivered a Project Portfolio that included a ten year maintenance schedule to the HOA. The schedule called out and notified the HOA that the decks were due to be cleaned and recoated at three year intervals. The maintenance schedule called out the products to be used and the company who provided the service in the area. The HOA was unorganized and overlooked the deck coating process. The HOA was unable to produce documentation that it had followed through on its responsibility, thus the developer/builder and their insurance companies are not liable. However, with a schedule that provides the information needed by the HOA and notifies the HOA when the work is to be done makes it easy for the HOA to maintain and upkeep buildings. Another advantage of the Project Portfolio is realized when a building is being renovated or demolished. The Owner/Builder/Developer can each post the project on line and make its soon to be discarded materials available to charitable organizations such as Habitat for Humanity who may be interested in pulling out some of the products and materials to recycle or reuse, therefore reducing waste at overfilling landfills and demolition costs.

Figure 7A:
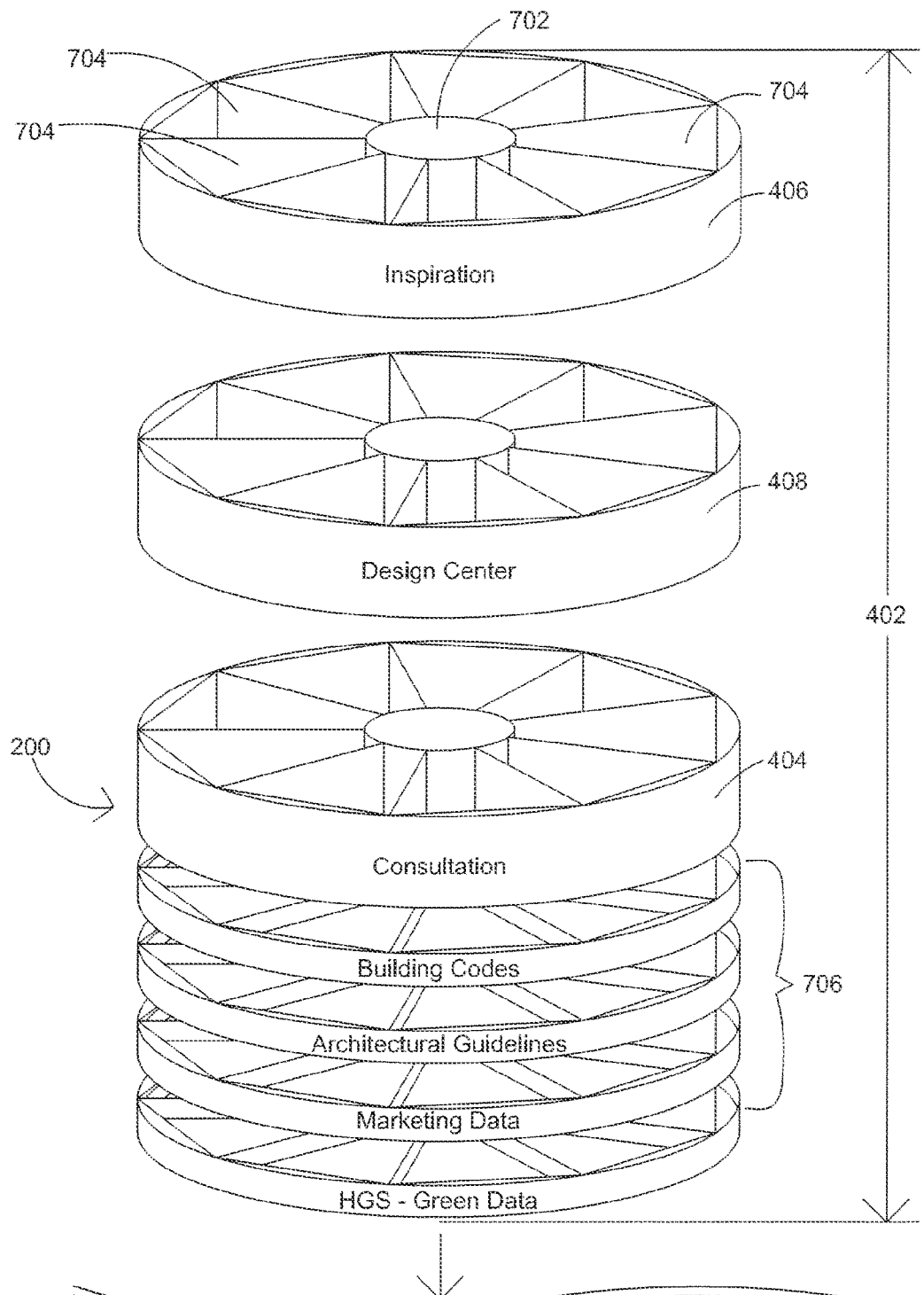
FIG. 7A provides a diagram illustrating a comprehensive planning, management and communication tool in accordance with an embodiment.
Figure 7A:
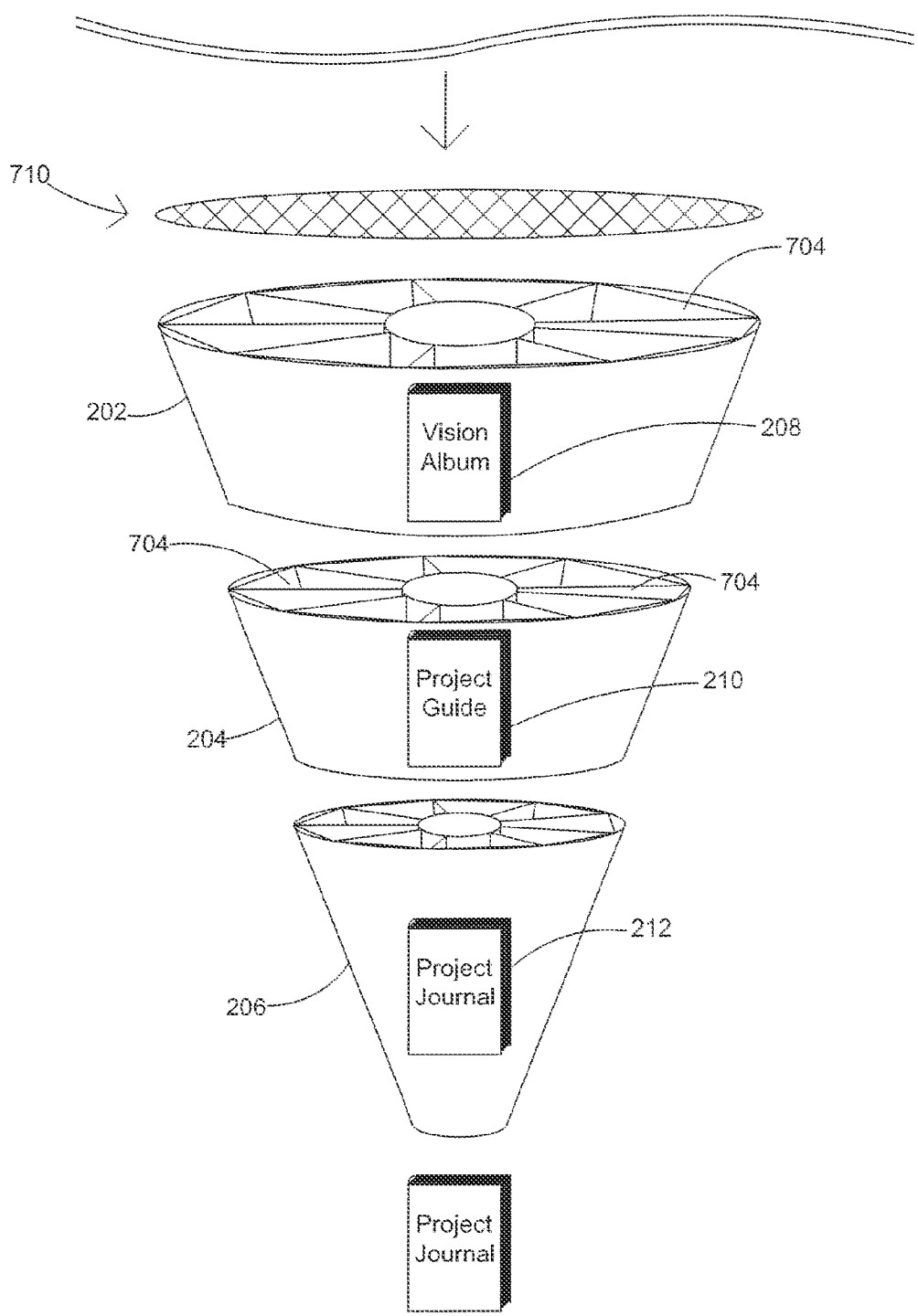

FIG. 7 provides a diagram illustrating a comprehensive view of the start to finish, plan, management and communication segments involved in the planning system as it relates more specifically to the planning sheets in accordance with an embodiment. The diagram provides a visual representation of how information is fed into each segment, from a previous segment, and into the planning sheets of the planning system to provide a completed Project portfolio 214 in accordance with an embodiment.

In the context of the building system 200, the process shown in FIG. 7 is generally initiated by the owner or developer that desires to either build a new structure or renovate an existing structure. In operation, the Owner 202 provides information regarding the concept or vision for the project. One aspect of the information includes project criteria information, such as location, type of construction, type, use and number of rooms, sizes, options and other associated parameters and guidelines. The information may be inserted into building system 200 using any well know user interface, for example, but not limited to, a graphical user interface via fillable forms, selectable lists or images, and prompts, such as via an iterative interview process and the like. As previously described, all information regarding the Project is entered into building system 200 via the planning sheets that incorporate a means to classify building parameters, products and processes. In the planning sheets, products, services, systems and the like are categorized and may be selected using a systematic approach that follows an order that emulates closely with how a building is actually constructed as opposed to, for example, the typical Construction Standard Institute (CSI) order of product selection. The planning sheets provide a visual tool that allows Professionals, as well as project owners, to view, select, store for review and purchase building products, services and systems through each segment of the construction project.

In FIG. 7, the planning sheets 702 are represented as a wheel or circle divided into individual plan sections 704. Each individual plan section 704 represents a different phase or aspect of the design/construction process, thus allowing the User to individually account for most or all aspects of the construction process. As shown in the figure, the planning sheets 702 transcend through the entire system. As the system continues toward the formation of the Project portfolio 214, the planning sheets 702 visually narrow, representing the fact that the information and data regarding the Project have become refined and finalized because of the communication, interaction and collaboration of the User Groups.

Figure 8A:
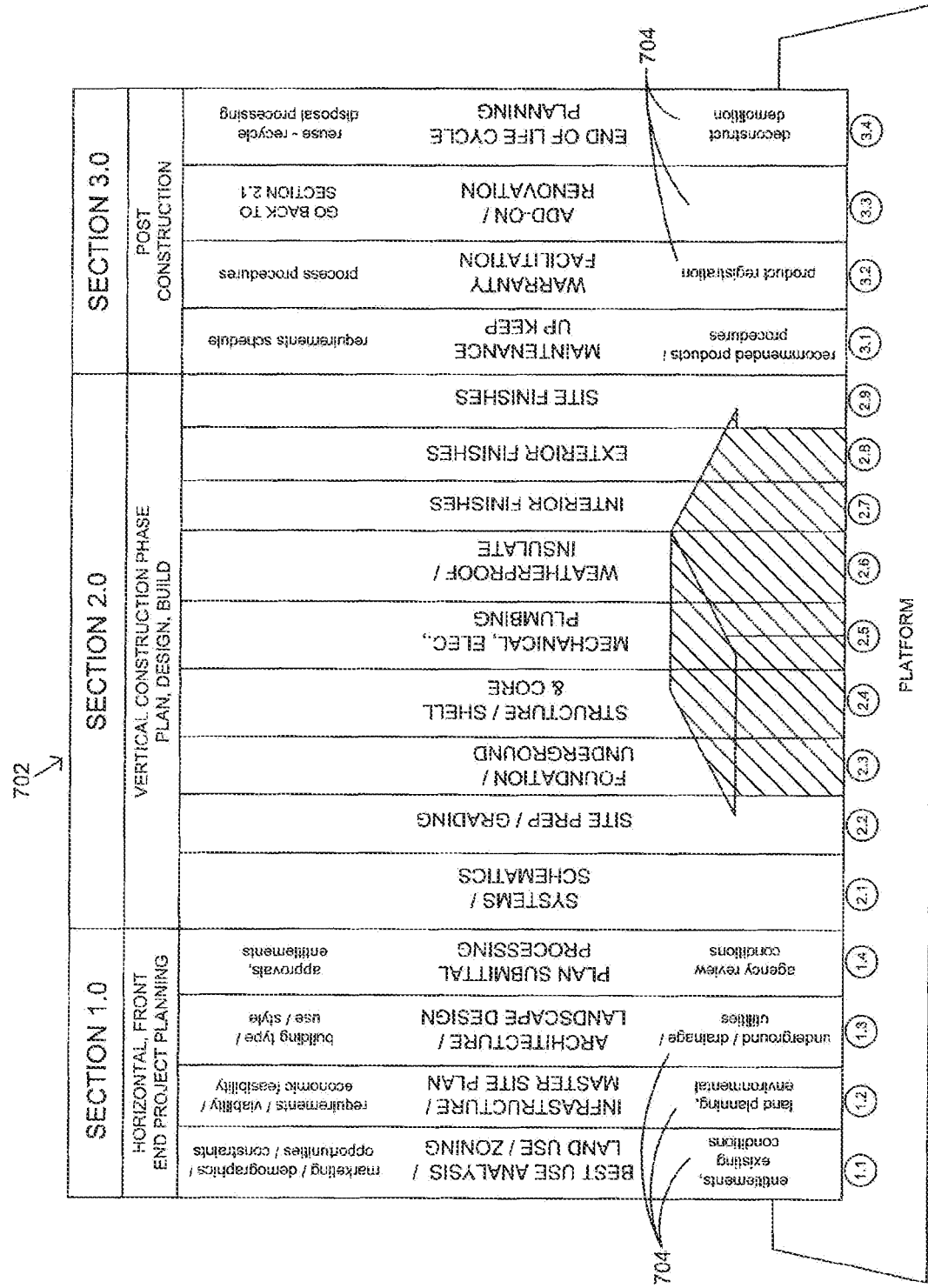
FIGS. 8A and 8B are illustrative examples of a planning sheet according to an embodiment.

The plan sections 704 may be divided into any number of phases or aspects that may be considered a part of the construction process, and may be individually customized by each User for each particular project. As shown in the graphical example in FIGS. 8A and 8B, in one embodiment, the plan sections 704 may include, but are not limited to, plan sections, such as project analysis, infrastructure, systems schematics, site preparation and grading, foundation and underground, building structure, shell and core, mechanical, plumbing and electrical, weatherproof and insulation, interior finishes, exterior finishes and site finishes, maintenance, warranty and the like. The planning sheets are broken down to achievable phases of the project then to the components and tasks that need to be selected then worked on or installed. A budget may be attached to the components (e.g. labor and materials), and a schedule is created so the tasks flow through the project as referenced by the planning sheets.

Figure 8B:
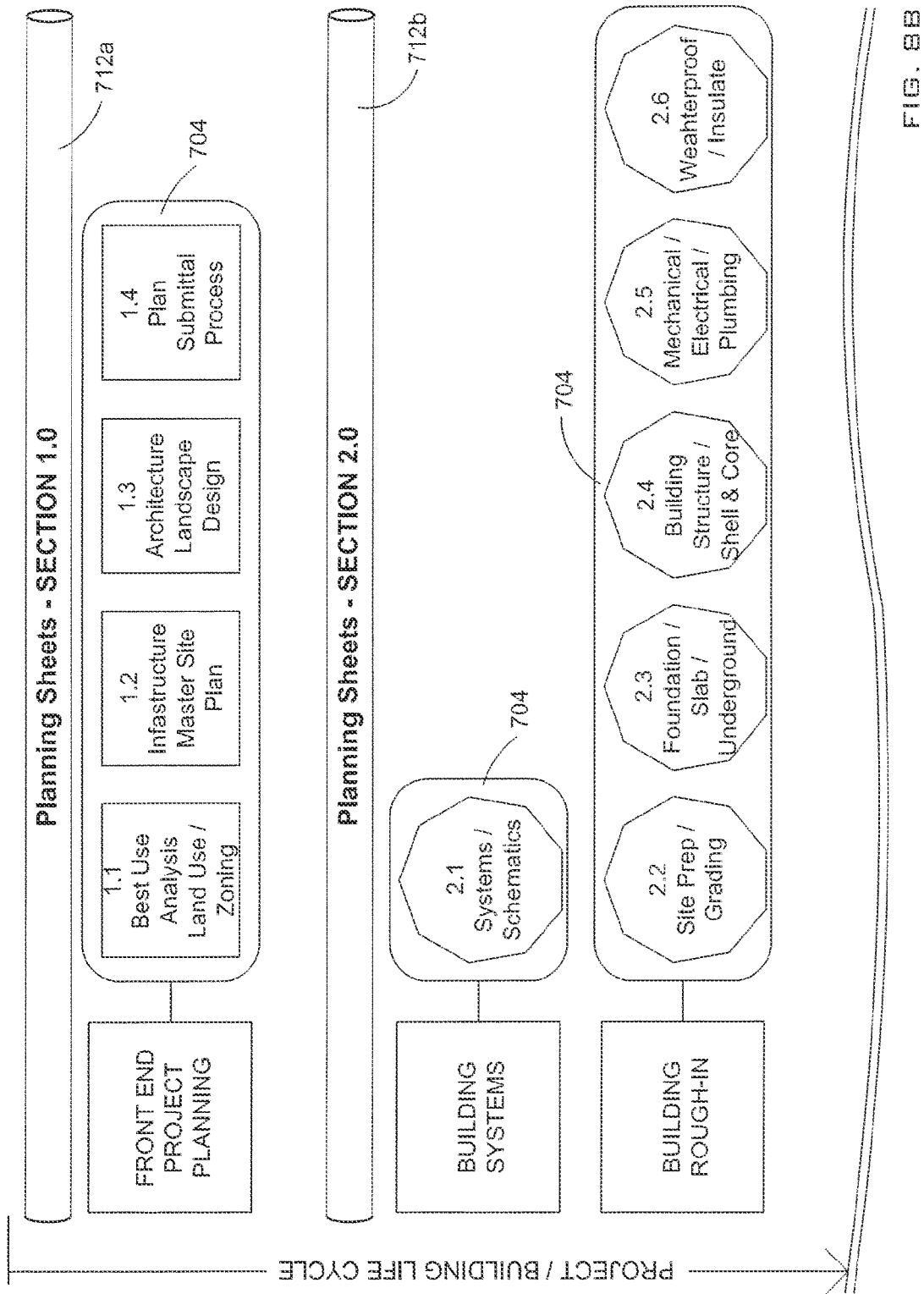
Figure 8B:
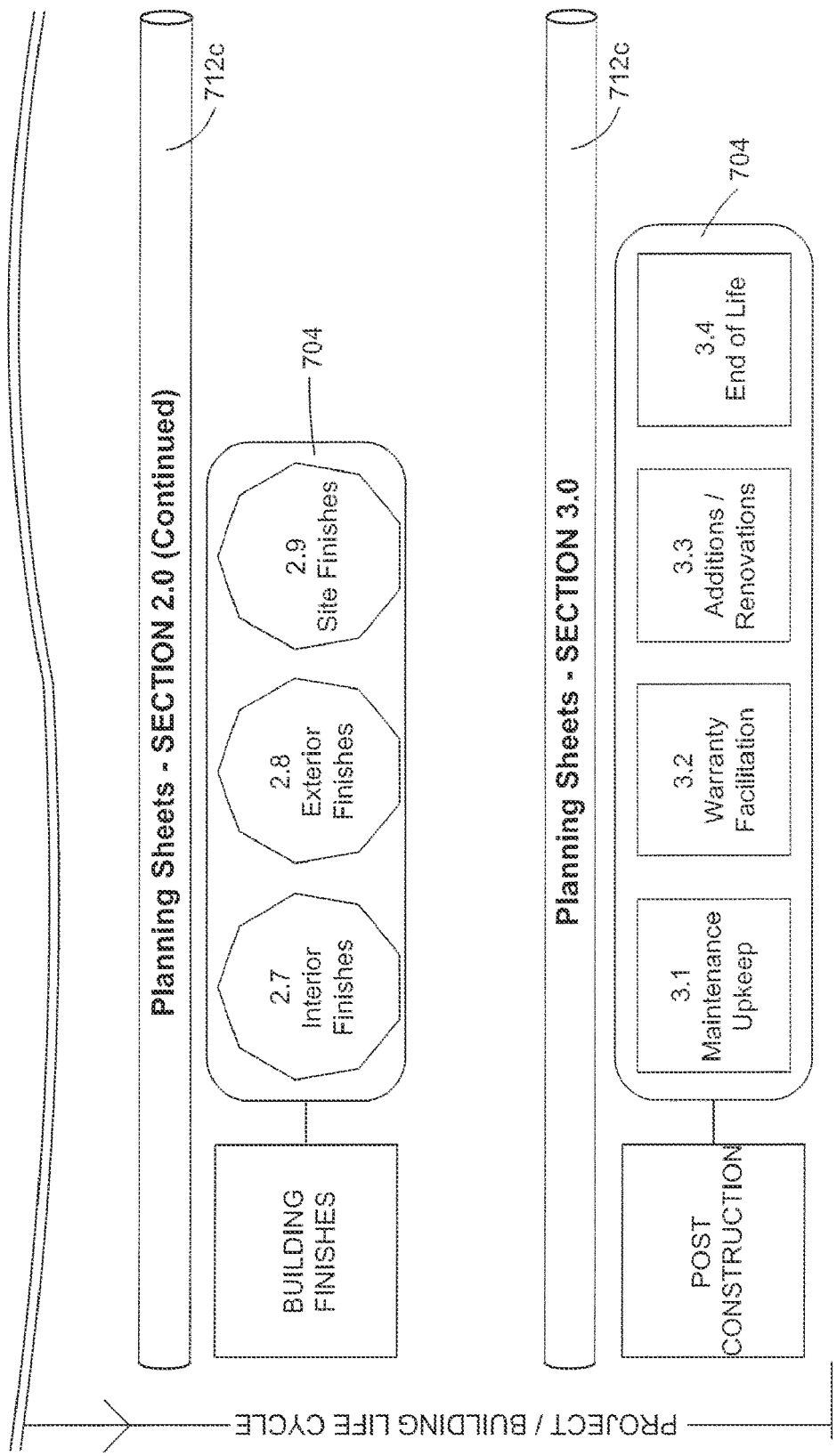

In one embodiment, as shown in FIG. 8B, the planning sheets 702 may be divided into at least three sections. For example, Section 1 (712*a*) may include the front-end project planning data. The front-end project planning data may include plan sections 704 related to Land use/Zoning, infrastructure, architecture, landscape and the like. Section 2 (712*b*) represents the plan, design and build phases of a construction project. The plan sections 704 include systems and schematics, site prep and grading and interior finishes, for example. Section 3 (712*c*) represents the post construction section of the planning sheets. The plan sections 704 in the post construction section include, for example, maintenance and upkeep, warranty facilitation.

Figure 8C:
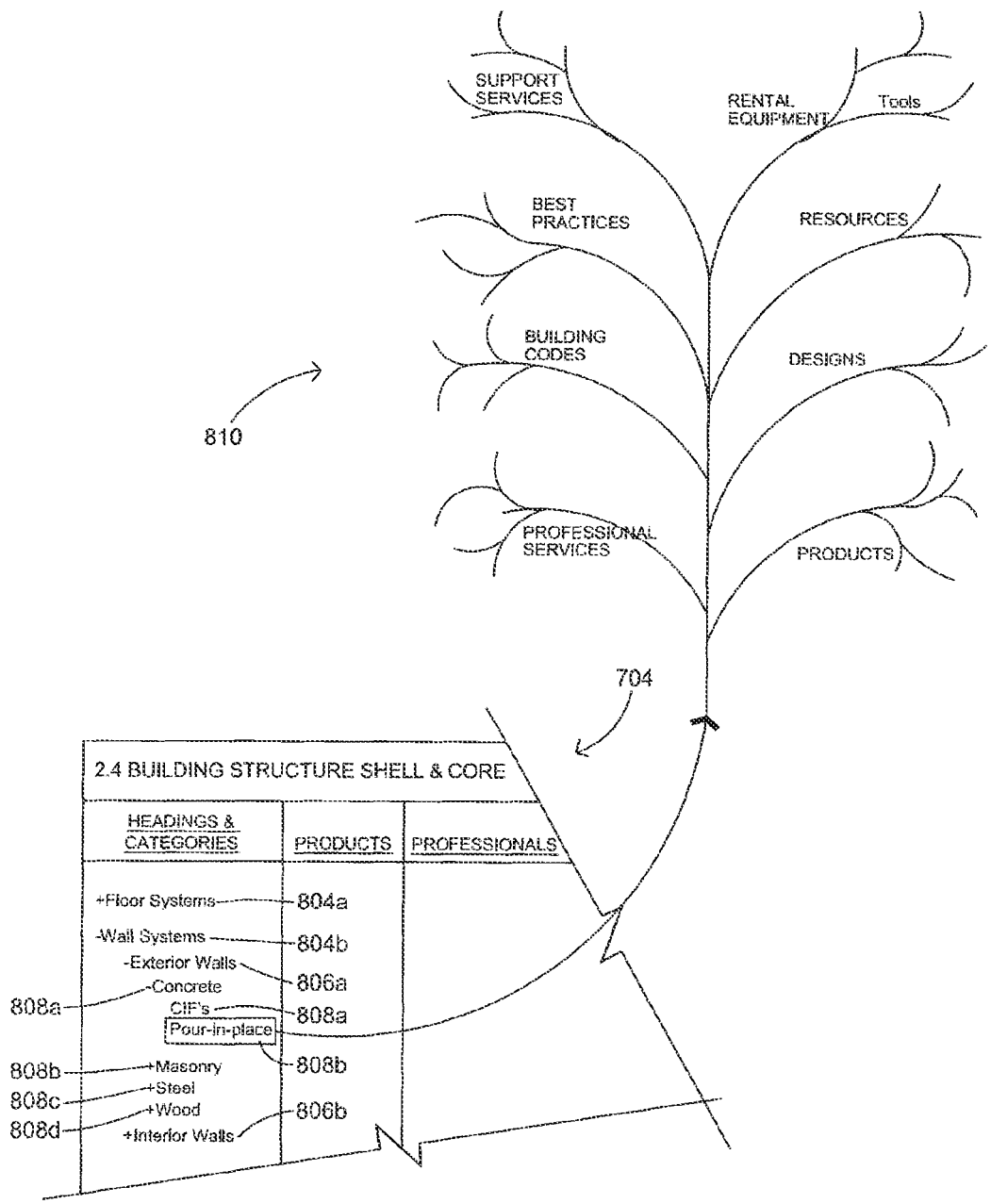
FIG. 8C is an illustrative example of a of a plan section and an exemplary illustration of its searchable categories according to an embodiment.

The plan sections 704 may be further divided into classes/categories and subclasses/subcategories that account for particular aspects of the phase or aspect of the construction, such as materials, products, systems and processes that fall into each phase. For example, FIG. 8C shows a representative plan section 704 for a particular project, such as Building Structure Shell and Core. The plan section 704 indicates classifications 804, including for example, Floor systems 804*a* and Wall Systems 804*b*, which includes a subclass for Exterior Walls 806*a* and Interior Walls 806*b*. Exterior Walls 806*a*, for example, has sub-classes for Concrete 808*a*, Masonry 808*b*, Steel 808*c* and Wood 808*d*. The sub-classes may have further sub-subclasses, such as CIF's 808*a* and Pour-in-place 808*b*.

The plan sections 704 may be individually searchable among each classification and sub classification by all User Groups. As shown in FIG. 8C, the information stored in the plan section 704 may be represented as a tree with branches 810 that store all of the pertinent information searchable within the particular plan section 704. For example, for a particular classification, the plan section 704 may store data and information related to professional services needed or desired, building code information, if appropriate, best practice tips to share with the build team or others, availability of equipment and tools that may be required, and public and governmental resource information, if needed. Any particular plan section 704 may include other branches of information if the project or classification so requires.

In one embodiment, once a planning sheet 702 and product category is selected, the Design center 408 may compile a list of products with associated information. If the User chooses, filters may be used to narrow product selections in view of previously designated preferences. In one embodiment, the User may preview all of the products, sort them, compare them and save them for later access. As shown in FIG. 12B, details 1202 regarding a particular product may be selected for viewing. The details may include, for example, an overview, specifications, user reviews, additional photos, video, certifications, and a list of items related to the product.

In one example, in a plan section 704, a classification 804*b* related to Wall Systems for Exterior Walls 806*a* may have a sub-classification for materials, which may include concrete 808*a*, masonry 808*b*, steel 808*c*, and wood 808*d*. Thus, the search tree 810 may include wall designs and products available for building a particular wall type, a list of professionals that may provide the materials for the walls, building codes for building the various types of walls, equipment and equipment providers, best practices for building walls and various resources available for making sure that the wall is environmentally friendly, for example.

Referring again to FIG. 7, the User maybe inspired by images and suggestions that are made available for selection via the action modules or databases including the Consultation package 404, the Inspiration gallery 406, the Design center 408 and the Scrapbook 410. The selections made using these modules populate the appropriate plan section 704 in the planning sheets 702.

In one embodiment, informational segments 706 may be provided, which provide all types of information that may be useful to Professionals, Owners and Developers for making selections regarding materials, products, systems, contractors, subcontractors and the like. The Informational components may be updated periodically as new and useful information becomes available. The information provided may be accessed by any User of the building system and may stand alone as a separate database of information. The Informational components include, but are not limited to:

Building Classifieds—a networking component for Users to list building related materials, services, projects and the like for sale or use to other Users.

Green Info—the latest and most straight-forward information about Green products and services, for example, design samples and installation schematics, building practices, products, systems, what works and what does not work and the like as well as rebates and incentives for Users to consume at retailers and wholesalers in a particular geographic region.

Find & List Professional Services—a directory of professionals from around the world, including Architects, Engineers, Designers, Builders, Installers and the like in a particular geographic region.

Thus, the technical features of the computer-implemented process for generating a planning document should be understood to include mechanisms configured to receive an input from a first user that includes user selections relating to a project type; generate planning sheets related to the project type and populate segments of the planning sheets with a first set of data categorized based on the first user selections; grant access to the planning sheets to a second user and allow the second user to modify at least a portion of the first set of data to create a second set of data in the segments of the planning sheets; and grant access to the planning sheets to a third user and allow the third user to journal the actions to be taken in implementing a project based on at least portions of the first and second sets of data in the planning sheets. A further feature of the present computer implemented process is provisions for allowing the first user, the second user, and the third user from three remote locations to interact. In one example, the first user and the third user are from two different states. In other example, the first user and the second user are from two different continents. In yet another example, the second user and the third user are from different states or from different countries. In still yet another example, the first user and the second user are from different countries.

It may be noted that the vast amount of information and the number of selectable choices may overwhelm the User of the building system 200. Thus, the building system 200 includes a filtering mechanism 710 that provides a means for the User to narrow or limit his or her choices based on the specific project criteria and other information as well as selections made from, for example, the inspiration gallery and design center provided by the User. The number and types of filters can vary depending on the project type. In one embodiment related to the building construction project, the filters may include project scope filter, climate zone filter, architectural style filter, systems filter, foundation/flooring filter, foundation filter, color filter, material filters and the like.

Figure 9A:
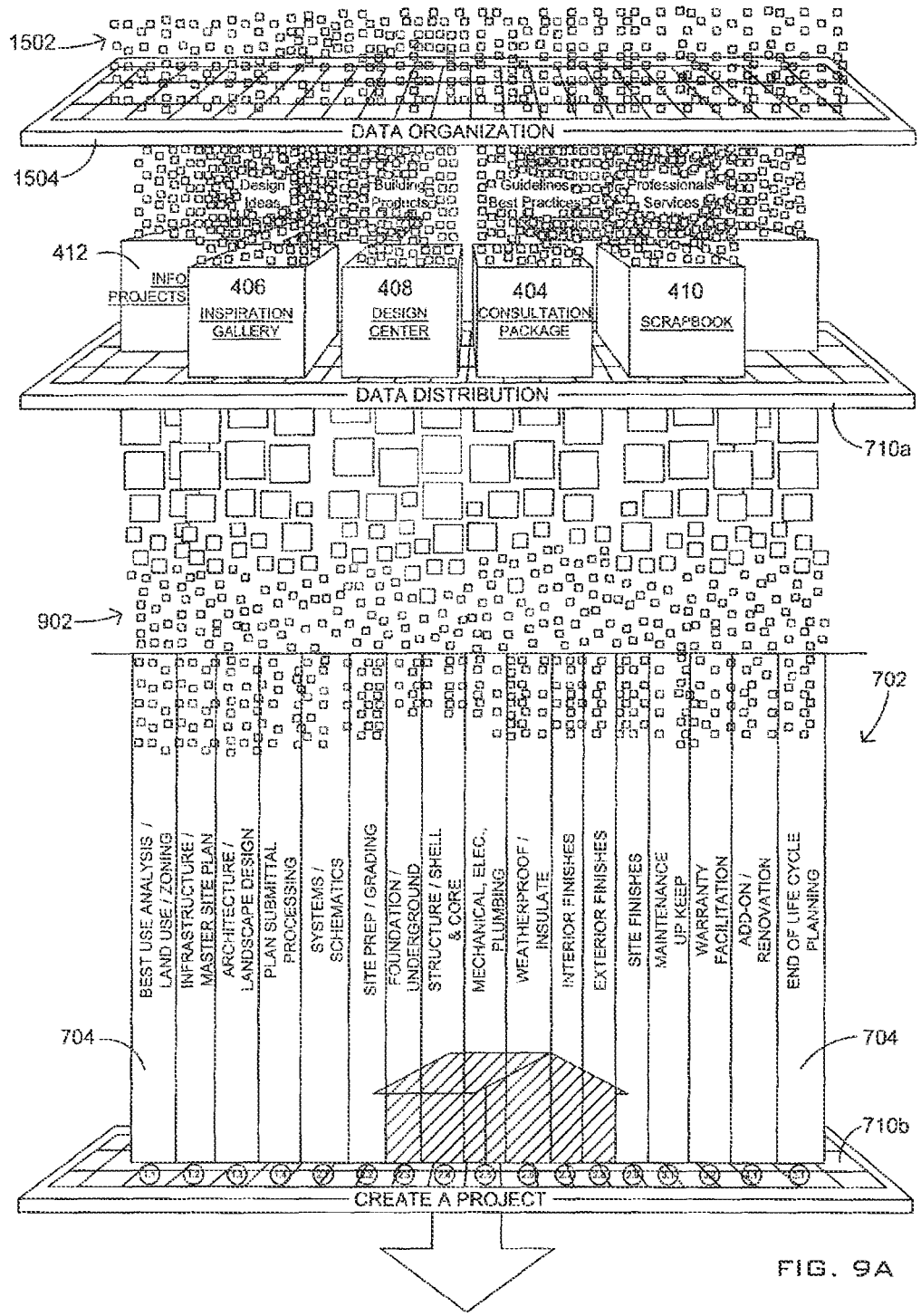
FIGS. 9A and 9B are diagrams illustrating how information is filtered and stored into the plan sections according to an embodiment.
Figure 10:
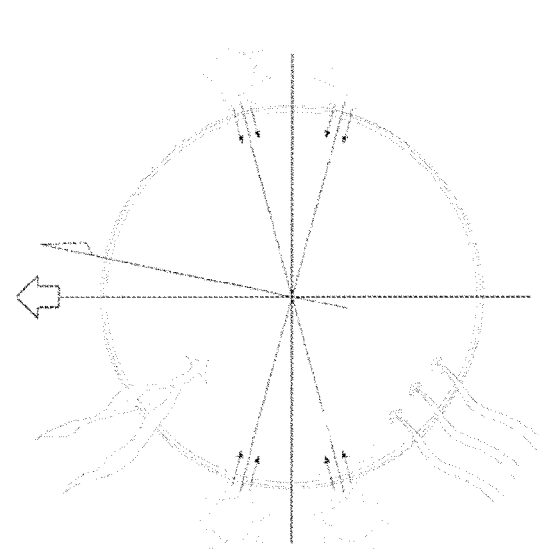
FIG. 10 is a screenshot showing an example of a graphical user interface for the planning system according to an embodiment.

As previously mentioned and as shown in FIG. 9A, data and information 1502 come into the building system and are passed through data filter 1504 to organize, aggregate and deliver the data and information into various action modules and databases of the system. The filter 710a causes the information and data 902 to be reduced and segregated into appropriate plan sections 704. The segregated information and data 902 are saved and organized into appropriate classes and subclasses in the planning sheets 702. In one embodiment, the filter 710a receives all the information and data 902 including design parameters, selections and other guidelines provided or selected by the User in the Consultation package 404, the Inspiration gallery 406, the Design center 408, the Scrapbook 410 and from the information providers 412. The filter 710a then organizes and codes the information and data into actual plan sections 704 of the planning sheets 702. The information and data 902 are selected via filter 710a based on User selections made, for example, in the initial consultation. FIG. 10 illustrates an example of a user interface 1002 for the consultation used to prompt the User for desired guidelines and parameters. In this example, the information selected in the consultation engages filter 710a to distribute only real or related information and data through the filter 710a. In one example, if a User enters a guideline suggesting that all floors in the Project are to be made of wood, then the filter 710a ensures that all information and data regarding marble floors and carpeting is subsequently excluded and that only data and information related to wood floors enters and is organized into the planning sheets. It should be understood that the consultation may be later customized or modified and updated at any time during the construction project. Accordingly, the filter 710a is configured to update the data and information in the planning sheets to correspond to the updated data and information.

Figure 9B:
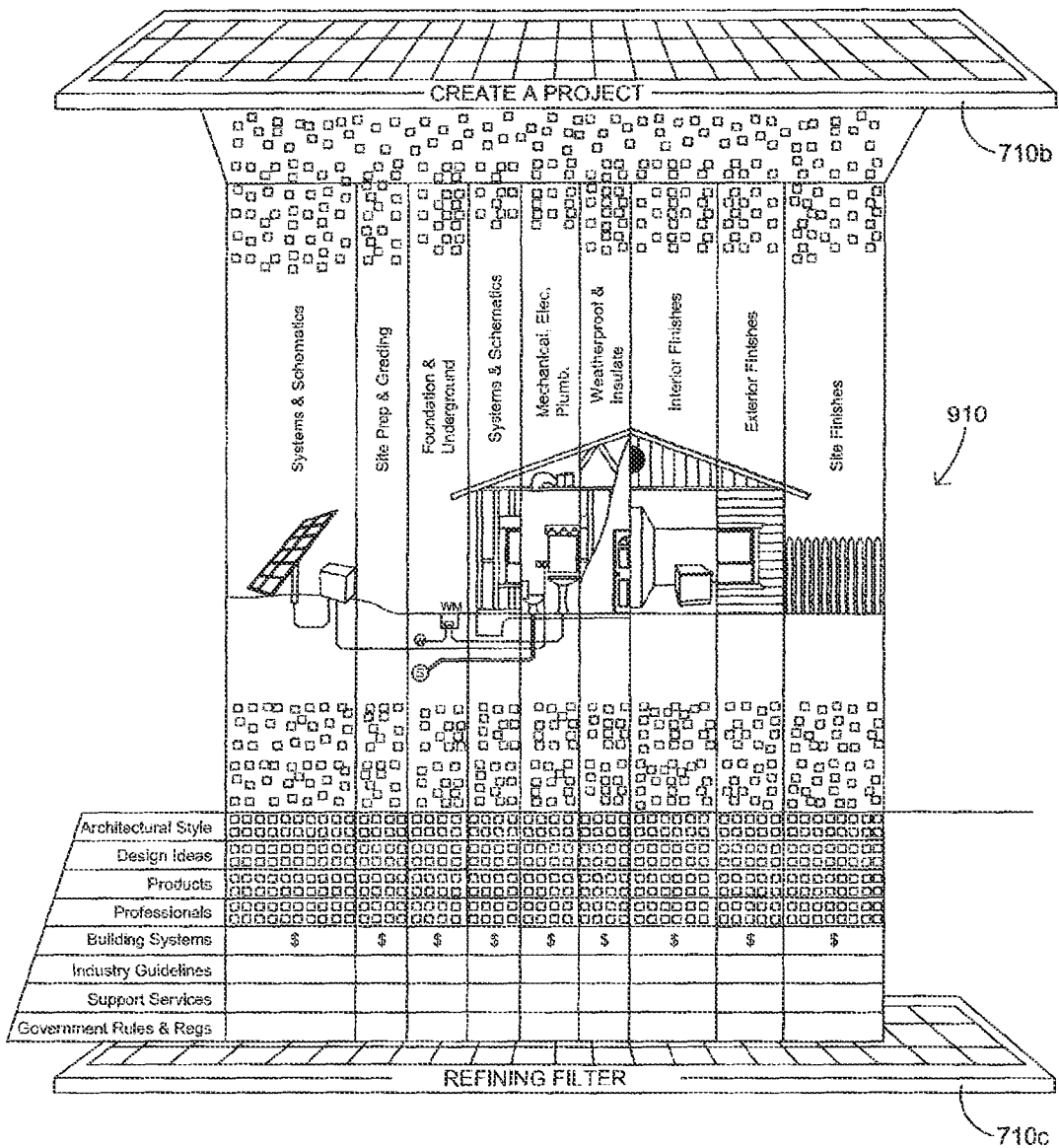

As shown in FIGS. 9A and 9B, in one embodiment, a second filter 710b is provided that takes the segregated information and data 902 and further narrows the information data into specific primary selections for a particular project. In one embodiment, the second filter 710b may arrive at the narrowed selections by for example, actual user selections made, further questioning of the User regarding specific choices and their compatibility, desirability and usability with other choices and/or the overall Vision of the project. The primary selections are stored in the primary results portion 910 of the planning sheets 702.

Referring again to FIG. 7, once the primary results portion 910 of the planning sheets has been filled with the primary selections, the user may choose to revisit various selections and make changes or modifications. However, at this stage, the filtering mechanism 710b has narrowed the information and data to a comprehensible selection of products, photos and options. The information in the planning sheets is now ready via further refinements through filter 710c made because of the interactive collaboration with other users (FIG. 9B) for use in the Vision Album, Project Guide and Project Journal as described below.

As illustrated in FIG. 7, the building system 200 uses the information saved and stored in the planning sheets 702 to guide the Owner 202 to develop the Vision album 208. The Design team 204 uses the Vision album 208 in collaboration with the Owner 202 to further refine via filters 705 and modify the information and data in the plan sections 704 to develop the Project guide 210. The Project guide 210 is then provided to the Build team 206, which ultimately bids and constructs the project based on the ideas and plans set forth in the Project guide 210 inspired by the Vision album 208. The Build team 206 creates the Project journal 212 that incorporates all the actions taken and other final information and data associated with the Project. In combination, the Vision album 208, the Project guide 210 and the Project Journal 212 are combined to form the Project portfolio 214—a Users Guide for the Owner 202 and subsequent owners and managers.

Thus, the technical features of the computer-implemented process for generating a project planning document may include mechanisms for presenting queries prompting responses relating to a project type, the responses provided by a first user in generating a first set of data; filtering the first set of data and populating segments of a planning sheet with the filtered first set of data based on project preferences defined in the responses to the queries, the filtered first set of data included in a planning guide; modifying the first set of data in the planning guide in response to interactive and collaborative queries made between the first user and a second user to create a project guide having a second set of data; and recording progress of an implementation by a third user of the project guide to create a project journal. The project journal may include actions to be taken in implementing a project based on at least portions of the first and second sets of data in the planning sheets. In a still further example, the project journal contains schedules, projects tasks, contact information, manufacturer information, and pictures. In one example, the second set of data contains less than 90% of the data from the first set of data. In another example, the second set of data contains less than 50% of the data from the first set of data. The change in the second set of data from the first set of data is due, at least in part, by the collaborative interaction between the first user and the second user, which includes any other person, group or party who is invited to comment on, share ideas and information on the project, in some cases, the second user is located in a different geographic location, such as a different state from the first user. In another embodiment, the second user is located in a different country from the first user. In yet another embodiment, the second user is located in a different continent from the first user. However, the first user and the second user can always be located in close proximity to one another. The system has the ability to permit access by users or members that are in close proximity to one another or at remote locations from one another.

Advantageously, since all work is recorded and stored in the planning sheets and subsequently output in the reports or guides, lost information, miscommunications and misunderstandings may be reduced or eliminated between User Groups. During each phase, the planning system may be configured so that only one User Group has the ability to record final data into the planning sheets. However, all of the members of a User Group have the ability to access the Project and input data into the planning sheets. When there is consensus between required members then the lead User of that phase enters the final data, (the owner/developer) into the Vision album 208, the Design team 204 into the Project guide 210 or the Build team 206 into the Project journal 206. In another example, different member combinations can edit and record data.

The planning process developed through the building system 200 provides the advantage of allowing complete collaboration by various Users from anywhere in the world with access to the www. Thus, if the Owner 202 wishes to make a change at any time during the Project then the change can be updated into the appropriate output guide. In light of the availability of mobile phones or handheld computers with internet access capability, changes may be made or acknowledged almost instantaneously. For example, if the change is made during the design phase then the change is noted by the Design team 204 as part of the Project guide 210. If the change occurs during the construction phase then it is journaled by the Build team 206 and shows up in the completed Project portfolio 214. Thus, the planning system allows for project collaboration between the entities involved in the building process. The project collaboration results in a project that transforms from a first state to a second state or to a third state and wherein the second state and the third state differ from the first state by at least 10% or more. By different in state, it is understood to mean different in concept, design, or implementation that would require at least 10% or more man-hours to modify from the first state.

Figure 14A:
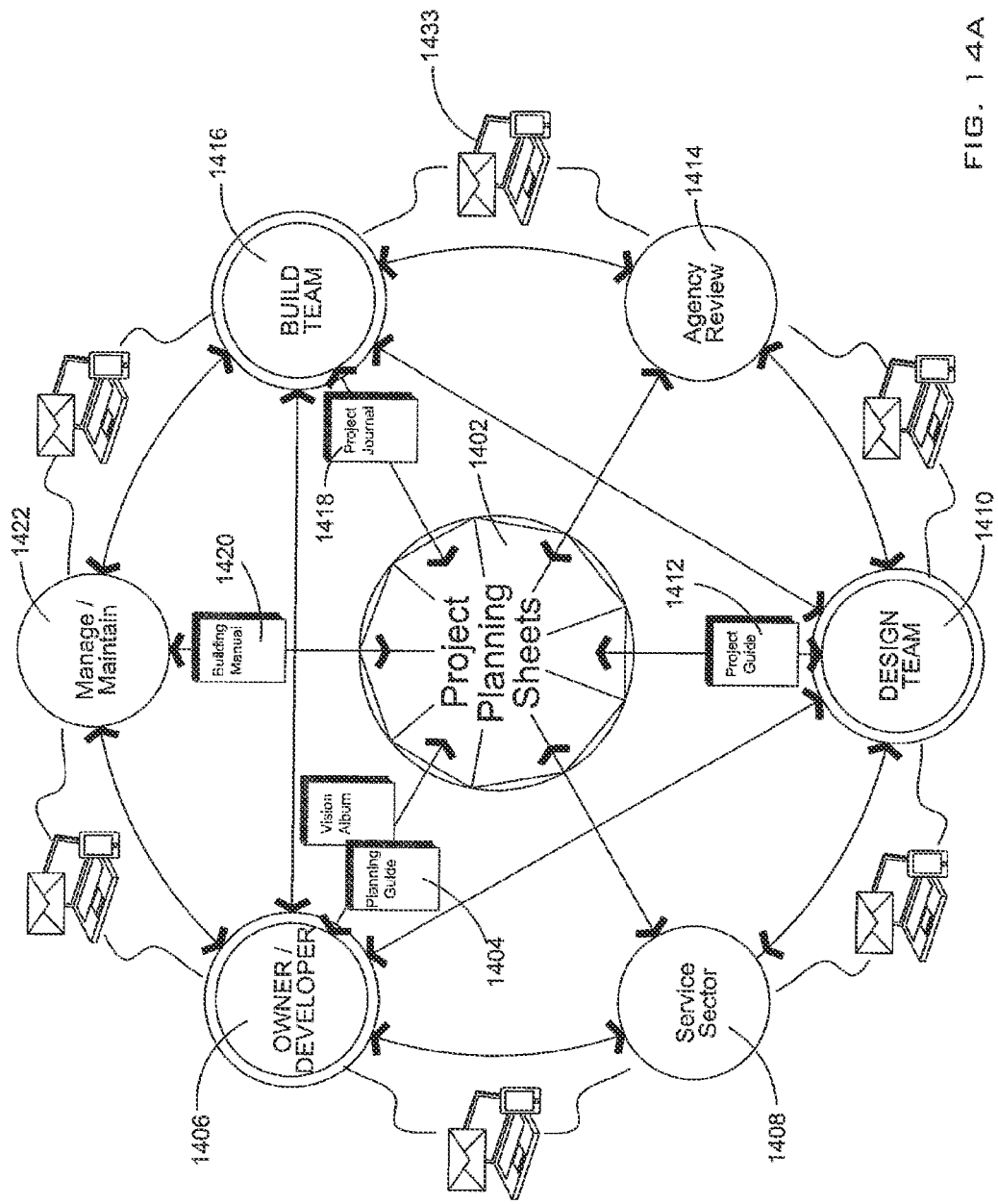
FIG. 14A is a diagram representing the interaction between user groups of the building system according to an embodiment.

FIG. 14A is a graphical representation of the project collaboration between the various users of the planning system 1400 (used as the building system) using the project planning sheets 1402 as the framework that permeates through the entire planning process as described above. The graph in FIG. 14A is intended to highlight the interactive and collaborative capability that the building system 200 is able to provide while a project is being developed. Since all inputs, changes, and modifications are recorded and stored in the planning sheets 1402, the Owner/developer 1406 (Owner 1406) is able to interact with the planning sheets 1402 to develop the Vision Album/Planning Guide 1404. As shown in the graph, advantageously, throughout the planning process, the Owner 1406 may be able to interact and transact business with others who are figuratively in-the-loop as they are able to be kept abreast of the project planning. The Owner 1406 may be able to interact with Service Sector providers 1408 while development of the planning guide is underway. The Service Sector providers 1408, which may include insurance brokers, bankers, appraisers and the like, may be granted access to the planning sheets 1402 so that while a project is being developed, these providers are privy to the actual progress being made on a project. This information helps the Service Sector providers provide their services to the Owner 1406 in a timely and effective manner. For example, the Owner may be contemplating building a two-story building. The Owner's selections as they relate to the proposed building and stored in the planning sheets may be accessed by an insurance broker who may review the Owner's actual selections (e.g. square footage, masonry building, fireproof materials used) to provide an accurate quote based thereon. Subsequently, the Owner may change the plan to include only a single story building. The insurance broker may be notified of this change via email, text or other alert and may again access the planning sheets to determine how the project has been modified so as to provide an updated quote to the Owner.

Next, the design team 1410, which may include, for example, land planners, engineers, architects and the like, has a communication link to the Owner 1406 as well as a link through the planning sheets 1402. This interactive collaboration between the Owner 1406 and the Design team 1410 directly and via the planning sheets 1402 leads to the development of the Project guide 1412. However, as the graph illustrates, the Design team 1410 may also have a communication link to the Service Sector providers, who also maintain a link to the planning sheets 1402 and the Owner 1406. These links allow for continuous collaboration between the groups so that all are aware of the continuing progress of the project. In this way, each group can provide their respective services using the latest information available. In one example, the Design team 1410 may have a communication link to outside agencies 1414 that may be used to review a project for compliance with local ordinances and the like while the Design team is preparing specifications and plans. The outside agencies are also granted access to the planning sheets 1402, so that the agency is able to view the project plan directly. In another example, the system sends electronic messages 1433, such as texts, emails and the like to one or more members of the outside agencies, design team members, and providers to log into the planning sheets and project guides to provide input.

The electronic messages 1433 may be self-triggered based on predetermined criteria or triggered by any one of the members and users.

The Design team 1410 communicates directly with the Build team 1416 to relay the project guide 1412 to the Build team so that implementation of the project may commence. The Build team 1416 has access to the planning sheets 1402 and maintains a direct communication link with the Owner 1406 and the outside agency reviewers. The Build team records their actions taken to implement the project, which are maintained in the Project journal 1418. Again, each group is kept in-the-loop via the planning sheets 1402 and other direct communication links so that as the project progresses, each component of the group can maintain an updated outlook and provide updated services as needed. For example, the Build team may require a change due to an unforeseen circumstance in the building plan. The remainder of the groups would be alerted of the change. Each group could access the planning sheets, review the change and take appropriate actions if required.

Finally, all of the information compiled in the planning guide 1404, the project guide 1412, and the project journal 1418 are assembled or recorded into the Building Manual 1420. The Building manual 1420 may then be accessed by the Owner 1406 or by a building/property manager 1422 that now has access to all information related to the building that has been compiled from the beginning to the end of the project. Thus, if the manager needs to coordinate for example, repair of the HVAC system in the building, he can access the Building manual 1420 and determine which sub-contractor installed the original HVAC system and is then able to determine if the HVAC system is still under warranty.

FIG. 14B is a graphical illustration of the overall components of the planning system 1400 in accordance with an embodiment. In the data and information aggregation and distribution phase, the data and information enters the system via data filter 1504 of graph 1500. The data is then accessible by a user who can use actions modules, such as the inspiration gallery 1436 and the scrapbook 1438 to review the data and information. As previously described, once the User enters the site via the planning kit 1440, the User is given the opportunity to enter project specific data and make decisions that engage filters that control the flow of data through the site to populate the planning sheets 1442. The filters are engaged by selecting building type, for example, Residential, Commercial, Industrial, Multifamily, Live/Work, Midrise or Highrise and the like. The User also may be asked to select a project location through a map or zip code that may specify climate type, an architectural style if desired, and the like. Each of these decisions engages the filters that allow the system to select, sort and deliver the photos, materials, products, systems and services that suit their specific needs. Thus, the user will not be shown the entire database, but rather those parts that the user not only may need to see but also should see, since the planning system does not just deliver choices but also suggests them.

The building system 1400 provides, for example, Architects, Builders, Contractors, Developers and Engineers (collectively, the Professionals) with project pre-planning and proper-planning options by allowing the Professionals to select and purchase competitively priced building products using the Bid Room 1424 through all phases of the construction project including selection, purchase and delivery of these products, thus enabling the Professionals to spend less time to complete their projects and for less money.

The building system 1400 provides visual tools and easy to understand instructions so that Professionals, as well as project owners and developers, may purchase environmentally friendly (Green) products, services and systems. Users may be offered user discounts, rebates, and other incentives and benefits from product, service and system providers 1500 (see FIG. 15A) using professional showcase 1426, network listings 1428, service listings 1430 and manufacturers showrooms 1432, for example. These tools may be provided on-line via the www. Thus, since the tools are available on-line, construction projects may be planned by the Professionals located in one country while the construction occurs in another country.

Beneficially, in one embodiment, Users of the building system are provided the ability to print out or email preformatted purchase orders and project specification sheets for reference, pricing and documentation to show to other project team members. The system also offers the ability to order product samples or the User can visit a product selection site where they can touch and feel the items being considered. The completed project data in the completed Project Portfolio can be stored on site, stored on CD or printed in book or binder form, then retrieved later for maintenance or upgrades or future renovations as well as advertising and/or selling, for example, the quality, the efficiency or even the greenness of a home/building. The planning system may also include company sponsored product and information centers where users can get assistance with or be allowed to see and or feel products and discuss services.

The planning system 1400 provides for ordering tools 1434 which allow for the renting or buying of equipment and or tools and for the procuring, packaging and shipping out of finish packages, for example, using preformatted purchase orders, such as electrical finish, plumbing finish, appliances and the like, to the job site for subcontractor installation. This process can be done on-line, thus eliminating the need for physically driving to a store or warehouse. Thus, a User can access virtual storefronts 1434 that represent eCommerce sites, retail outlets and wholesale distribution centers. Groups of Users may be able to form Co-ops in order to make bulk purchases of products and services.

Figure 14C:
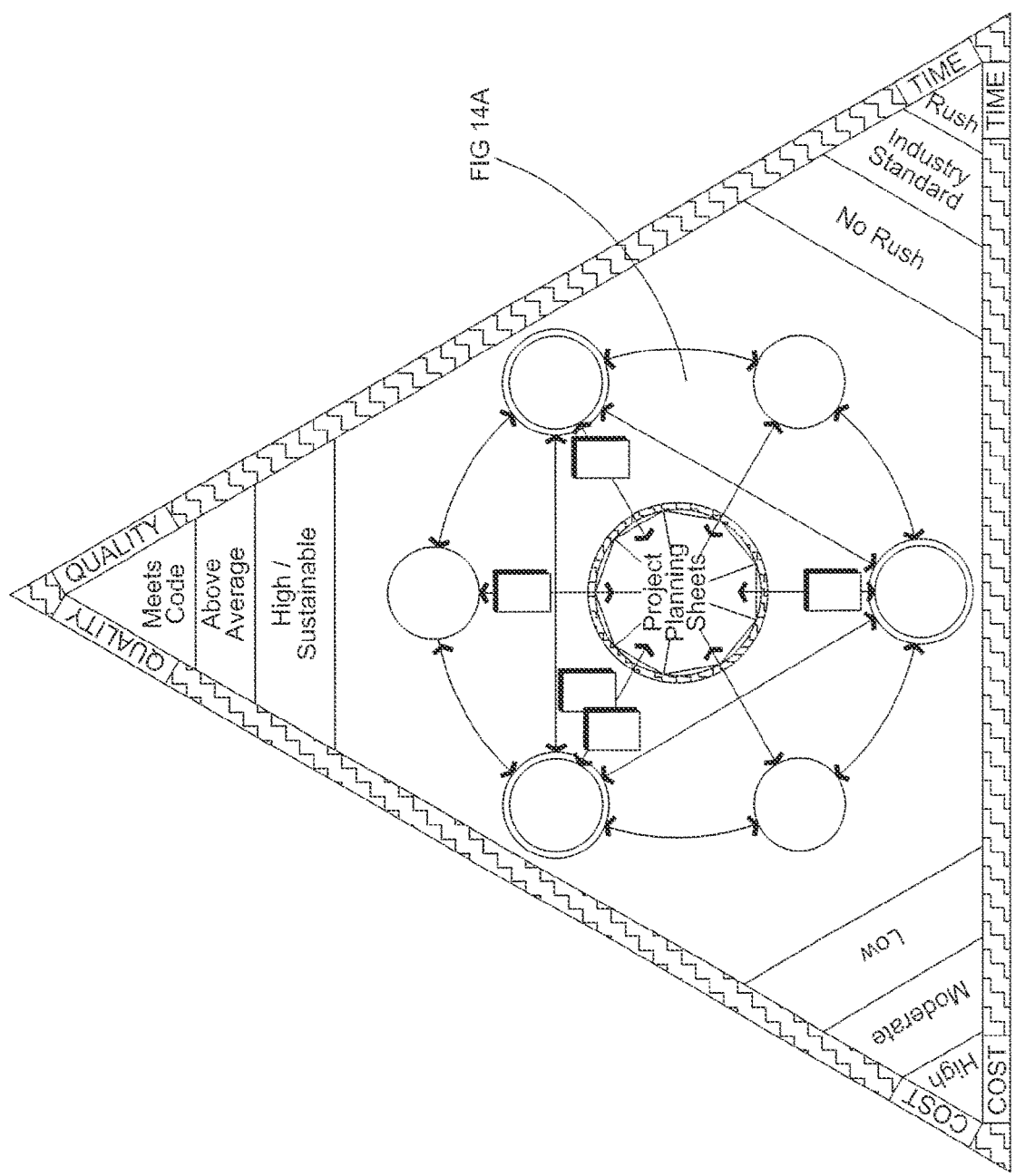

As shown in FIGS. 14B and 14C, a cost/time/quality filter 1450 may be implemented as part of the project planning system. Typically, the filter 1450 is applied as the user is setting guidelines for the project, for example, during the consultation. However, this filter may be subsequently engaged. The filter allows at least three criteria, cost, time and quality, to be addressed by the user. In one embodiment, the user may select to require various degrees or quantities of each criterion alone or in combination. For example, the criteria may be presented on a scale of importance or priority, such as on a scale of 1 to 5 or the user may be able to just make a selection of the range provided. Thus, if the user determines that cost is no issue to the project than products and services of all cost ranges (high, moderate and low) may be provided. However, if time is an issue and the user specifies that a rush job is needed, then the cost and quality components of the filter may be affected since not all cost ranges and quality ranges of products and services may be accommodated for a rush job. Thus, product and services that are in the lower ranges of cost and lower ranges of quality may be provided for selection by the user, since these may be done relatively quickly. In another example, if quality must be high, then the cost component filter is affected as is the time component filter, since a high quality job may typically not be rushed or done for low cost. Thus, product and services that are in the higher ranges of cost and done in no rush may be provided for selection by the user.

FIG. 19 is a flowchart illustrating one operational example of how the building system application may be used in accordance with one embodiment, however, this example is not meant to limit the scope of the planning system in any manner. In this particular example, a home owner/developer (owner) accesses the building system 200 because the owner is interested in having a custom home built for his family. The owner begins by registering into the system and providing information into the planning kit or the consultation package provided by the system. The consultation package inquires whether the owner is a Property Owner or Professional, about the purpose of the visit, and other demographic information. The owner may choose to "Create A Project", where the system delivers an initial consultation questionnaire so the owner may further define the project. Next, the owner may input or select "Residential" and "Single Family", may input Zip Code or a City name, and may further select a Climate Zone, for example, Marine Mediterranean Climate Zone.

The building system delivers a default set of planning sheets to the owner for the requested building type and climate zone. The system makes additional requests or prompts that are appropriate to the specific project identified by the owner. The owner continues to refine the process, and continues to input, for example, the numbers of rooms and baths, kitchen features, laundry features, garage features, detached "mother-in-law" room features, square footage desired, lot size, building features, architectural features, colors, wall systems, roof systems, special requirements and the like. The owner may be delivered additional information regarding completed projects in their area, the professionals who worked on them and the products they used in their projects.

The building system employs the various system filters to narrow the selections to a manageable and related number, thus eliminating information unrelated to the owner's preferences. The filters may include, for example, Architectural Style for Exterior and Interior, the type of Sustainability Filter, where User may select Solar Hot Water Heating and Structural Insulated Panel System. The building system further itemizes the owner's selections of Wall System Filter, Roof System filter, Room and Space Filter. The owner may not only specify the number of rooms but also how the rooms are to be designed by the "Room/Space Relationship Filter" where the owner may decide, for example, where the bedroom is to be placed relative to the bathroom, how close the kitchen is to be placed relative to the family room, and how far the master bedroom is to be place relative to the kid's bedroom or guest room. The building system may also provide a Feature Filter for selecting fireplaces and built-in entertainment centers and an Amenities Filter for selecting additional features, such as built-in ironing boards in the laundry room.

The owner at anytime during the planning of the project may search for products and services. The building system guides the owner through the process and provides additional information to assist the owner in making decisions in the project creation process. The building system may provide access to products and service based on owner's selections entered into the building system thus far. The building system may provide a Cost/Time/Quality filter (FIG. 14C) used to bring products and services to the owner that come closest to the owner's specified criteria regarding how much the owner desires to pay, how much time the owner has to build and what quality the owner desires, or some combination of the three criterion.

The building system uses brings design ideas, related products and systems, service professionals to the attention of the owner. The owner selects various images and products from the inspiration gallery or marketplace that develop the look and feel of the project. The owner also selects various links to outside information providers and vendors who provide showcases and the like of their respective products and services. For example, the owner visits the inspiration gallery and finds some exterior photos that show the look that the owner wants to capture in his home. The owner also finds some interior views with a desired layout for the kitchen, the finishes for the master bedroom, and amenities for the family room. The images selected by the owner link to a variety of data including the products used, the names of the professionals who did the work, and the cost of the project, for example. In another example, from the images, the owner is able to "click" on a roofing product that the owner would like to use. The project shown is located in the area and links to an architect and a roofer. The owner opens the professional showcases link from this project, learns more about the contractors and decides to save the image and the links to the contractors in the vision album. The owner also accesses the product marketplace and makes selections for doors, windows and light fixtures. Because of the filtering process based on the owner's initial inputs, the products provided for selection are just what the owner is looking for to use on the project. The owner continues to peruse the professional showcases and seeks feedback form the system about certain contractors. The owner is happy with his selections and saves them to the vision album.

Since the building system has a social/business network component, the owner provides access to the vision album via the planning sheets to his immediate family. The owner also sends a link to a sister-in-law who is a designer living in another state and to a brother who works for an architect and lives close by to the owner.

The people with whom the user shares the project may go into the building system and view the vision album. They each make some recommendations. For example, the sister-in-law searches the products directory in the marketplace and finds an affordable brand of hardwood flooring and paint colors that she feels would go well with the project. The brother lets the owner know that his firm has used a metal roofing that is a fraction of the weight and costs less than the roof that the owner had selected. The owner's children ask for built in work areas in their bedrooms and a larger shower in the shared bathroom. All of the recommendations are saved to the recommendations section of the vision album for later review by the owner.

The owner makes changes and updates to the vision album based on some of the recommendations as well as some additional selections that the owner made after seeing the home of a close friend.

The owner has decided that enough upfront planning has been done. The owner may now finalize the project selections for the time being and submit the project. The system delivers the set of planning sheets with a vision album template where the work is organized and stored.

The owner is ready to hire an architect. The owner has selected two architects and already stored their information in the vision album. The owner contacts both architects and posts the project into the system bid/inquiry room (FIG. 14B) to see if any others are interested in the project. The owner sets a due date for initial contact at 15 days out and requests for bid submittal at 30 days after initial contact. The bid room posting results in two additional architects expressing an interest in the project. The user opens the showcases of each architect and determines that one of them would be a good fit, the other seems too expensive and is not a local business. With three architects now in the running, the owner accesses preformatted forms from the building system including a formal Request for Proposal (RFP). The owner may checks boxes on the RFP that identify certain conditions of the agreement. Each of the three architects is given access to the vision album. During negotiations, each of the three applicants is able to make recommendations and further requests for data. The owner reviews the requests and posts updates on the building system, which notifies the applicants of the change. Each applicant makes a proposal based on the same updated information. The owner selects the architect who has created the best budget and schedule for the work to be performed. The owner accesses forms on the system that may be used to complete the contracting process. The architect has additional form requirements that he uploads into the building system that may then become part of the contract documents of the owner's building system.

The owner assigns the completed vision album to the design team, which includes the selected architect. The architect continues to access the vision album and planning sheets, which include a list of tasks, and components that need to be selected. The architect reviews the work that is already stored in the vision album. The architect notes that the owner requested use of SIPS and is interested in having solar hot water heaters. The architect has not used SIPS on any of his projects before so he posts an inquiry in the System Bid/Inquiry room to find out what effect SIPS may have on the cost and viability of the project. A general contractor, a framing contractor and a SIPS Manufacture respond to the inquiry. The architect is told that installation of SIPS is 70% faster than conventional framing methods, which reduces labor costs and speeds up the rough-in phase of the project. The materials cost about 15% more but offer superior insulating qualities so there is an attainable payback. The architect notifies the owner of his findings and continues with the design/specification process. Each of the components and tasks identified in the planning sheets needs to be addressed before the process is complete. The owner and the design team know that more collaboration now between the two users reduces the chance for cost overruns and increases the possibility that the project is successful.

As the design phase progresses, the architect give each of his peers and other consultants access to the project planning sheets. The structural engineer recommends an alternative roof truss that costs less than the truss system already being considered. The owner continues his research using the building system and finds schematics on passive efficiency and sustainable methods. The owner notifies the architect via the system email that he would like to incorporate natural day-lighting and natural ventilation into the plan. The architect designs skylights for the appropriate areas and includes awning and transom windows into the plan to achieve a ventilating stack effect. The architect also recommends an air filtration system and water saving devices that his team recommended. The architect collaborates with the entire design team and the owner until the choices are fully vetted and everyone on the team is pleased with the design and functionality that have been specified during the process. The planning guide is completed with all building systems, products and finishes having now been selected.

With a completed planning guide, the owner is ready to hire a builder. The owner has continued to search through the inspiration gallery and the professional directory and has found several builders who specialize in his project type. The owner and the design time consult. The architect has used one of the builders in the past with good success. The owner decides to put the project into the bid room using a semi private mode and gives access to three builders now under consideration. The builders are asked to provide a fixed bid and schedule. The builders having accessed the planning sheets know exactly what the project entails. The bid process is done systematically and efficiently through the bid room since all of the details are readily available to the builders. Each builder has the ability to post questions or concerns to the owner and the design team. The updates to the project are posted in the Bid Room so that the participants are working with aggregated up-to-date information. A builder is selected, the sealed project guide is transferred to him and construction begins. The builder is now responsible to schedule the work, document the process and insure quality workmanship and installation. The build team has a substantially complete set of specifications that are linked to the products to be used. The products are linked to preformatted work orders and instructions where the products may be purchased in the local area. Some of the vendors are part of the building system co-op group that recognizes and gives valuable discounts to building system members. Tools are available to the builder and subcontractors that guide them in executing their processes.

The builder uses the Bid Room to process his subcontractor, specialty contractor and materials bids. Each person or entity participating in the bid room process is granted access to the building system. The building system includes forms, including preformatted purchase orders, requests for information, requests for bids, requests for payments, lien releases and the like that are automatically tied to the project and may include preloaded information. Contractor invoices for work done, permit approval process, payments made, payments due and balance of contract may be tracked by the building system to maintain accountability between all parties. All of the sub- and specialty contractors are given access to the project planning sheets, which uses a budget and schedule component.

The builder tracks the work and actions taken in the building system and documents information that serves the owner or the owner's manager or maintenance team, where appropriate, for the life of the building in the project journal. If the building system is used to purchase the products, the building system automatically documents product data. If not, then the builder is asked to input manufacture, recommended/suggested and mandatory maintenance products and schedule, warranty information, product registration confirmations and contact persons who are able to do the work when needed. Product warranty and maintenance information may be recorded or uploaded into the project journal.

Once the project is finished each of the vision album, the planning guide, and the project journal may be assembled together in a final project portfolio/manual and presented to the owner. The owner is pleased to have a project manual that lives with the project. For example, the maintenance records are digitally monitored and documented. Each time a work order is generated, the owner is able to access the required information including product data, recommended cleaning products, scheduled cleaning and coating processes, and the people who do the work in the local area. The building system notifies the owner by way of electronic system email when a maintenance event is scheduled to occur. The building function is maintained and product life is extended due to proper care. When the owner decides to sell the house, the new buyer may be given the project manual to have a clear understanding of the entire property and the professionals involved with its creation.

The embodiments described above provide an implementation of the planning system as a building system that applies to the Project Planning/Designing/Building Construction industry. However, the description set forth below illustrates the technical features and the steps for using the planning system in connection with other embodiments and other applications. For example, the technical features of the planning system may be applicable as a project system in the travel industry, the real estate industry, the educational industry, and other service related industries, including governmental agencies such as zoning and planning commissions, employment placement agencies and health care and social service agencies.

Generally, customers or consumers of most services are provided with lists of products, options, available information, tips, resources, vendors and the like that the customer or consumer might use to make selections regarding the particular service. The selection process and complexity associated with managing the selection process is increased due to the large number of options that may be made available to the consumer. Typically, a large number of selections may need to be tracked in order to preserve the consumer's general desires. Even though consumers may be inundated with large amounts of information, options and the like, the consumer still may not receive sufficient information or other data that is actually related to his or her specific desires, wants and needs. In some instances, the consumer may not even be aware that certain options even exist.

Figure 16:
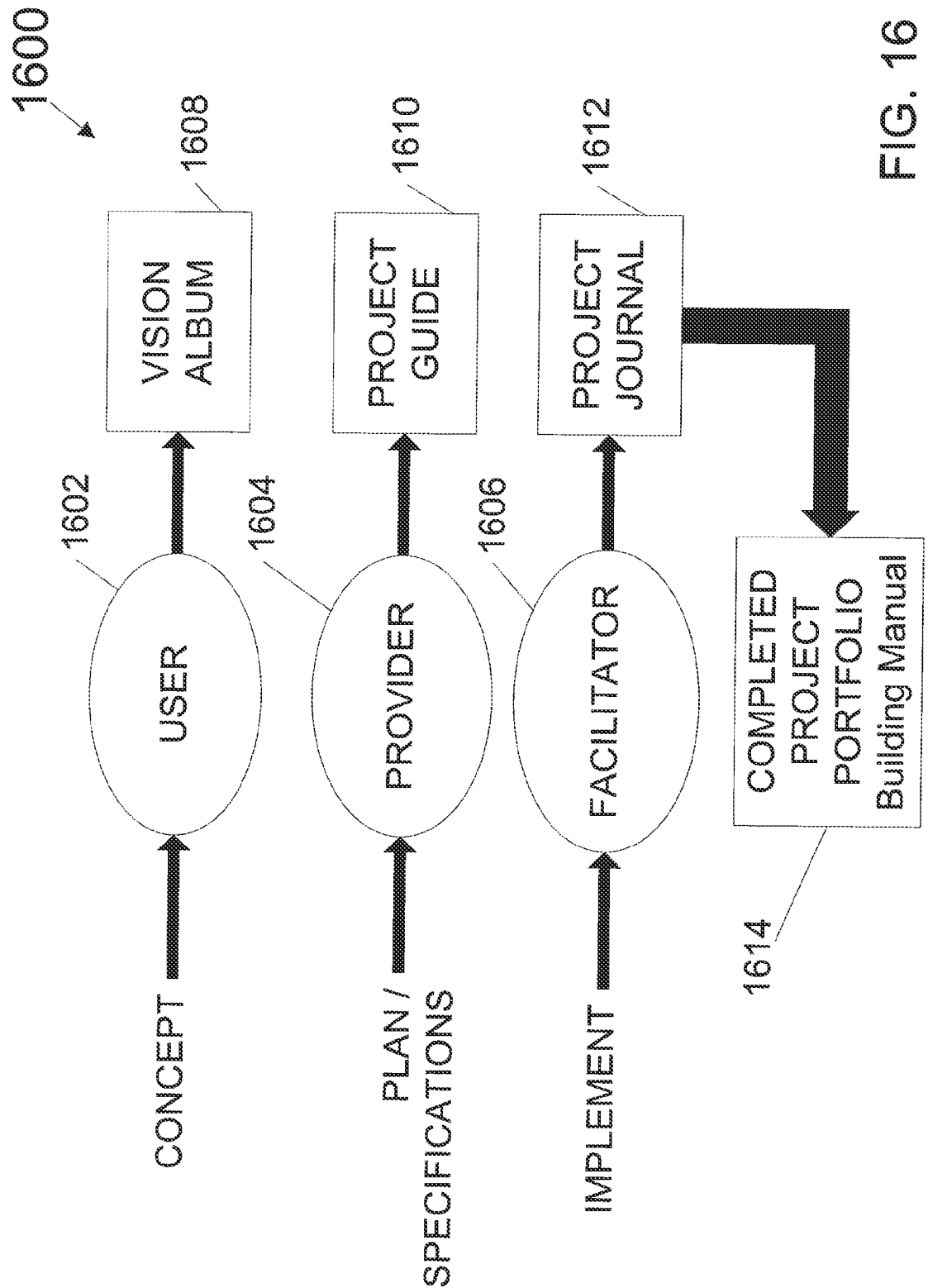
FIG. 16 is a diagram illustrating a planning system including a process that allows a user to create a custom project in accordance with an embodiment.

FIG. 16 is a diagram illustrating a planning system implemented as the project system 1600 including a process that allows a user to create a custom project in accordance with an embodiment. As used herein, a custom project may be understood to include any planned undertaking, for example, without limitation, traveling, developing an educational syllabus, purchasing or selling real estate, college planning, retirement planning, career planning, community planning and any other undertaking that may require the need for at least one of conceptualizing, scheduling, refining, adjusting, modifying, testing and implementing, and any project where multiple participants or groups are or could work together for better project outcomes. As further discussed below, by using the process provided in accordance with aspects of the present disclosure, users are able to design, plan, and manage their custom project, for example, on-line from almost any internet connection in the world, via telephone or any other similar means of communication. The process takes input from the user and organizes it for various other groups to review, comment, suggest alternatives and refine the information. In one embodiment, various database modules, including photos and other media are provided to suggest alternatives for user selected refinements. In addition, based on selections made by the user of certain information, the user is offered additional information, options and choices, which lead the user to the final product.

The project system 1600 allows each user group to generate guides, albums or portfolios that are created to facilitate the progression of a user's project from concept, through design and planning to final implementation and maintain and manage the product or project in an interactive, collaborative and innovative process. The guides may constitute a physical compilation of data, storage cd or print versions or alternatively, the guides may be a virtual (electronic) compilation of data. The guides may be used individually or in conjunction with each other. The guides represent the Output created by the interaction and collaboration of each group within the project system 1600.

As shown in FIG. 16, a project system 1600 divides the conceptualizing, planning and implementation of most any project into various phases. In one embodiment, the phases may include a user or user group 1602, a provider or provider group 1604 and a facilitator or facilitator group 1606 that perform the functions to be achieved during a particular phase of the planning process. As described below, each of the groups has certain needs, skill sets and responsibilities in the planning process, as well as responsibilities and obligations to the other groups. Although, each group is described as having certain individual responsibilities and functions during certain phases, some functions and responsibilities may overlap.

The user or user group 1602 includes an individual, a client, a consumer, a customer, a project leader, a professional planner and the like, that typically initiates the want or need for the project. The user may set the initial parameters and guidelines used to describe the overall concept of the project. In one embodiment, the user may begin the process of creating a vision for a project by hiring a consultant, using a friend or family member or other third party to do the initial creation of the project vision. Afterward the user may critique and fine-tune the vision until satisfied. The needs, wants, parameters and guidelines of the user 1602 are compiled in a first portfolio 1608. The first portfolio 1608, which may also be referred to as a vision guide or vision album 1608, is initially created by the user 1602 during the concept phase of the project. In one embodiment, the user may interact with various interactive modules, which provide conceptual design elements to the user, to input, select from, and clarify the user's conceptual design elements so that the project may benefit from feedback, suggestions, and ideas provided by yet other interactive modules. The interactive modules provide a set of consultations that are used to inform the initial user of possibilities and options within the range of interests that the user has decided to explore.

In one embodiment, the interactive modules allow for a social aspect of collaboration and comment on a project, for example, by allowing alternative choices to be made, offered or suggested between friends, employees, colleagues and family members who might have an interest or have been invited to participate in the conception of a project. For example, a user may be using the project system to create a travel plan. The user accesses the interactive modules and interactively makes selections that outline the general wants and needs for his trip. Others who have been invited to participate in this phase of the planning may gather additional data from the system or upload various photos of their trips and vacations or other information about locations and travel tips. The user may then interactively view these suggested alternatives to change, modify, or refine his own selections.

In one embodiment, the user 1602 communicates its needs, wants, parameters, and guidelines to the provider group 1604 via the vision album. Communications between the user group and the provider group may include links to different databases and links to provider accounts provided on a website, and/or links between a computer and other communication devices, such as cell phones and fax machines.

The provider group 1604 may include one or many professionals or others who possess the expertise or information, including databases of information, who may be hired by the user group, or at least made available to the user group as a resource, to design and create the second portfolio or project guide 1610. The project guide 1610 is created by the provider group 1604 upon review of the selections made and set forth in the vision album 1608 by the user group 1602. Thus, the project guide is user defined project parameters that have been refined through communication and collaboration with one or more providers based on, at least in part, the experience and the expertise of the one or more providers.

The second portfolio 1610 may also be created using a system of queries or consultations and filters, described below, that are used to fine-tune a project to ultimately ensure that the project continues to inform the user group and reflect the needs, wants and desires of the user group 1602. Like the user group, the provider group may interact with various interactive modules, which indicate to them the conceptual design elements that the user group has selected. The provider group then uses all the parameters, guidelines and initial selections for the project to make additional queries of the user group to further refine, optimize and possibly expand the parameters.

In addition to queries, the user group may be offered unsolicited information from the provider group. For example, certain selections made by the user group in creating the vision album may prompt the provider group to offer information that is related for further consideration by the user group. Certain targeted queries made by the provider group, in conjunction with the additional unsolicited information may cause the parameters and guidelines that were initially used to create the vision album to change. Thus, the user group is allowed to interactively, along with the provider group, change or modify the vision album at anytime during the query phase of planning. However, while the project has been refined, the fundamental desires, wants and needs of the user group are maintained due to the involvement of the user group in the collaboration.

The provider group 1604 communicates and collaborates with the user group 1602 to refine on an iterative basis and make the selections made during the query phase of the project system final. The final selections are then incorporated into the project guide 1610 upon approval from the user group.

The facilitator or facilitator group 1606 may include one or many professionals or others with the appropriate skills that may be hired or made available to cause the project to be implemented in the manner requested by the user group and as designed by the provider group 1604. The method or rules of implementation may be compiled in a third portfolio 1612 or project journal 1612 and used to track the processes and progress of the project. The facilitator group 1606 is responsible to provide to the user group 1602 a quality completed project that reflects the user group's vision, needs, wants and desires for the project. In some embodiments, the provider group 1604 and the facilitator group 1606 may be the same professional or group of professionals depending on the type of project involved.

The final output of the project system 1600 is a completed project portfolio 1614. The completed project portfolio 1614 includes information that has been generated from the vision album 1608, the project guide 1610 and the project journal 1612, as well as any other information related or used in the planning process that may assist with the future success including maintaining, managing and performing the project. The completed project portfolio acts as a user's guide, or a reference book to the project. The completed project portfolio is designed to stay with the project, from user to user of that project where appropriate or with the original user as a record of the project plan.

The interactive modules previously mentioned may work as independent modules to allow the user group to design, plan, track and build his or her own customized project. When used to create a project, the interactive modules help to limit the information pertinent to the choices made by the user group in order to drive the selection process to creation of a final vision or concept. The interactive modules may also include their own set of tools and features, as further discussed below.

Figure 17:
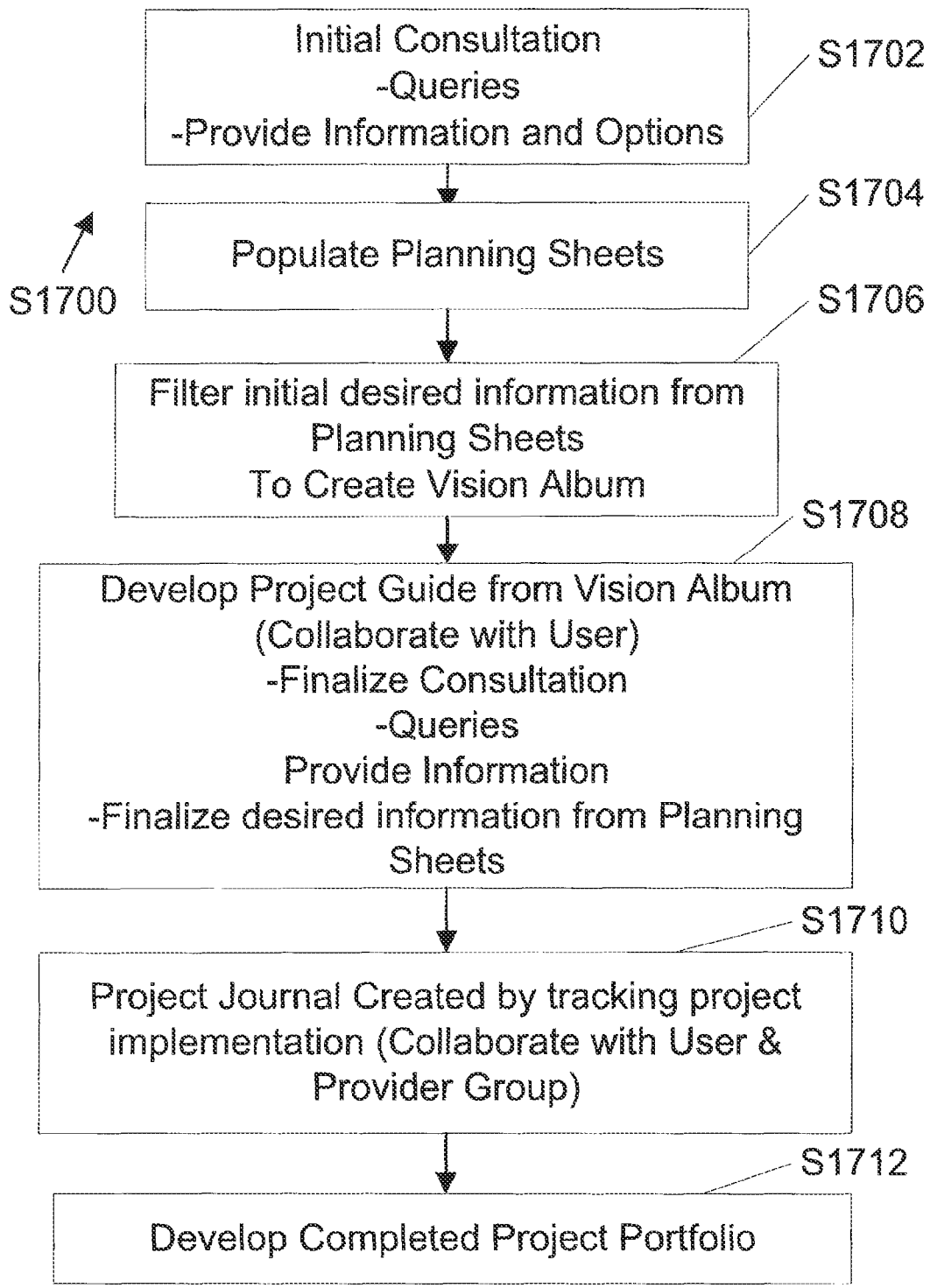
FIG. 17 is a flow chart illustrating a process for the planning system in accordance with an embodiment of the present disclosure.

FIG. 17 is a flow chart illustrating a process 1700 for the project system 1600 in accordance with an embodiment of the present disclosure. In step s1702, the process begins with the user making a general query regarding his or her project. The user also provides information regarding the concept or vision for the project, which may include project criteria and guideline information. The information may be entered into project system 1600 using any well known user interfaces, such as the following non-limiting examples: a graphical user interface via fillable forms, selectable lists or images, prompts, icons, and an interactive interview process.

The project system receives the initial query and provides a consultation, which may be in the form of specifically targeted requests, intelligent checklists, responses to questionnaires, selections from drop down or popup menus and similar forms of query, to develop the vision album. In one embodiment, the consultation provided to the user is in the form of a preformatted outline that is designed to consider possibilities related or specific to the undertaking that the user is pursuing. The possibilities are generally in the form of options that once selected start the process of formulating a path for creating the vision album. In some cases, the user may be given the choice to prioritize, for example, A, B, then C. By engaging in this process the user is able to set and establish project guidelines and parameters. The project guidelines and parameters, in turn, set the boundaries for filters used within the system as described below. In some cases, by selecting one option the system may in turn eliminate or include others.

Initially, the information provided by the user regarding the project is received into the project system 1600 via the planning sheets. The planning sheets are created and populated by the project system to organize data for retrieval and storage by the user (s1704). The planning sheets also provide a means to classify the parameters, products and processes generated by the user group and provider group. The planning sheets may include the information, broken down or separated into phases or sections related to certain choices made during the planning process. In one embodiment, the sections may be filled using, for example, the intelligent checklist provided to the user during the initial consultation. In this embodiment, the checklist allows the user to enter the project criteria and parameters and guidelines. The selections may be further divided and organized into sets of classes and subclasses for further categorization of the information. As described below, the planning sheets provide a means for conveying the project information through the concept, the query and the plan phases of the project system as the information is compiled and generated for access by all of the groups as the need arises. In the planning sheets, products, services, systems and the like are categorized and may be selected using a systematic approach. In one embodiment, the planning sheets provide a visual tool that allows professionals, as well as project owners, the opportunity to view, select, store for review and purchase products, services and systems through each segment of the project. The planning sheets act as a tracking device so that no design element or building component is missed in the planning phase.

In accordance with an embodiment, the data compiled in the planning sheets is filtered, organized and parsed to begin the development of the vision album (s1706). Various filters are used to synthesize the information being gathered in the planning sheets into a compilation of data that at least reflects the initial wants, desires and needs of the user group. The compilation of the information creates the vision album. In one example, the user group is able to take their process as far as possible, that is, as far as they have time for or feel comfortable doing. When the user group is through with their processes, it may print a vision album or create a computer disc and pass the control of the project to the provider group. The printed copy presents the information, data, products and the like, which will help to serve the next user group in line.

Next, in step s1708, the provider group uses the information provided in the vision album to begin development of the project guide. Based on the information in the vision album and in collaborative discussions with the user group, the provider group offers information and services on the topics and other points of interest that may be associated with the information provided in the vision album. The discussions include making queries of the user group, which may seek more detailed information on a topic or else may prompt the user to consider yet unspecified options. The queries are used to further refine or even substantially change the selections shown in the vision album. This allows the project to be refined based on original entered data from the user group, but modified by information and data gathered in the collaboration between the provider group and the user group.

The provider group continues to interactively collaborate with the user group until it is decided by the user or between the groups that the discussions have yielded a final design of the project. The information now held in the planning sheets includes the final assessment of the needs, wants and desires of the user group, which the provider group compiles into the project guide. In one example, the provider group may perform a Save-As of the vision album on the project system and start refining, collaborating and gathering the completed design specifications. When the project guide is complete the control of the project can be given to the facilitator group who are able to, for example, bid, schedule, and design the project from the vision album.

The vision album, which includes the final design of the project, may now be viewed by the facilitator group who are charged with causing the plan to be readied for implementation. The project guide serves as the blue print for carrying-out or completing the project in the project guide, if and when the user group is ready to do so.

The steps for implementing the plan and the actions that are undertaken to complete the project are captured in the project journal (s1710). The project journal is created by tracking project implementation as a collaborative effort between the user group, the provider group and the facilitator group.

It is expected that during the facilitation (build) process of any project or product that some items may still need to be selected. Changes, additions or deletions from the design specifications listed may also occur. In one embodiment, the project journal is to track the actual implementation of the project.

Finally, the project journal along with pertinent data from the vision album and the project guide are seamed together in the project system to produce the completed project portfolio (s1712). The completed project portfolio provides a roadmap that brings the development of the project from conception, through design, to final implementation. The completed project portfolio (CPP) represents an embodiment of the finished project, like a user's guide or an owner's manual. The CPP may be used for the life of the project or product to maintain and manage the completed project. The initial user group or project owner may be able to go back into the CPP to find specific data on any component of the project, when and if needed, with the user able to resurrect a procedure performed or take a course of action that is required, needed or desired at the time with the least amount of effort. In one example, a user may have had a painter paint the walls on the interior or exterior of a house that was the subject of a project. Using the project system, the user would not have to guess or color match the paint for future touch ups. Instead, the CPP would provide the information necessary to order the exact paint that is needed. The same would apply in finding a match for a particular carpet that the user needs for a repair.

Figure 18A:
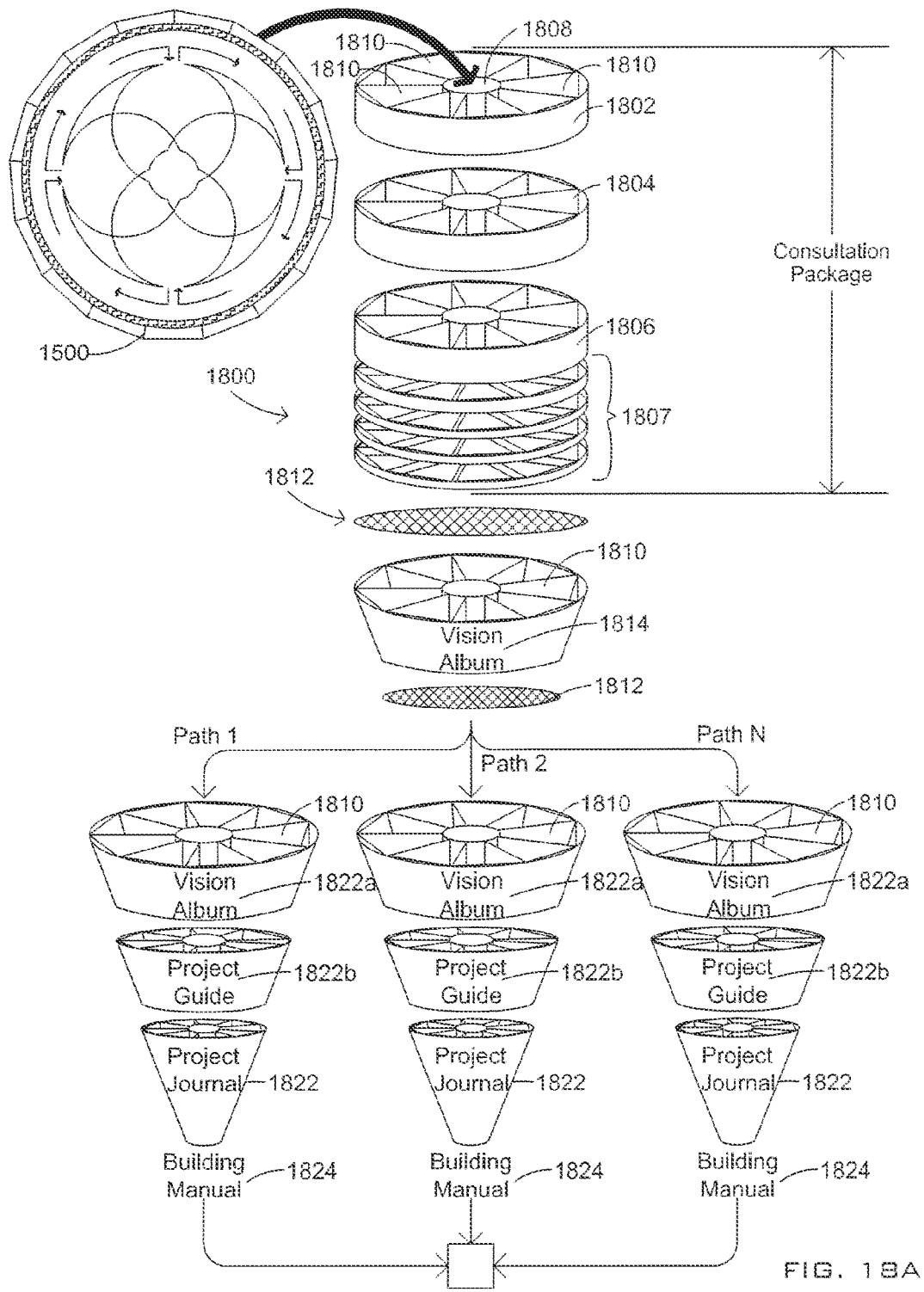

FIG. 18A provides a diagram illustrating a view of plan, management and communication segments involved in using the project system 1600 in accordance with an embodiment. The diagram provides a visual representation of how information is fed into each segment from a previous segment and into the working modules of the project system to provide the completed project portfolio in accordance with the embodiment.

For purposes of illustration and example, when referring to FIG. 18A, the description of the processes involved in the project system 1800 is described with reference to retirement planning. That is, the user group consists of a person who desires to undertake the project of creating a retirement plan. In this example, the retiree is a 50 year old single person who desires to retire at age 62 from a career as a school teacher.

In operation, during the project conception phase, the retiree is presented with a planning kit or consultation that includes interactive modules, such as, but not limited to interactive modules 1802, 1804 and 1806, that provide information regarding the concept or vision for the project. The modules also receive input from the retiree as the retiree populates, for example, a checklist, a dashboard or selects icons, pictures or photographs related to certain topics.

For example, interactive module 1802 of the project system 1800 may provide a registration screen, which may query the user regarding specific demographic information, such as name, age, address, gender, marital status and the like and query regarding the nature of the project. The module 1802 may then provide information and request input from the retiree specific to the nature of the project. The nature of the project being retirement planning in this example may cause the interactive module to filter through the options available and include questions regarding health needs, friends and family ties, monetary resources, financial condition and obligations, medical needs, hobbies, interests, activities, climate and other similarly associated parameters and guidelines.

In one embodiment, where appropriate to the nature of the project, the interactive module 1802 may use a visual format of inquiry, which provides, for example, photos and other images used to inspire the user and allow the user to create or conceive the project based on the look and feel of the project the user is desirous of creating.

Interactive module 1804 may be a database type of module used to make inquiries of the user regarding, for example, products, services and the like that may be available to or may be used by the retiree. In one embodiment, the database module may be a repository of archived information in the form of articles, photos, videos, reference guides and the like. Thus, for example, the retiree may input selections and receive information regarding health insurance, life insurance, medications used, hobbies, books, movies, adult living centers, and the like. Interactive module 1806, may accept additional information regarding options regarding desirable places to live, likes and dislikes, places to visit, favorite places to eat, favorite foods, sports, activity level, fitness level, cost of living and the like.

The information compiled in the interactive modules may be inserted or entered into the project system 1800 using any well known user interfaces, for example, but not limited to, a graphical user interfaces via fillable forms, selectable lists or images, and prompts, such as via an iterative interview process and the like.

Note that the interactive modules are part of the overall consultation package but have been described above as being separate modules to visually indicate that the initial inquiries may be parsed and separated into different categories based on the nature of the project, which can be activated using appropriate filters based on inputs entered by the user. Thus, some interactive modules 1807 (i.e. some lines of inquiry) may not be appropriate for certain projects and thus would not be included in the initial questioning once the nature of the project is ascertained. For example, a module that may query regarding career planning would not necessarily be included in the questioning of a person interested in retirement planning. However, the module directed at career planning may be included in the retirement planning line of questioning if the retiree let it be known that she may desire to reenter the work force after retirement.

As previously described, all information regarding the project is entered into the project system 1800 via planning sheets 1808. The planning sheets provide a means to classify and categorize the parameters, products, processes, professional services and the like of the planning phase. In the planning sheets, each bit of information received from the user is categorized and placed into the sheets. As shown in FIG. 18A, the planning sheets are represented as a wheel or circle divided into individual plan sections. Each individual plan section 1810 represents a different phase or aspect of the process, thus allowing the user to individually account for every phase and aspect of the planning process. The plan sections 1810 may be divided into any number of phases or aspects that may be considered a part of the planning process and may be individually customized by each user for each particular project. For example, in this embodiment, based on the nature of the project, plan sections may include categories such as finances, estate planning, housing, legal, travel, health, hobbies, interests, climate zones and other similar retirement related categories.

The plan sections 1810 may be further divided into classes and subclasses that account for particular aspects of the phase or aspect of the project. For example, under finances there may be sub-categories such as 401(k), IRA, annuities, savings, liabilities and the like. The plan sections may be individually searchable among each classification by all groups in the system. In one example, planning sheets may be divided into Headings, Categories and Subcategories. Thus, Finances may be a Heading, Savings may be a Category, and 401K may be a subcategory under the Savings category. Liabilities may also be a Category under Finances, while car payments or mortgages may be a subcategory under the Liabilities category. In each case categories and or subcategories link to professionals who are able to serve the individual if needed, products and or systems that are available to complete or support a process or project, further information on what others have done, what works, what does not work industry/sector best practices tools, equipment and the like If users want to reach out in a more informal process they may post requests for information in the Bid Inquiry Room or join a blog or forum or committee on the site.

As shown in the figure, the planning sheets 1808 transcend through the entire system. As the system continues toward the formation of the completed project portfolio, the planning sheets 1808 visually narrow, representing the fact that the information and data regarding the project are being refined. The planning sheets provide a visual tool that allows professionals, as well as the project owners (users), to view, select, and store for review information that has been placed into the project system through each segment of the project. In the present example, at the end of the concept phase, the retiree is able to view all of her selections and choices categorized and collected into separate sections for reviewing, editing and modifying, if desired.

In order to avoid having a vast amount of information and number of selectable choices to overwhelm the user of the project system 1800, the project system 1800 includes a filtering mechanism 1812 that provides a means for the user to draw down and narrow or limit his or her choices based on the specific project criteria and other information as well as selections made by the user in the consultation. The filtering mechanism 1812 receives all the information and data including design parameters, selections and other guidelines provided or selected by the user and entered via the planning sheets 1808, including cost/time/quality criteria. The information and data is filtered along the user's desired guidelines and parameters. In this example, if the retiree has entered information suggesting that she does not desire to live in a climate that is colder than a certain temperature in the winter, then the filter 1812 ensures that all information and requests for input that may relate to areas with a cold climate is subsequently excluded from further consideration. The filter causes the information and data to be reduced and segregated into appropriate plan sections of the planning sheets. The segregated information and data is saved and organized into appropriate categories and subcategories in the planning sheets. It should be noted that in the event that during the planning process the retiree changes her mind, the filter 1812 can subsequently allow any previously filtered information to be subsequently included.

Referring again to FIG. 18A, once the filtering mechanism 1812 has narrowed the information and data to a comprehensible selection of, for example, products, photos, professional services and options, the process of developing the vision album 1814 commences. The project system 1800 uses the information saved and stored in the planning sheets 1808 to create the vision album 1814. The provider group uses the vision album 1814 in collaboration with the user group to further refine and modify the information and data in the plan sections to develop the project guide.

In one embodiment, the filtering mechanism continues to filter the segregated information and data and further narrow the information data into specific needs, wants and desires. The filtering mechanism may arrive at the narrowed selections by, for example, further consultation with or questioning of the user regarding specific choices and their compatibility, desirability and usability with other choices and the overall vision of the project. Thus, the provider group makes additional queries and provides additional related information to the user group based on information in the vision album. These additional queries may take the creation of the project guide to new paths that are created as information in the planning sheets has been made to change.

Thus, as shown in FIG. 18A, multiple paths, such as paths 1 thru path N, where N may be any integer greater than 1, may be created based on the results of the queries and suggestions made during the consultation. Returning to the example of the retiree, a provider makes note that in the vision album the retiree states that she is a school teacher and that the she would like to continue to do charity work during her retirement years. The vision album also states that due to a health condition, the retiree needs to live primarily in a dry climate.

The provider group decides to make further inquires of the retiree asking, for example, if she had considered foreign countries with dry climates, if she speaks other languages, and whether she can teach English. Information is also presented to the retiree regarding each of these queries. The retiree considers these queries and begins to respond to them. Based on the responses, the project system begins to travel down path 1. The retiree decides that living in a foreign country may be nice and that she could definitely teach the English language. The provider group that makes the queries then begins to formulate the retiree's project guide 1822a using filters 1813. The provider group provides names of countries with dry climates, that need primary school teachers, and that need those teachers to volunteer their time. The retiree had never before considered doing these things in her retirement years, but now decides to select countries where she may retire that have a need for her teaching skills. The retirees planning sheets are updated with new information.

While continuing on path 1, the provider group continues to make further queries. This time the queries may focus on what is needed by the retiree now that she may be living in a foreign country. For example, the queries may include ideas on where to live (house versus apartment, buying versus renting), language lessons, travel restrictions or limitations that need to be overcome and so on. Again, queries are made and the list of possibilities is filtered 1813 and refined and added to the project guide, now referred to as project guide 1822b. The interactive query and refining process continues until the retiree has exhausted the options made available to her and has decided on the final design of her project.

The final selections prompted by the provider group and selected by the user are stored in a results portion of the planning sheets. The final project guide 1822 for path 1 is then completed.

In another embodiment, answers to queries from the provider group may create a different path, such as path 2. In this example, assuming that the retiree has no interest in living in a foreign country and also has no desire to teach after retiring, the provider group may offer queries about the retirees desire to travel around the United States and visit many small towns undiscovered by tourists. The retiree is also a Civil War history buff. Thus, queries from the providers may focus on these topics, which lead the providers to offer information regarding travel via motor home to small towns that were significant locations during the Civil War. The user believes this is a great idea and selects to find out more information about buying a motor home and selling her own home. The creation of the user project guide 1822a begins. This leads to more queries from the provider group regarding home sales, tax ramifications of home sales and more information about groups that travel together in motor homes around the United States. This leads to the reformulation of the project guide into project guide 1822b. Ultimately, the retiree's final selections are collected into the final project guide 1822.

The example provided above illustrates the nature of the iterative and interactive process of designing a project using the project system 1800. Any number of paths (1, 2, . . . N) may be created for the user, such that the user can find herself on path N that has considerably evolved from the initial path that had been started via the initially prepared vision album 1814. Thus, aspects of the present computer implemented methods, electronic systems, and computer operated programs include filters for aiding, suggesting, and solving questions that require decisions involving a planning project to maximize the project potential. By maximize, it is understood to mean better in most sense, such as faster, more economical, timeliness, user friendly, include best practices, more safe, more informative, more aesthetically appealing, more liked, more popular, etc., and combinations thereof. In one example, a planning project involves retirement planning. In other examples, planning projects include career planning, job planning, travel planning, elder care planning, construction planning, purchase planning, garden planning, event planning, and wedding planning, to name a few. The filters include pull down menus, pop up menus, based on categories, based on genre, based on price, based on quality, based on geographic location, and based on recommendations of others, or combinations thereof. The filters allow a user to initiate a project and end up with a maximized project. In other examples, a person or persons other than the initiator of the project perform the filters or answer the filters. Thus, aspects of the present embodiments include the production of a project portfolio that has been modified by at least one filter and the filtering is performed by the user or a person located remotely of the user. The remotely located person may be invited by the user to perform the filtering task or is electronically notified by the system to perform the filtering task due to the person being registered as a team member, outside expert, or consultant. In other examples, the remotely located person logs into a forum that posts several distinct or separate projects from different users to be filtered. The project portfolio therefore undergoes changes from an initial project and has its bugs and other problems, issues, or technical difficulties resolved through a series of filters and inputs from other individuals aside from the project initiator. In yet another example, the project portfolio undergoes changes throughout the life of the project. The changes are made in light of the filters and inputs from the various users and member groups discussed herein.

The completed project guide is provided to the facilitator group, which ultimately, for example, constructs the project based on the ideas and plans set forth in the project guide, inspired by the vision album, and refined in the query phase of the project. The facilitator group creates the project journal from the project guide as the work is being done. Thus, the project journal 1824 incorporates all the final information and data associated with the project. In one embodiment, the project journal is a form of the project guide that is being edited and revised until the project is complete. The retiree in this example, can pick-up her project journal at any time and check to see if her plan is on schedule and if she has accomplished or is accomplishing those things that she needs to do to get to her final destination. The transition between project guide and project journal may last as long as it takes to complete the project. For example, if a project is put on hold for a time, the project journal may not reflect any further work until the user begins the process again. When the project is complete to the satisfaction or agreement of the user, in combination, the vision album, the project guide and the project journal are combined to form the completed project portfolio 1826, which is a roadmap for implementation of the project. The project is complete when the facilitator group is done building the project and the last information has been added into the project journal.

As previously mentioned the project system 1800 may be used to plan any undertaking or project. For example, without any intention to be limiting, the user may choose to use the project system to aid in career planning or travel planning. Referring again to FIG. 18A, the description of the processes involved in the project system 1800 is now described with reference to each of these different planning requests. That is, the user group consists of a person who desires to undertake the project of planning for a career or for taking a trip.

In the example of the career planner, the user is a 20 year college student who has just completed two years of courses related to engineering but thinks he wants to be a lawyer. As before, during the project conception phase, the career planner is presented with a consultation package that includes interactive modules that provide information regarding the concept or vision for the project. As the career planner populates the user interface via fillable forms, selectable lists or images, and prompts, such as via an iterative interview process and the like, the information compiled in the interactive modules is entered into the project system 1800.

In order to determine a career option or opportunity a person needs to be asked certain questions and have access to good information that supports the answer(s). Thus, the project system begins a query of who, what, why, when, where then how. This career move is the result of a desire, a need, maybe even a premonition. A better project outcome in this case may need analyzing, comparing and a more complete understanding of the results of an outcome before the user actually commits his/her energy money and resources. Here the career planner may ask or be asked, what life do I want to live, will this career provide me with what I am looking for? Is income an important component, what can I expect to make at this job, career, to start, after I am accomplished? Am I better off having my own practice, what would that take? Where do I want to live, do I want to have children or if I have children would this be a proper environment? Once the user understands and verifies that this is the right step he may be guided through the process and be linked to the people who can help bring his dream, his desire, his need to completion. In this case it is best for a person who is serious about putting effort, energy and resources into a career path, that she be able to apply the best focus that results in a better project outcome. The project system asks, "Why have I made this choice?" and helps the user clarify and quantify the "project" guidelines, link them to professionals, mentors, industry experts and the like. In the Career project planning system the job of the Planning Kit and the Planning Guide is to clarify that the choice or thought is the right choice. Once this is done the Project is identified, it is time to start putting together the Vision Album. When the Vision Album is complete the user then turns the project over to or have people come on to help him/her complete the plan/design process. When they move onto the implementation or facilitation, they enter the process with road maps and specifications fully in place. The Planning here will result in a successful, better project outcome. If someone changes their mind and wants to modify their course during the process they can go back into the system and research other options and determine the best way to work them in or modify their course while maintaining as much value of their work to date.

For example, the career planner may provide user demographics (e.g., name, age, address, gender, marital status and the like) and states that he is an engineering student interested in a career in law. The module may then provide information and request input from the career planner specific to the nature of the project. The nature of the project, being career planning in this example, may cause the interactive module to filter through the options available and include questions regarding hobbies, previous occupations, education level, degrees held, degrees being pursued, skills, and other similarly associated parameters and guidelines. The interactive module may provide photos and other images used to inspire the user and allow the user to create or conceive the project based on the look and feel of the project the user is desirous of creating. For example, the interactive module may display to the career planner photos of lawyers at work in various settings, such as in a courtroom, a large firm, a small firm, working with indigents, in the board room of a corporation, working late hours, and the like. The system promotes and supports industry mentoring. The user is able to reach out to people and professionals who have taken similar paths.

Based on selections made by the career planner, the career planner may receive information regarding the various aspects of the legal profession. The interactive modules may accept additional information about options regarding salary expectations, lifestyle, family plans, financial resources and the like. In yet another interactive module, the career planner may be asked if he prefers to work in groups, to work alone, to speak to large groups of people, or prefers one on one discussion. The career planner may also be queried about his given abilities and talents, his limitations and his goals.

As previously described, all information regarding the project is entered into the project system 1800 via planning sheets 1808. In the planning sheets, each bit of information received from the user is categorized and placed into the sheets. For example, in this embodiment, based on the career planning nature of the project, plan sections may include categories such as education, desired careers, salary, family and lifestyle, finances, skills and hobbies and other similar career related categories. The plan sections 1810 may be further divided into classes and subclasses that account for particular aspects of the phase or aspect of the project, such as, under desired careers there may be sub-categories such as corporate attorney, litigator, transactional attorney, public interest attorney, and the like. Based on the queries made of the career planner, there may be indications that he may fall into multiple categories. In the present example, at the end of the concept phase, the career planner is able to view all of his inputs, selections and choices categorized and collected into separate sections for reviewing, editing and modifying, if desired.

The filtering mechanism 1812 receives all the information and data including design parameters, selections and other guidelines provided or selected by the user and entered via the planning sheets 1808. The information and data are filtered along the user's desired guidelines and parameters. In this example, if the career planner has entered information suggesting that he would like to attend law school in California and also work in the state, but also inputs that securities law is a strong interest, then the filter 1812 ensures that all information and requests for input that may relate to practice of law in California is included for consideration. However, the filter may still allow information about working on Wall Street in New York, since the career planner has suggested his interest in securities law. The filter causes the information and data to be reduced and segregated into appropriate plan sections. The segregated information and data are saved and organized into appropriate classes and subclasses in the planning sheets. The project system 1800 uses the information saved and stored in the planning sheets 1808 to create the vision album 1814.

The provider group uses the vision album 1814 in collaboration with the career planner to further refine and modify the information and data in the plan sections to develop the project guide. The provider group makes additional queries and provides additional related information to the user group based on the information in the vision album. In one embodiment, the filtering mechanism continues to filter the segregated information and data and further narrow the information data into specific needs, wants and desires of the career planner. In this example, the provider group may comprise law school counselors or admissions officers, legal recruiters, people interested in mentoring lawyers, financial aid counselors, scholarship writers and the like. In this example, the provider group may include not only persons but also sources of information and guidance. For example, the provider group may be an entity that provides access to data and information related to the practice of law and related topics, including LSAT test preparation, LSAT testing, law school rankings and the like.

As shown in FIG. 18A, multiple paths, such as paths 1 thru path N may be created based on the results of the queries and suggestions made during the consultation. Returning to the example of the career planner, a provider makes note that in the vision album the career planner states that he is an engineering undergraduate student and very active in various sports activities and performs in a local theater group.

The provider group decides to make further inquiries of what the career planner is asking. For example, asking if he had considered legal careers in sports or theatrical agency or law practice that can make use of his engineering degree, for example, patent law, construction defects, or product liability law. Information is also presented to the career planner regarding each of these queries. The career planner considers these queries and begins to respond to them. Based on the responses, the project system begins to travel down path 1 of FIG. 18A. The career planner had never known about patent law, but knows for sure that he is not interested in sports or theatrical agency. The provider group that is making the queries then begins to formulate the career planner's project guide 1822a. The provider group provides information to the career planner regarding intellectual property law, the practice of intellectual property law and requirements for becoming a patent attorney. The career planner is ecstatic to find out that he can use his engineering background in the practice of law so he continues to inquire. The provider's information mentions that the patent attorney must take an additional patent bar exam to become a patent attorney. The career planner is not that excited about the prospect of having to take another exam, but he is happy to know what awaits him in this career path.

While continuing on path 1, the provider group continues to make further queries. This time the queries may focus on compensation needs and lifestyle choices. For example, the queries may include charts and graphs showing typical salaries for various types of attorney practices, typical hours billed requirements, and job benefits. Again, queries are made and the list of possibilities refined and added to the project guide, now referred to as project guide 1822b. The interactive query and refining process continues until the career planner has exhausted the options made available to him and has decided on the final design of his career plan project. The final selections prompted by the provider group and selected by the user are stored in a results portion of the planning sheets. The final project guide 1822 for path 1 is then completed.

In another embodiment, answers to queries from the provider group may create a different path, such as path 2 of FIG. 18A. In this example, the career planner decides that he does not want to work for a big firm and would love to control his work hours. In this case, the provider group may offer queries about working as a solo practitioner. The career planner loves the prospect of being his own boss and selects various links to information regarding the practice of law as a solo practitioner to find out more information. The creation of the user project guide 1822a begins. This leads to more queries from the provider group regarding running a small business, which of course is an important part of running a solo law practice. This leads to the reformulation of the project guide into project guide 1822b.

At first, the career planner is overwhelmed by the endless set of rules and regulations that seem to accompany setting up a small law firm business. Suddenly, the career planner becomes fascinated with the idea of setting up a law practice focused on helping small business owners. The career planner begins to make inquiries of the provider group on this topic. Alas, the career planner is now headed down yet another path of inquiry and collaboration with the providers.

Alternatively, the providers note that most of the career planner's selections are slanted towards business consulting type work, so the providers begin to inquire and inform the career planner about alternative careers in business consulting. The filter mechanisms began to allow inclusion of more business consulting oriented options. As a result of this new found desire to aid small business owners, the career planner may decide not to venture into the law field at all but may feel better suited for a career as a business consultant. The career planner continues to make inquiries of the provider group on this new topic. The career planner is now headed down yet another path of inquiry and collaboration with the providers that heretofore the career planner had not even considered.

Ultimately, the career planner's final selections are collected into the final project guide 1822.

Assuming again that the career planner desires to be an attorney, once the project guide 1822 has been completed, the career planner has a good idea of what is required to become an attorney. For example, the career planner now knows that he must take an LSAT exam to be able to apply for law school, he must attend law school for at least three years, and he must pass a state bar exam to actually practice law. The career planner also knows generally which types of careers a lawyer may pursue and he knows specifically what is required to become, for example, a patent attorney, a district attorney, or a public interest attorney to name but a few of the attorney types that the career planner chose to inquire about, or all of them. Because the career planner has made these inquiries early in his career path, he has a prepared timeline in the project guide showing him when he should have accomplished certain tasks to implement his project.

At some time, the career planner's completed project guide is provided to the facilitator group, which ultimately helps the career planner to put the plan into action. The facilitators may include, law school admission representatives, teachers, counselors, financial aid planners, practicing patent attorneys, and the like. While in law school, the facilitators may include tutors and those that can help a student with internships. Once law school has been completed, the facilitator group may become educational representatives from bar exam study groups and employment recruiters. Thus, the facilitator group can vary over time as the project continues to evolve. The facilitator group documents the events that lead to the creation of the project journal 1824 that incorporates all the final information and data associated with the career development project. In combination, the vision album, the project guide and the project journal are combined to form the completed project portfolio 1826, which is a roadmap for implementation of the project. The career planner in this example, can pick-up his project portfolio at any time and check to see if his plan is on schedule and if he has accomplished those things that he needs to do get to his final destination. This includes returning to the completed portfolio, even after the project is completed (i.e. the career planner has become a lawyer) to find the name of the employment recruiter (facilitator) who helped him get his first job, because the career planner is now looking to find a new place to work.

The project system can similarly be used to plan travel. In the example of the traveler, the traveler desires to take a simple trip to Europe or some similar place but has no real idea where to go. The traveler interacts with the consultation package, which queries the traveler about the traveler's interests. The information is compiled in the interactive modules and entered into the project system 1800 using the planning sheets 1810.

The nature of the project being travel to Europe in this example may cause the interactive module to filter through the options available and include questions regarding interests, favorite foods, other places that the traveler has traveled, and other similarly associated parameters and guidelines. The interactive module may provide photos and other images used to inspire the user and allow the user to create or conceive the project based on the look and feel of the places the traveler may want to go. For example, the interactive module may display to the traveler photos of ancient ruins in Rome, pyramids in Egypt or the Eiffel Tower in France.

Based on selections made by the traveler, the traveler may receive information regarding the various aspects of travel through Europe, Africa or Asia. The interactive modules may accept additional information about options regarding food and other allergies, physical travel limitations, budget requirements and the like. In yet another interactive module, the traveler may be asked if the traveler prefers traveling alone, in groups or a mix of both. In yet another interactive module the traveler is queried about hobbies, skills and the like.

As previously described, all information regarding the project is entered into the project system 1800 via planning sheets 1808. In the planning sheets, each bit of information received from the user is categorized and placed into the sheets in categories, such as budget, lodging, transportation, activities, countries to visit and the like. The plan sections 1810 may be further divided into classes and subclasses that account for particular aspects of the phase or aspect of the project, such as, under budget there may be sub-categories such as length of stay, monetary conversion rates, and the like. In the present example, at the end of the concept phase, the traveler is able to view all of his inputs, selections and choices categorized and collected into separate sections for reviewing, editing and modifying, if desired.

The filtering mechanism 1812 receives all the information and data including design parameters, selections and other guidelines provided or selected by the user and entered via the planning sheets 1808. The information and data is filtered along the user's desired guidelines and parameters. In this example, if the traveler has entered information suggesting that the traveler has once traveled to Asia then the filter 1812 ensures that all information and requests for input that may related to travel in Asia is not included for consideration. The filter causes the information and data to be reduced and segregated into appropriate plan sections. The segregated information and data is saved and organized into appropriate classes and subclasses in the planning sheets. The project system 1800 uses the information saved and stored in the planning sheets 1808 to create the vision album 1814.

The provider group uses the vision album 1814 in collaboration with the career planner to further refine and modify the information and data in the plan sections to develop the project guide. The provider group makes additional queries and provides additional related information to the user group based on the information in the vision album. In one embodiment, the filtering mechanism continues to filter the segregated information and data and further narrow the information data into specific needs, wants and desires of the career planner. In this example, the provider group may comprise travel professionals.

In this example, the provider makes note that in the vision album the traveler states that he is an artist who is fascinated with Italian artists. The provider group decides to make further inquires of the traveler asking, for example, if he had considered traveling to Rome to view various works of art in various museums. Information is presented to the career planner regarding this query. The traveler considers this query and responds affirmatively. Based on the response, the project system begins to travel down path 1 of FIG. 18A. The provider group that is making the queries then begins to formulate the traveler's project guide 1822a. The provider group provides information to the career planner regarding Italian artists and museums and the like, which hold their art work. The provider also notes that the traveler has a very tight travel budget. Thus, the providers provide information to the traveler regarding low cost, but quality lodging. The providers also suggest a centralized location for the traveler to stay so that he can be as close as possible to the museums that have been identified, this helps to keep transportation costs down. The providers also suggest various modes of travel, such as buses that are cheaper alternatives to, for example, taxi cabs and the like.

In another embodiment, answers to queries from the provider group may create a different path, such as path 2 of FIG. 18A. In this example, the traveler has stated that he is not interested in seeing any one particular thing, but would rather travel through Europe, with no particular time schedule or itinerary, stopping at various locations and staying for various lengths of time. In this case, the provider group may offer queries about train travel through Europe and offer suggestions for various routes that optimize the traveler's ability to see as many countries as possible in the span of time that the traveler has specified. The providers also provide information of lodging in hostels, which may be ideal for this type of travel. The creation of the user project guide is begun. This leads to more queries from the provider group regarding obtaining visas, monetary exchanges, local transportation, expected language barriers and travel warnings and the like. Once selected, all of the information that the traveler chooses to rely on is incorporated into the project guide.

In this example, once the project journal 1822 has been completed, the traveler has a plan for traveling by train to see five countries in Europe in 20 days. The traveler's completed project guide is provided to the facilitator group, which helps the traveler to put the trip plan into action. The facilitators may include travel agents, lodgers, transportation specialists, money exchangers and the like who can help to implement the actual travel desires of the traveler. The facilitator group documents each aspect of the trip plan that leads to the creation of the project journal that incorporates all the final information and data associated with the travel project. As before, in combination, the vision album, the project guide and the project journal are combined to form the completed project portfolio. The traveler may at anytime before, during or after the trip view any aspect of the travel plan.

Thus, the technical features of the computer implemented system for generating a project planning document may include mechanisms for presenting queries relating to a project type to prompt first inputs from a first user; filtering the first inputs to populate segments of an initial planning sheet representing an initial planning path with the filtered first inputs, the filtering based on user selections from the first user provided in response to the initial queries to create an initial project plan; presenting a plurality of additional queries based on the filtered first inputs to prompt a plurality of secondary inputs; filtering the plurality of secondary inputs to populate segments of an alternative planning sheet representing an alternative planning path with filtered secondary inputs, the filtering based on user selections from the first user provided in response to the plurality of additional queries, wherein an alternative project plan is produced from the alternative planning path, which is different from the initial project plan, and creating a first guide that includes the alternative project plan; modifying the alternative project plan in response to interactive and collaborative queries made between the first user and a second user to produce a modified alternative project plan, and creating a second guide that includes the modified alternative project plan; recording actions taken and the progress being made in implementing the modified alternative project plan in a third guide; and generating a project planning document including at least the information included in the first guide, the second guide and the third guide.

Although embodiments and their components have been specifically described and illustrated, many modifications, combinations, and variations of the embodiments will be apparent to those skilled in the art. Furthermore, it is understood and contemplated that features specifically discussed for one embodiment may be adopted for inclusion with another embodiment provided the functions are compatible. Accordingly, it is to be understood that the planning system and components thereof developed and implemented according to principles of this disclosure may be embodied other than as specifically described herein. The invention is defined in the following claims.

What is claimed is:

1. A method of collaboratively generating a virtual project portfolio for a construction project comprising using a non-transitory computer useable medium having computer readable instructions embodied therein, wherein the computer readable instructions cause a computer to:
   receive first construction project information inputs about the construction project from a first user interface, wherein the first construction project information inputs include a type of construction and a space in a structure included in the construction project;
   select a first set of filters from a plurality of filters stored in memory to obtain information relating to the space based on at least the type of construction and the space in the structure included in the construction project received in the first construction project information of information from the first user;
   generate a first portion of the project portfolio on the memory, wherein the first portion of the project portfolio comprises a vision album comprising the construction space information obtained from at least one database maintained in the memory using the first set of filters selected using the first construction project information inputs, wherein the vision album comprising the construction space information includes a first list of professionals based on the first construction project information inputs;
   provide the first portion of the project portfolio to the first user interface to allow the first user interface to modify the first portion of the project portfolio and to select a first professional from the first list of professionals;
   receive first selection information inputs from the first user interface, wherein the first selection information inputs include a selection of the first professional from the first list of professionals;
   grant access to the first portion of the project portfolio to the selected first professional;
   notify the selected first professional that second construction project information inputs must be provided via the second user interface;
   provide the first portion of the project portfolio to the selected first professional via a second user interface in response to the selection of the selected first professional from the first user interface;
   receive second construction project information inputs from the second user interface; modify the first portion of the project portfolio using the second construction project information inputs received from the second user interface;
   generate a second portion of the project portfolio on the memory comprising a second list of professionals based on the modified first portion of the project portfolio, wherein the second list of professionals is different than the first list of professionals;
   provide the second portion of the project portfolio to the second user interface to allow the second user interface to modify the first portion of the project portfolio and to select a second professional from the second list of professionals;
   receive second selection information inputs from the second user interface, wherein the second selection information inputs includes a selection of the second professional, different from the first professional, from the second list of professionals;
   grant access to the first portion of the project portfolio to the selected second professional;
   notify the selected second professional that third construction project information inputs must be provided via the third user interface;

provide the second portion of the project portfolio to the selected second professional via a third user interface in response to the selection of the selected second professional from the second user interface;

receive third construction project information inputs from the third user interface to allow the third user interface to modify the first portion of the project portfolio; and modify the first portion of the project portfolio using the third construction project information received from the third user interface.

2. The method of claim 1, further comprising assembling the first, second, and third guides into the virtual planning guide.

3. The method of claim 1, further comprising requesting the developer user of the first user interface to input user selections that include parameters, guidelines, product and service selections and receiving user selections input by the first user interface.

4. The method of claim 1, further comprising providing one or more links for the first user interface to link to information to search, view and select parameters, guidelines, product selections and service selections to be included in the user selections.

5. The method of claim 4, wherein the first user interface is provided with links to information providers to search, view and select information about the construction project and wherein the information providers comprise public sector groups, industry professionals, manufacturers and industry service professionals and wherein the computer readable instructions include instructions to receive a selection of at least a portion of the information to be included in the first portion of the project portfolio in the inputs received from the first user interface.

6. The method of claim 1, further comprising providing one or more links for the first user interface to link to information provided by information providers to search, view and select the information to be included in the information received from the first user.

7. The method of claim 6, wherein the information providers comprise public sector groups, industry professionals, manufactures and industry service professionals.

8. The method of claim 6, wherein the information provided comprises service listings, manufacturer showrooms, professional showcases, and network listings.

9. The method of claim 6, wherein the information provided by the links comprises at least one of service listings, manufacturer showrooms, professional showcases, and network listings.

10. The method of claim 1, further comprising creating a planning sheet including plan sections representing different plan section categories related to aspects of the construction project, wherein each plan section includes a listing of tasks and requirements related to a particular category; segregating the portions of the information received from the first user interface into the appropriate plan section categories; maintaining the user selections as input by the first user interface and as modified by the second user interface and third user interface; and maintaining a journal of the actions taken in implementing the project.

11. The method of claim 1, wherein the computer readable instructions when executed on the computer cause the computer to: generate a third portion of the project portfolio comprising a project journal that records information about actions taken by the first, second, and third user interfaces to modify the project portfolio.

12. The method of claim 1, wherein the second portion of the project portfolio comprises a residential construction project or a commercial construction project that has been modified by the second professional via the third user interface.

13. The method of claim 1, wherein the plurality of filters includes a project scope filter, a climate zone filter, an architectural style filter, a system filter, a foundation filter, a flooring filter, a color filter, and a material filter.

14. The method of claim 1, wherein the computer readable instructions when executed on the computer cause the computer to modify any portion of the project portfolio via the first user interface, the second user interface, and the third user interface.

15. The method of claim 1, wherein the information in the first portion of the project portfolio includes monetary bids provided by qualified professionals for providing products and services.

16. The method of claim 1, further comprising presenting an option for the first user interface to modify input from at least one of the second user interface and the third user interface.

17. A method for generating a virtual planning guide for a construction project performed by one or more computers over a network comprising:

receiving first construction project information inputs about the construction project from a first user interface, wherein the first construction project information inputs include a type of construction and a space in a structure included in the construction project;

selecting a first set of filters from a plurality of filters stored in memory to obtain information relating to the space based on at least the type of construction and the space in the structure included in the construction project received in the first construction project information of information from the first user;

generating a first portion of the project portfolio on the memory, wherein the first portion of the project portfolio comprises a vision album comprising the construction space information obtained from at least one database maintained in the memory using the first set of filters selected using the first construction project information inputs, wherein the vision album comprising the construction space information includes a first list list of professionals based on the first construction project information inputs;

providing the first portion of the project portfolio to the first user interface to allow the first user interface to modify the first portion of the project portfolio and to select a first professional from the first list of professionals;

receiving first selection information inputs from the first user interface, wherein the first selection information inputs include a selection of the first professional from the first list of professionals;

granting access to the first portion of the project portfolio to the selected first professional;

notifying the selected first professional that second construction project information inputs must be provided via the second user interface;

providing the first portion of the project portfolio to the selected first professional via a second user interface in response to the selection of the selected first professional from the first user interface;

receiving second construction project information inputs from the second user interface;

modifying the first portion of the project portfolio using the second construction project information inputs received from the second user interface;

generating a second portion of the project portfolio on the memory comprising a second list of professionals based on the modified first portion of the project portfolio, wherein the second list of professionals is different than the first list of professionals;

providing the second portion of the project portfolio to the second user interface to allow the second user interface to modify the first portion of the project portfolio and to select a second professional from the second list of professionals;

receiving second selection information inputs from the second user interface, wherein the second selection information inputs includes a selection of the second professional, different from the first professional, from the second list of professionals; granting access to the first portion of the project portfolio to the selected second professional;

notifying the selected second professional that third construction project information inputs must be provided via the third user interface;

providing the second portion of the project portfolio to the selected second professional via a third user interface in response to the selection of the selected second professional from the second user interface;

receiving third construction project information inputs from the third user interface to allow the third user interface to modify the first portion of the project portfolio; and modifying the first portion of the project portfolio using the third construction project information received from the third user interface.

18. The method of claim 17, further comprising assembling the first, second, and third guides into the virtual planning guide.

19. The method of claim 17, further comprising requesting the developer user of the first user interface to input user selections that include parameters, guidelines, product and service selections and receiving user selections input by the first user interface.

20. The method of claim 17, further comprising providing one or more links for the first user interface to link to information to search, view and select parameters, guidelines, product selections and service selections to be included in the user selections.

* * * * *